(12) United States Patent
Parham et al.

(10) Patent No.: US 11,437,588 B2
(45) Date of Patent: Sep. 6, 2022

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Jonas Kroeber, Frankfurt am Main (DE); Jens Engelhart, Darmstadt (DE); Anja Jatsch, Frankfurt am Main (DE); Christian Eickhoff, Mannheim (DE); Christian Ehrenreich, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 124 days.

(21) Appl. No.: 16/758,672

(22) PCT Filed: Oct. 22, 2018

(86) PCT No.: PCT/EP2018/078822
§ 371 (c)(1),
(2) Date: Apr. 23, 2020

(87) PCT Pub. No.: WO2019/081391
PCT Pub. Date: May 2, 2019

(65) Prior Publication Data
US 2020/0358005 A1    Nov. 12, 2020

(30) Foreign Application Priority Data

Oct. 24, 2017  (EP) .................................... 17197889

(51) Int. Cl.
| | | |
|---|---|---|
| *C07D 471/04* | (2006.01) | |
| *H01L 51/00* | (2006.01) | |
| *C07D 471/14* | (2006.01) | |
| *C07D 487/22* | (2006.01) | |
| *C09K 11/06* | (2006.01) | |
| *H01L 51/50* | (2006.01) | |

(52) U.S. Cl.
CPC ........ *H01L 51/0072* (2013.01); *C07D 471/04* (2013.01); *C07D 471/14* (2013.01); *C07D 487/22* (2013.01); *C09K 11/06* (2013.01); *H01L 51/0067* (2013.01); *H01L 51/0073* (2013.01); *H01L 51/0074* (2013.01); *C09K 2211/1018* (2013.01); *H01L 51/5012* (2013.01); *H01L 51/5016* (2013.01); *H01L 51/5056* (2013.01); *H01L 51/5072* (2013.01); *H01L 51/5096* (2013.01)

(58) Field of Classification Search
CPC .. C07D 471/04; C07D 471/14; C07D 487/14; C07D 487/22; H01L 51/0067; H01L 51/0072; H01L 51/0073; H01L 51/0074; H01L 51/0512; H01L 51/42; H01L 51/5012; H01L 51/5016; H01L 51/5056; H01L 51/5072; H01L 51/5096; C09K 11/06; C09K 2211/1018; Y02E 10/549
See application file for complete search history.

(56) References Cited

U.S. PATENT DOCUMENTS 10,981,938 B2 *  4/2021  Joo .................. H01L 51/008

FOREIGN PATENT DOCUMENTS

WO   WO-2017078182 A1   5/2017

OTHER PUBLICATIONS

International Search Report for PCT/EP2018/078822 dated Nov. 21, 2018.
Written Opinion of the International Searching Authority for PCT/EP2018/078822 dated Nov. 21, 2018.

* cited by examiner

*Primary Examiner* — Mark Kopec
*Assistant Examiner* — Jaison P Thomas
(74) *Attorney, Agent, or Firm* — Faegre Drinker Biddle & Reath LLP

(57) ABSTRACT

The invention relates to compounds of formula (1) which are suitable for use in electronic devices, and to electronic devices, in particular organic electroluminescent devices, containing said compounds.

15 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2018/078822, filed Oct. 22, 2018, which claims benefit of European Application No. 17197889.3, filed Oct. 24, 2017, both of which are incorporated herein by reference in their entirety.

The present invention relates to materials for use in electronic devices, especially in organic electroluminescent devices, and to electronic devices, especially organic electroluminescent devices comprising these materials.

Emitting materials used in organic electroluminescent devices (OLEDs) are frequently phosphorescent organometallic complexes. In general terms, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, such as matrix materials, are also of particular significance here. Improvements to these materials can thus also lead to improvements in the OLED properties.

The problem addressed by the present invention is that of providing compounds suitable for use in an OLED, especially as matrix material for phosphorescent emitters, but also as electron transport materials or hole blocker materials. A further problem addressed by the present invention is that of providing further organic semiconductors for organic electroluminescent devices, in order thus to enable the person skilled in the art to have a greater possible choice of materials for the production of OLEDs.

It has been found that, surprisingly, particular compounds described in detail hereinafter solve this problem and are of good suitability for use in OLEDs. These OLEDs especially have a long lifetime, high efficiency and low operating voltage. The present invention therefore provides these compounds and electronic devices, especially organic electroluminescent devices, comprising such compounds.

The present invention provides a compound of formula (1)

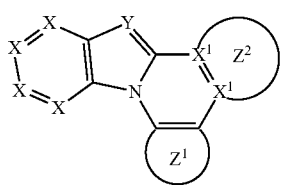

Formula (1)

where the symbols used are as follows:
$Z^1$ is a group of the formula (2)

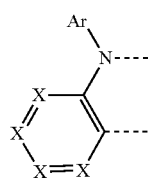

Formula (2)

where the dotted bonds indicate the linkage of this group to the two carbon atoms explicitly marked in formula (1);

$Z^2$ is a group of the formula (3), (4) or (5)

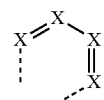

Formula (3)

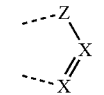

Formula (4)

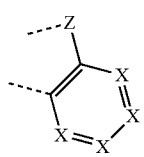

Formula (5)

where the dotted bonds indicate the linkage of this group to $X^1$ in formula (1);

$X^1$ is C at each instance when $Z^2$ is a group of the formula (3), or is C at each instance when $Z^2$ is a group of the formula (4) or (5) in which Z is NAr, or one $X^1$ group is C and the other $X^1$ group is N when $Z^2$ is a group of the formula (4) or (5) in which Z is CR or N;

X is the same or different at each instance and is CR or N;

Y is CR or N;

Z is CR or N when one $X^1$ group is C and the other $X^1$ group is N, and Z is NAr when both $X^1$ groups are C;

Ar is the same or different at each instance and is an aromatic or heteroaromatic ring system which has 5 to 40 aromatic ring atoms and may be substituted by one or more R radicals;

R is the same or different at each instance and is H, D, F, Cl, Br, I, $N(Ar')_2$, $N(R^1)_2$, OAr, SAr, CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms, preferably 5 to 40 aromatic ring atoms, and may be substituted in each case by one or more $R^1$ radicals; at the same time, two R radicals together may also form a ring system;

Ar' is the same or different at each instance and is an aromatic or heteroaromatic ring system which has 5 to 40 aromatic ring atoms and may be substituted by one or more $R^1$ radicals;

$R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals, where one or more nonadjacent $CH_2$ groups may be replaced by Si(R$^2$)$_2$, C=O, NR$^2$, O, S or CONR$^2$ and where one or more hydrogen atoms in the alkyl, alkenyl or alkynyl group may be replaced by D, F, Cl, Br, I or CN, or an aromatic or heteroaromatic ring system which has 5 to 40 aromatic ring atoms and may be substituted in each case by one or more R$^2$ radicals; at the same time, two or more R$^1$ radicals together may form a ring system;

R$^2$ is the same or different at each instance and is H, D, F, CN or an aliphatic, aromatic or heteroaromatic organic radical, especially a hydrocarbyl radical, having 1 to 20 carbon atoms, in which one or more hydrogen atoms may also be replaced by F.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 60 carbon atoms, preferably 6 to 40 carbon atoms, in the ring system. A heteroaromatic ring system in the context of this invention contains 2 to 60 carbon atoms, preferably 2 to 40 carbon atoms, and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. These shall likewise be understood to mean systems in which two or more aryl or heteroaryl groups are joined directly to one another, for example biphenyl, terphenyl, bipyridine or phenylpyridine. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferred aromatic or heteroaromatic ring systems are simple aryl or heteroaryl groups and groups in which two or more aryl or heteroaryl groups are joined directly to one another, for example biphenyl or bipyridine, and also fluorene or spirobifluorene.

In the context of the present invention, an aliphatic hydrocarbyl radical or an alkyl group or an alkenyl or alkynyl group which may contain 1 to 40 carbon atoms and in which individual hydrogen atoms or CH$_2$ groups may also be substituted by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group OR' having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group SR' having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent CH$_2$ groups may be replaced by the abovementioned groups; in addition, it is also possible for one or more hydrogen atoms to be replaced by D, F, Cl, Br, I, CN or NO$_2$, preferably F, Cl or CN, more preferably F or CN.

An aromatic or heteroaromatic ring system which has 5-60 aromatic ring atoms and may also be substituted in each case by the abovementioned R$^2$ radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from combinations of these systems. When two R or R$^1$ radicals together form a ring system, it may be mono- or polycyclic, and aliphatic, heteroaliphatic, aromatic or heteroaromatic. In this case, the radicals which together form a ring system are preferably adjacent, meaning that these radicals are bonded to the same carbon atom or to carbon atoms directly bonded to one another.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

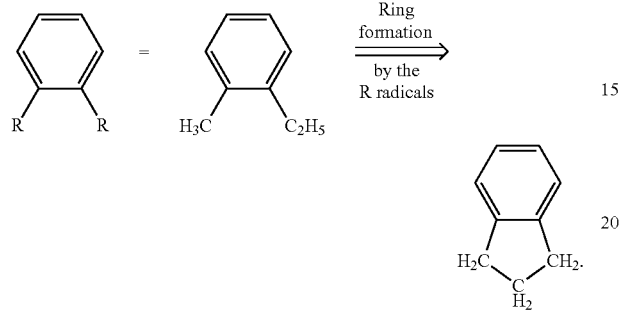

In addition, however, the abovementioned wording shall also be understood to mean that, if one of the two radicals is hydrogen, the second radical binds to the position to which the hydrogen atom was bonded, forming a ring. This shall be illustrated by the following scheme:

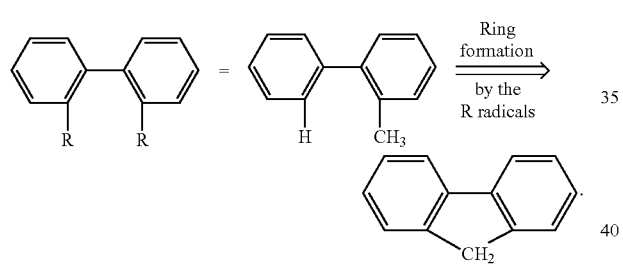

The formation of an aromatic ring system shall be illustrated by the following scheme:

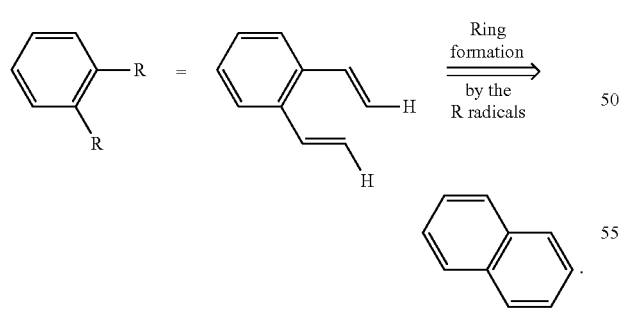

When $Z^2$ is a group of the formula (3), there is formally a double bond between the two $X^1$ atoms, such that the $Z^2$ group together with the two $X^1$ is an aromatic or heteroaromatic group. When $Z^2$ is a group of the formula (4) or (5) in which Z is NAr, there is formally a double bond between the two $X^1$ atoms that are both C, such that the $Z^2$ group together with the two $X^1$ is a heteroaromatic group. When the $Z^2$ group is a group of the formula (4) or (5) in which Z is CR or N, there is formally a double bond between the $X^1$ atom which is C and the atom in the group of the formula (4) or (5) to which this $X^1$ binds, such that the $Z^2$ group together with the two $X^1$ is a heteroaromatic group.

Two different isomers arise according to the alignment of the $Z^1$ group. These are represented hereinafter by the formulae (6) and (7)

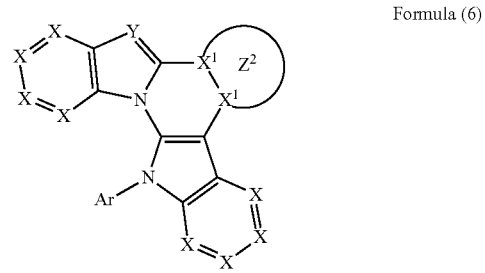
Formula (6)

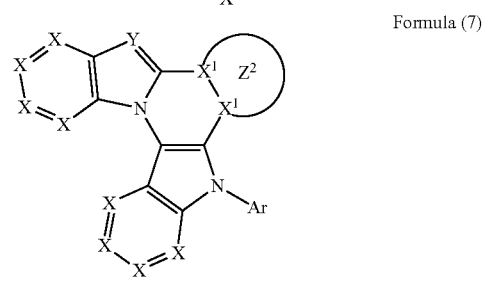
Formula (7)

where the symbols used have the definitions given above.

Various compounds arise according to the choice of $Z^2$ and $X^1$ groups. These are represented hereinafter by the formulae (8) to (18):

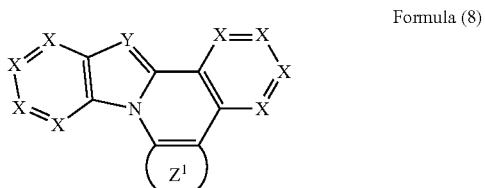
Formula (8)

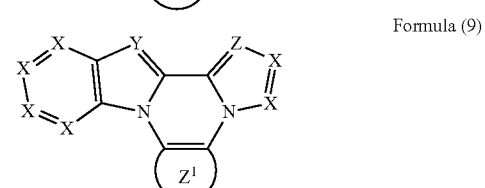
Formula (9)

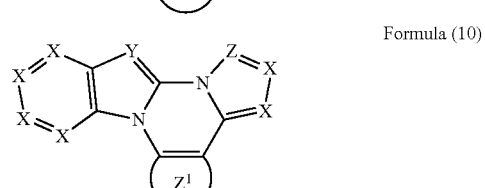
Formula (10)

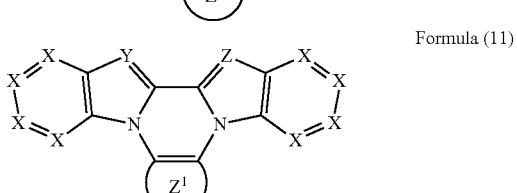
Formula (11)

Formula (12)
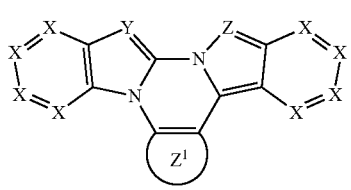

Formula (13)
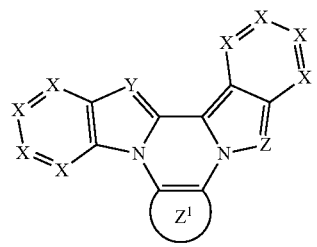

Formula (14)
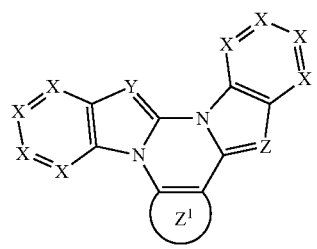

Formula (15)
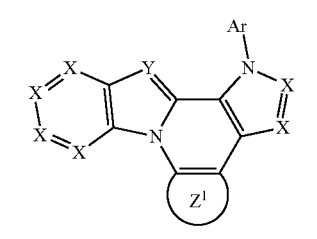

Formula (16)
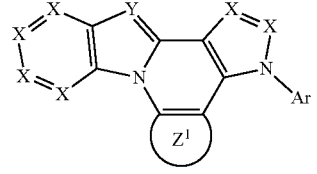

Formula (17)
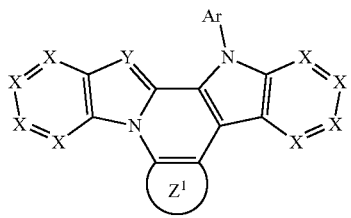

Formula (18)
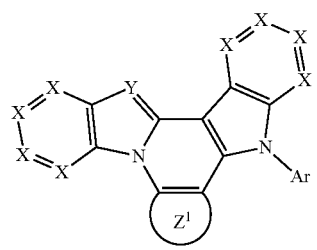

where the symbols have the same definitions as given above, and Z in the formulae (9) to (14) is CR or N. Preference is given to compounds of the formula (8).

In a preferred embodiment of the invention, all symbols X in formula (2) are CR, such that the $Z^1$ group in formula (1) is a group of the following formula (2a):

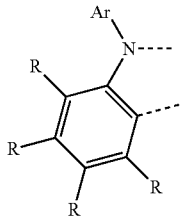
Formula (2a)

where the symbols used have the definitions given above.

In a further preferred embodiment of the invention, in the formulae (1) and (3) to (18), not more than one symbol X per cycle is N and the other symbols X are CR. In a particularly preferred embodiment of the invention, not more than one symbol X in the formulae (1) and (6) to (18) is N, and the other symbols X are CR. It is particularly preferable here when $Z^1$ is a group of the formula (2a) detailed above.

A preferred embodiment of the formulae (6) and (7) is thus the compounds of the following formulae (6a) and (7a):

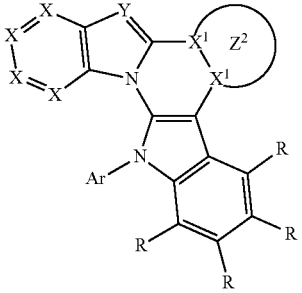
Formula (6a)

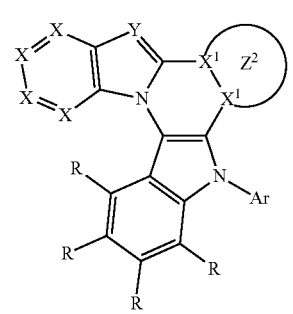
Formula (7a)

where the symbols used have the definitions given above and not more than one X in the compound including the structure $Z^2$ is N.

In a particularly preferred embodiment of the invention, all X are CR, and so the compounds of the formulae (8) to (18) can be represented by the following formulae (8a) to (18b):

Formula (8a)
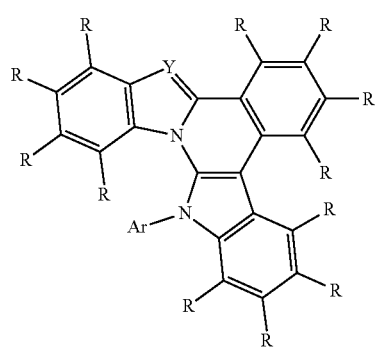
Formula (8b)
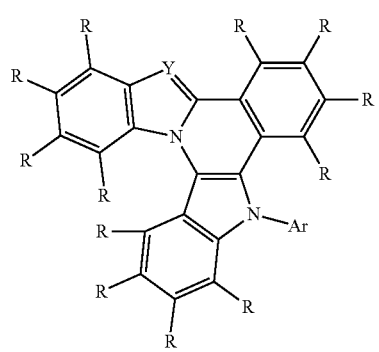
Formula (9a)
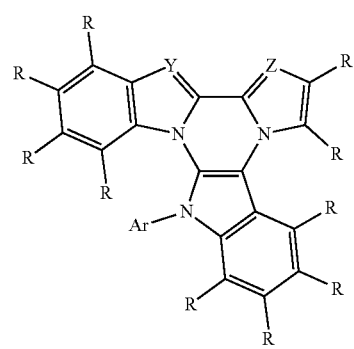
Formula (9b)
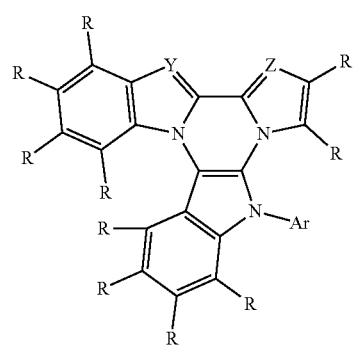
Formula (10a)
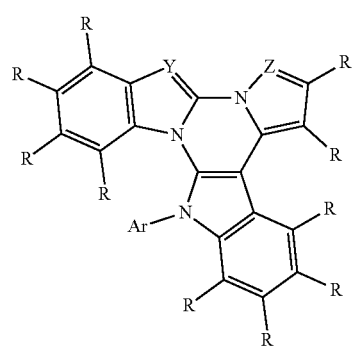
Formula (10b)
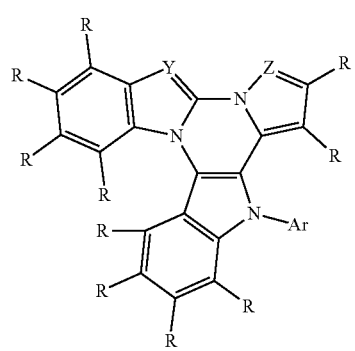
Formula (11a)
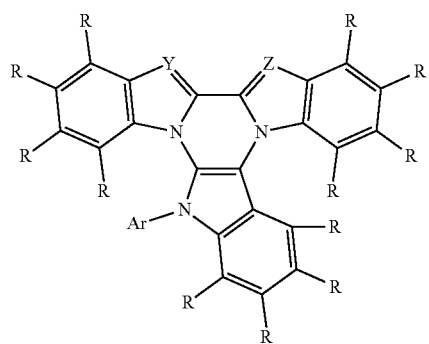
Formula (11b)
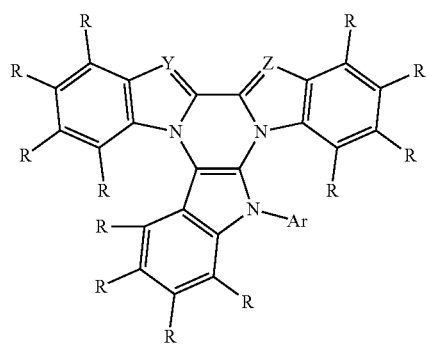

Formula (12a)
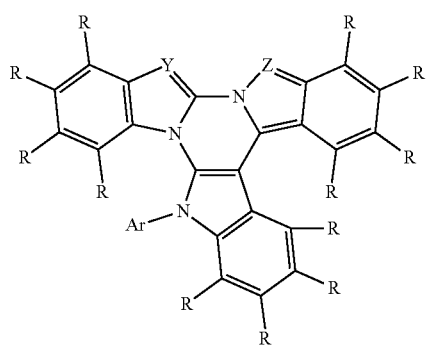
Formula (12b)
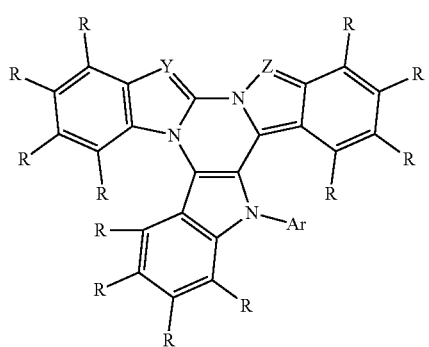
Formula (13a)
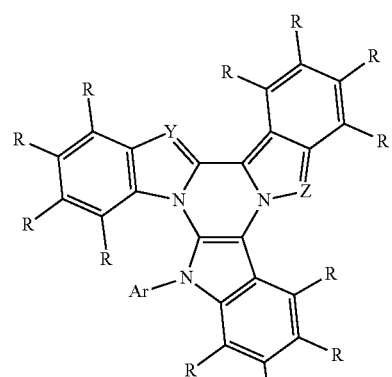
Formula (13b)
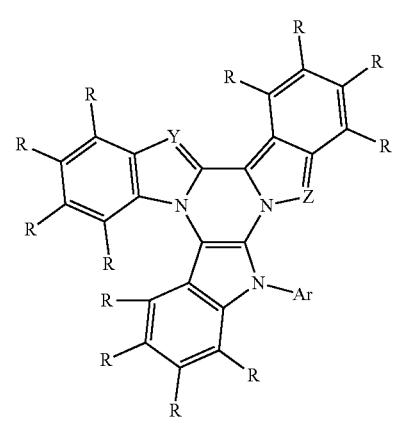
Formula (14a)
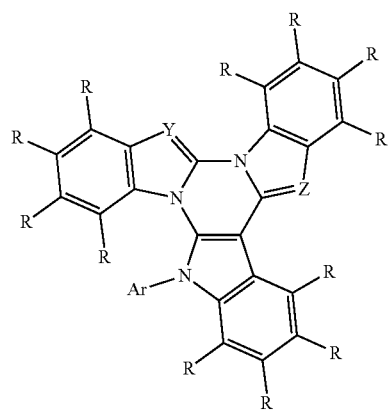
Formula (14b)
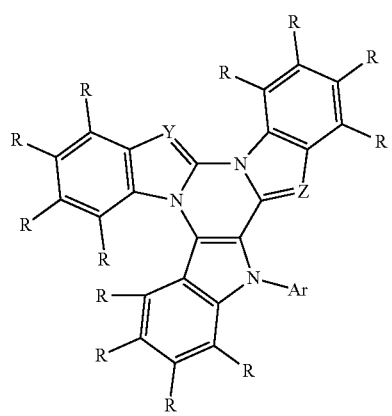
Formula (15a)
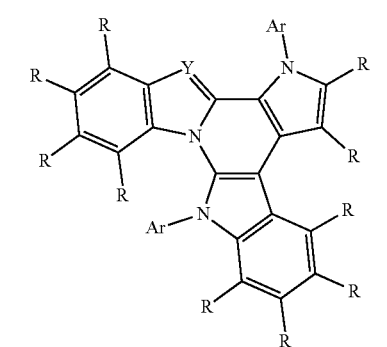
Formula (15b)
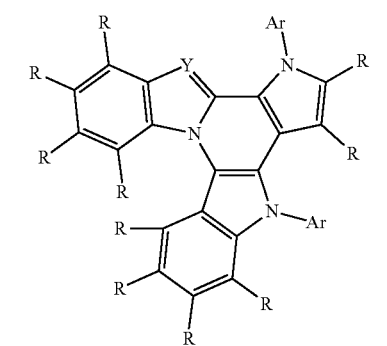

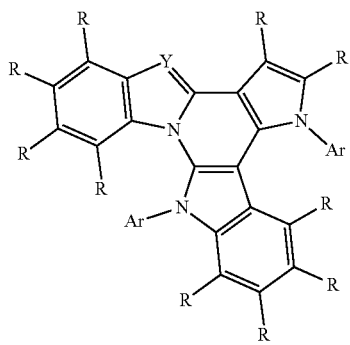

Formula (16a)

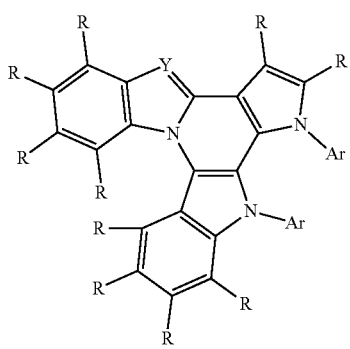

Formula (16b)

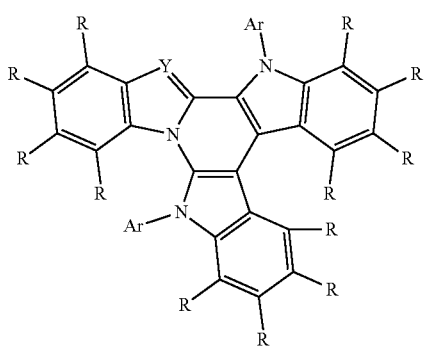

Formula (17a)

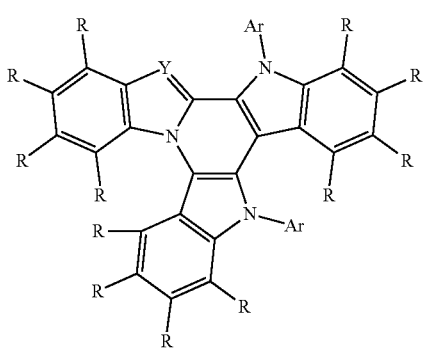

Formula (17b)

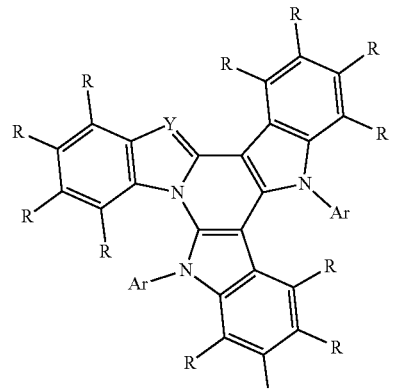

Formula (18a)

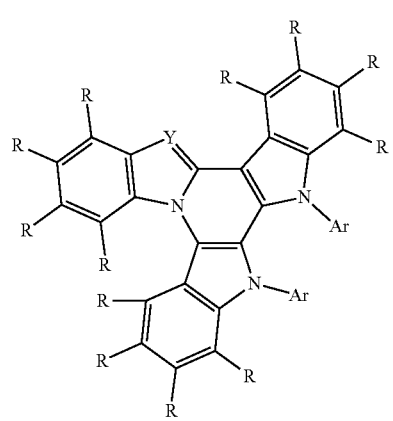

Formula (18b)

where the symbols used have the definitions given above and Z in the formulae (9a) to (14b) is CR or N.

Particular preference is given to the structures of the formulae (8a) and (11a).

In a preferred embodiment of the invention, not more than three R radicals in total, more preferably not more than two R radicals and most preferably not more than one R radical, in the compound of the formula (1) or the preferred structures detailed above are/is a group other than hydrogen. In a further preferred embodiment of the invention, at least one Y is CR, and the radical on this carbon atom represented by the Y and not more than two further R radicals, more preferably not more than one further R radical, in the compound of the formula (1) or the preferred structures detailed above are not hydrogen.

In a particularly preferred embodiment of the invention, the compound of the formula (1) is selected from the compounds of the following formulae (8a-1) to (18b-1), Formula (8a-1)

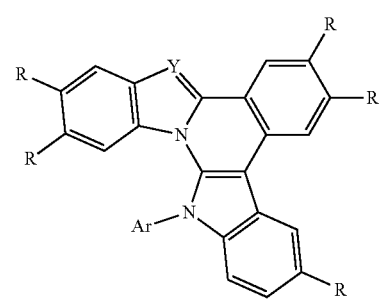

Formula (8b-1)
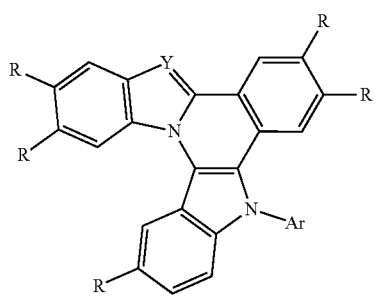
Formula (9a-1)
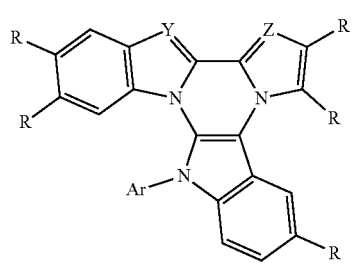
Formula (9b-1)
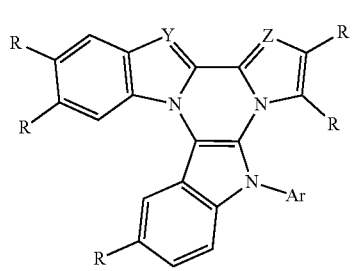
Formula (10a-1)
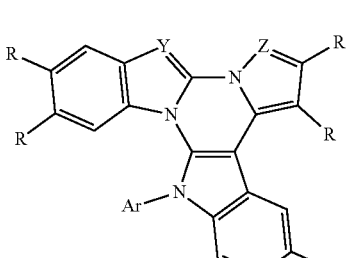
Formula (10b-1)
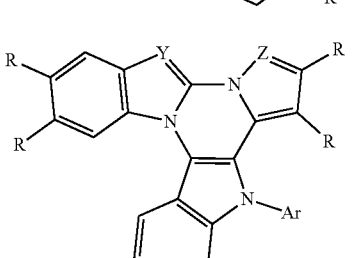
Formula (11a-1)
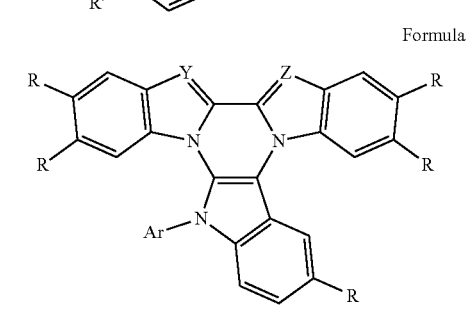
Formula (11b-1)
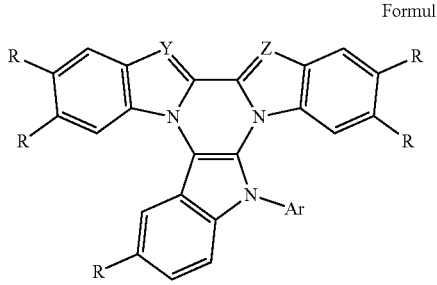
Formula (12a-1)
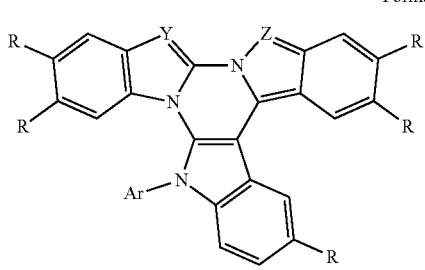
Formula (12b-1)
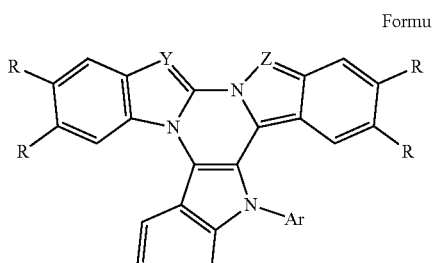
Formula (13a-1)
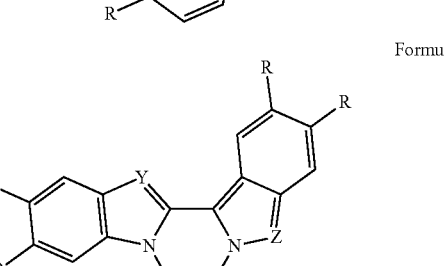
Formula (13b-1)
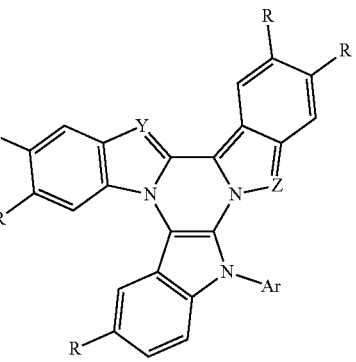

Formula (14a-1)
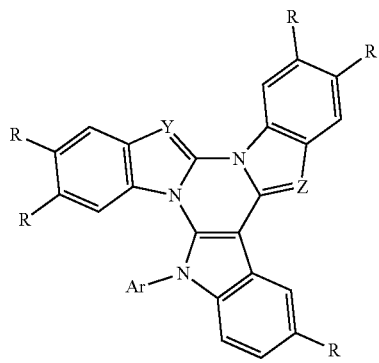
Formula (14b-1)
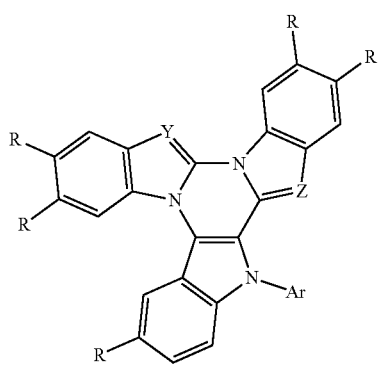
Formula (15a-1)
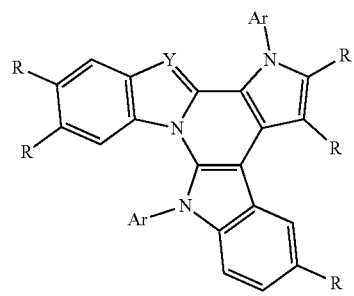
Formula (15b-1)
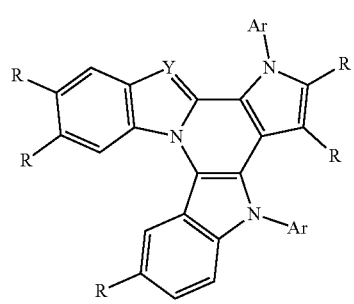
Formula (16a-1)
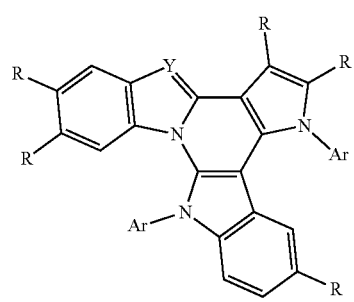
Formula (16b-1)
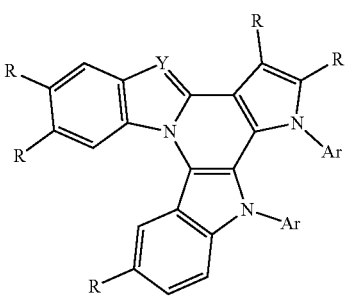
Formula (17a-1)
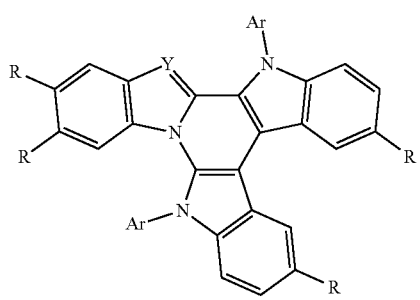
Formula (17b-1)
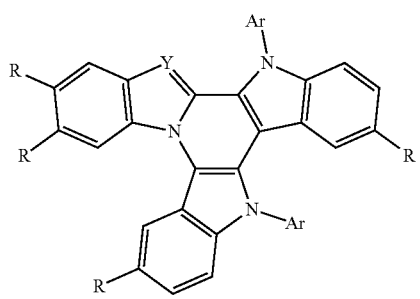
Formula (18a-1)
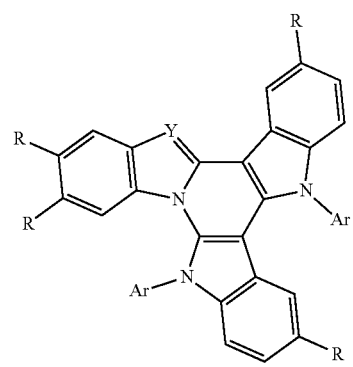

Formula (18b-1)

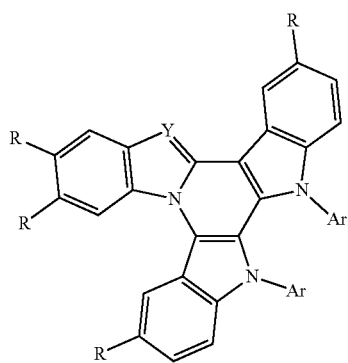

where the symbols used have the definitions given above and preferably not more than two R groups, more preferably not more than one R group, are not hydrogen.

Most preferably, the compound of the formula (1) is selected from the compounds of the following formulae (8a-2) to (18b-2):

Formula (8a-2)

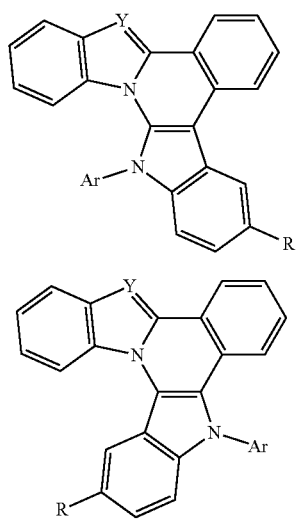

Formula (8b-2)

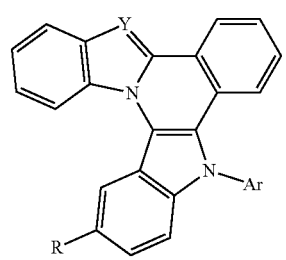

Formula (9a-2)

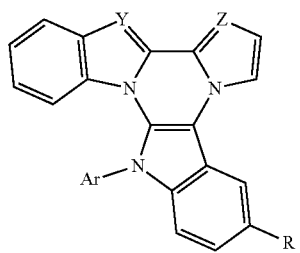

Formula (9b-2)

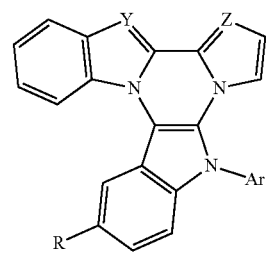

Formula (10a-2)

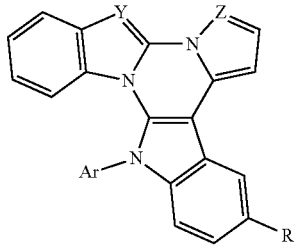

Formula (10b-2)

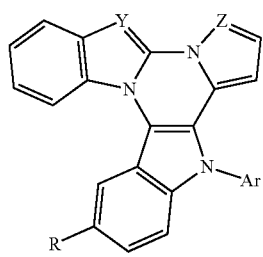

Formula (11a-2)

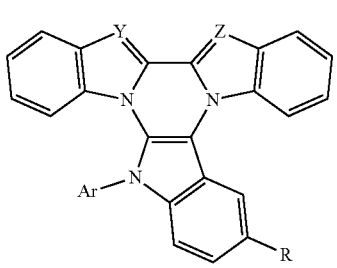

Formula (11b-2)

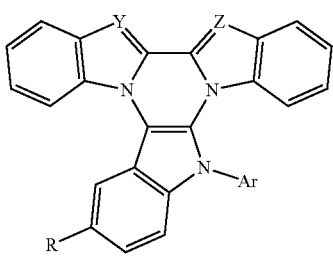

Formula (12a-2)

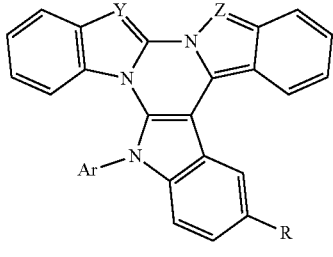

Formula (12b-2)

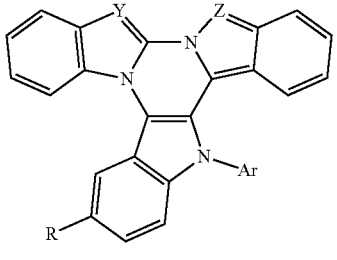

Formula (13a-2)
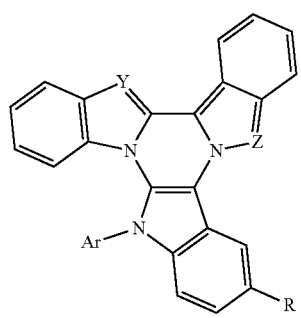
Formula (13b-2)
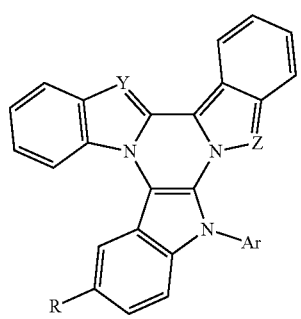
Formula (14a-2)
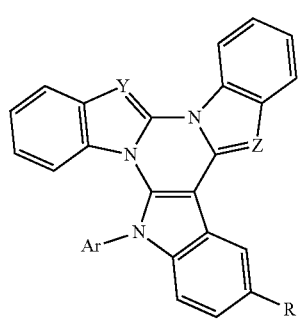
Formula (14b-2)
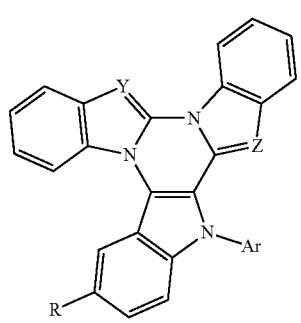
Formula (15a-2)
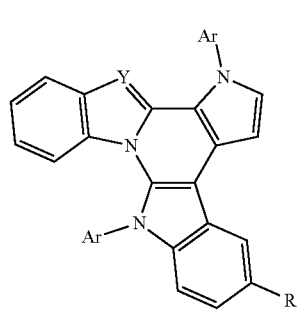
Formula (15b-2)
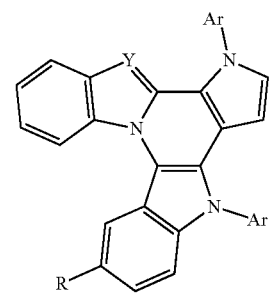
Formula (16a-2)
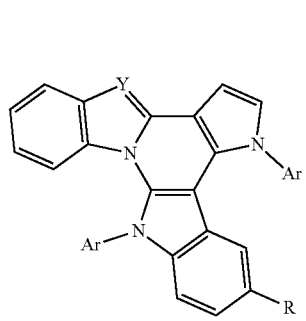
Formula (16b-2)
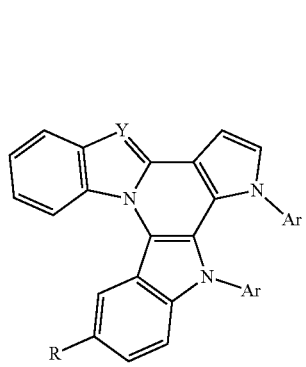
Formula (17a-2)
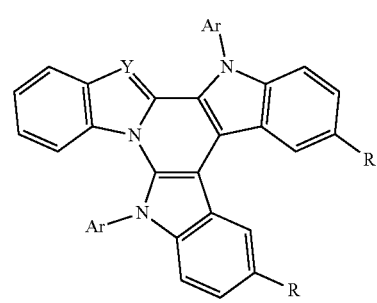
Formula (17b-2)
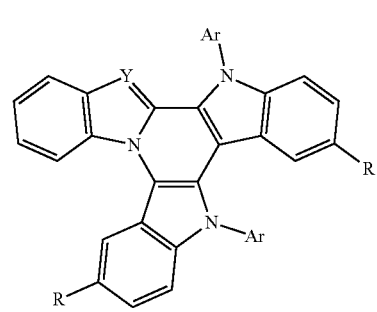

-continued

Formula (18a-2)

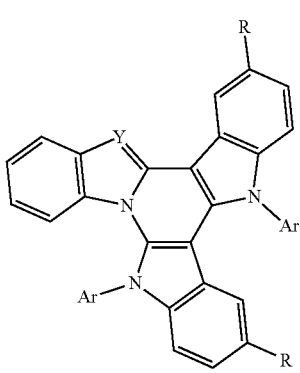

Formula (18b-2)

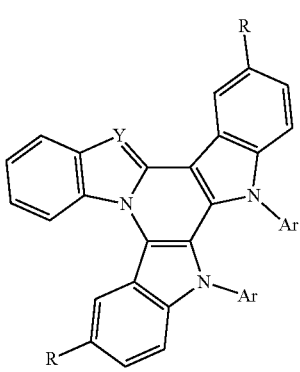

where the symbols used have the definitions given above.

In each of the abovementioned embodiments, Y may be CR or N, and Z in the formulae (9a) to (14b) may be CR or N. In a preferred embodiment, Y=N. In a further preferred embodiment, in the formulae (9a) to (14b), Z=N. More preferably, in the formulae (9a) to (14b), at the same time, Y=N and Z=N.

There follows a description of preferred substituents Ar, R, Ar', $R^1$ and $R^2$ in the compounds of the invention. In a particularly preferred embodiment of the invention, the preferences specified hereinafter for Ar, R, Ar', $R^1$ and $R^2$ occur simultaneously and are applicable to the structures of the formula (1) and also for all above-detailed preferred embodiments.

In a preferred embodiment of the invention, Ar is the same or different at each instance and is an aromatic or heteroaromatic ring system which has 6 to 30 aromatic ring atoms and may be substituted by one or more R radicals. More preferably, Ar is the same or different at each instance and is an aromatic or heteroaromatic ring system which has 6 to 24 aromatic ring atoms, especially 6 to 12 aromatic ring atoms, and may be substituted by one or more preferably nonaromatic R radicals. When Ar is a heteroaryl group, especially triazine, pyrimidine or quinazoline, preference may also be given to aromatic or heteroaromatic substituents R on this heteroaryl group. It may further be preferable when Ar is substituted by an $N(Ar)_2$ group, such that the Ar substituent constitutes a triarylamine or triheteroarylamine group overall.

Suitable aromatic or heteroaromatic ring systems Ar are the same or different at each instance and are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more R radicals, preferably nonaromatic R radicals. When Ar is a heteroaryl group, especially triazine, pyrimidine or quinazoline, preference may also be given to aromatic or heteroaromatic R radicals on this heteroaryl group.

Ar here is the same or different at each instance and is preferably selected from the groups of the following formulae Ar-1 to Ar-76:

Ar-1

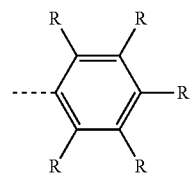

Ar-2

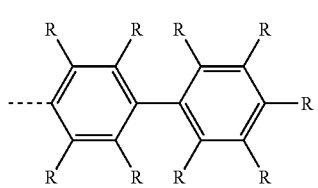

Ar-3

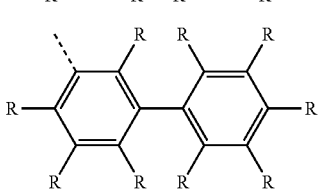

Ar-4

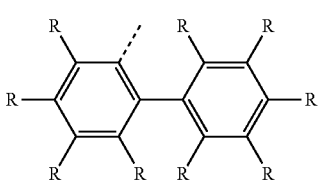

Ar-5

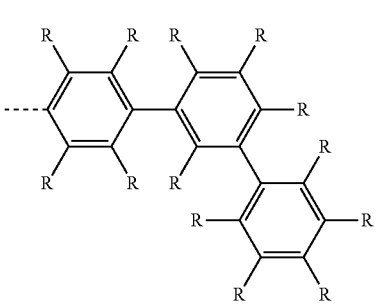

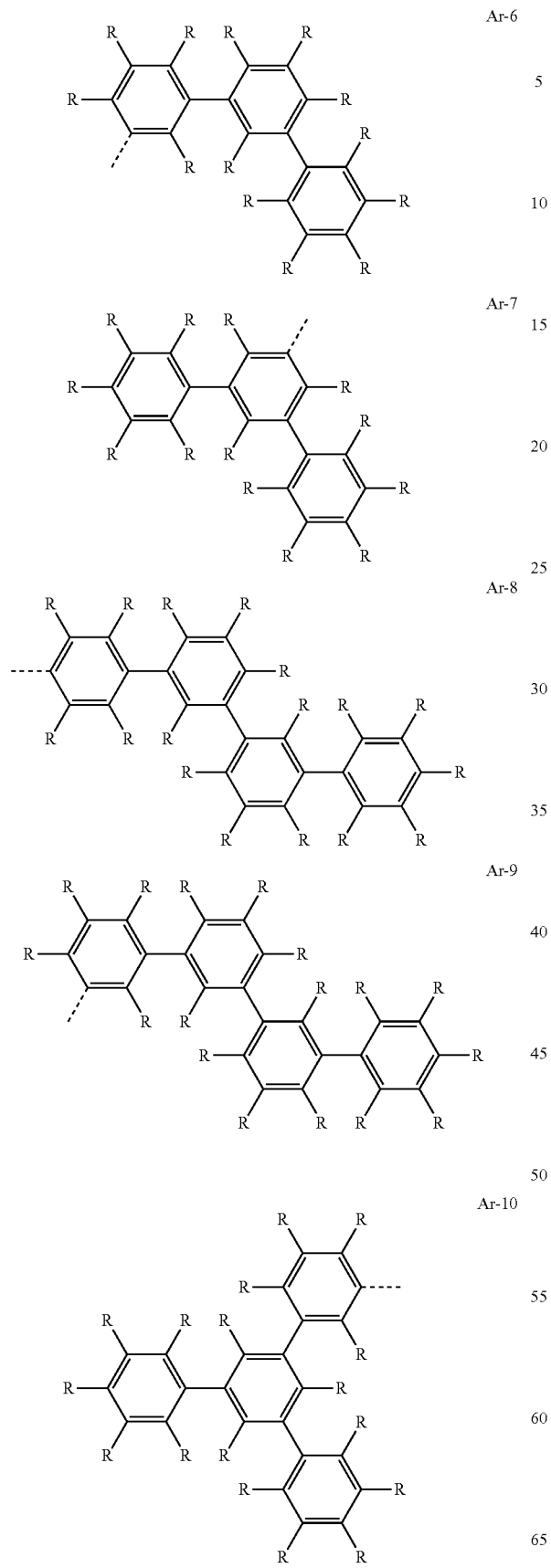

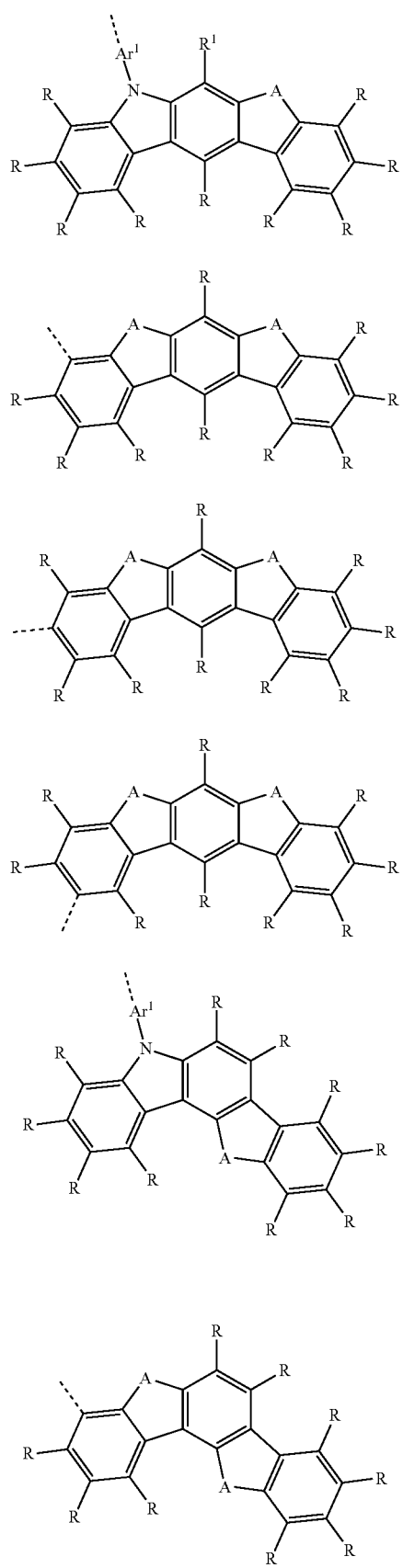
Ar-17
Ar-18
Ar-19
Ar-20
Ar-21
Ar-22
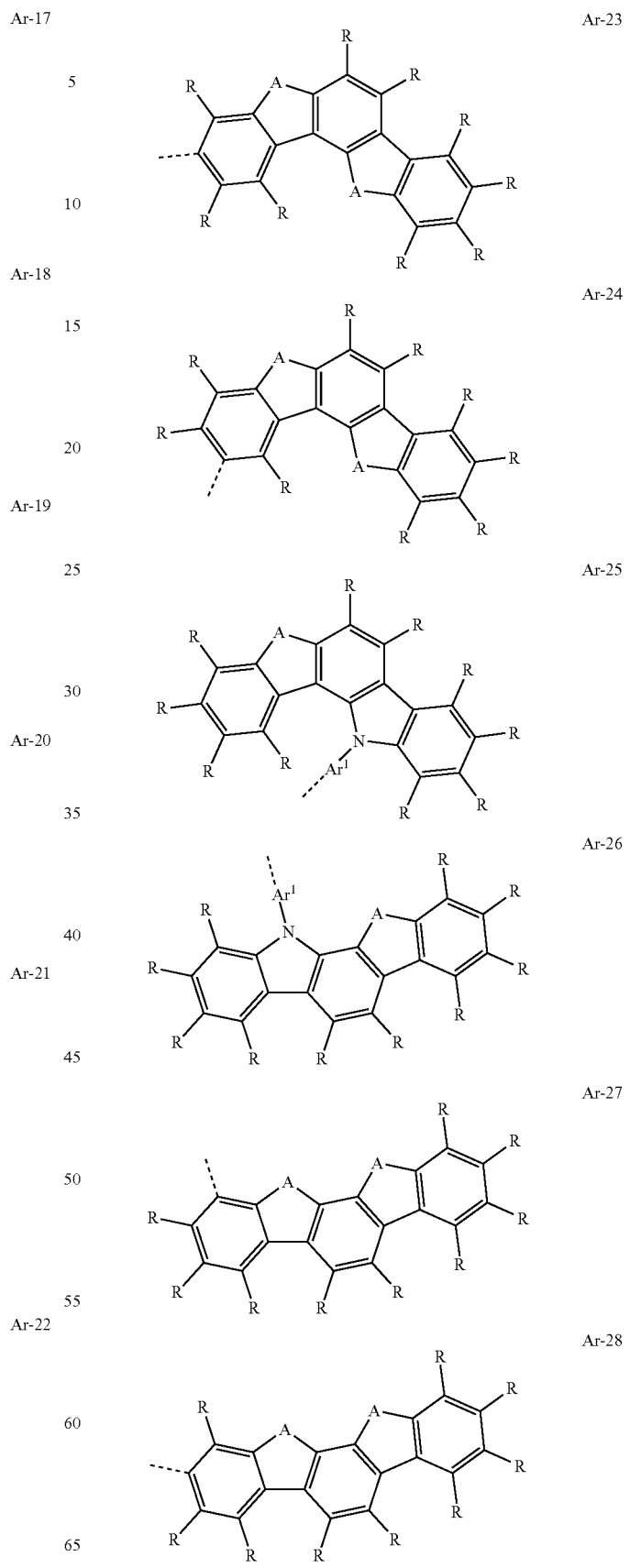
Ar-23
Ar-24
Ar-25
Ar-26
Ar-27
Ar-28

-continued
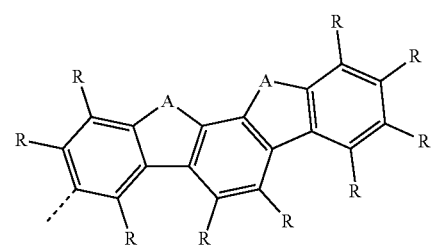
Ar-29
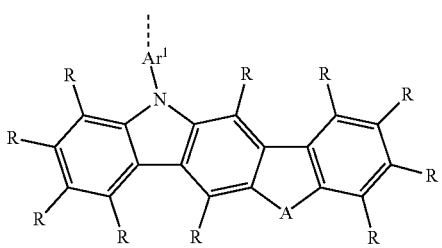
Ar-30
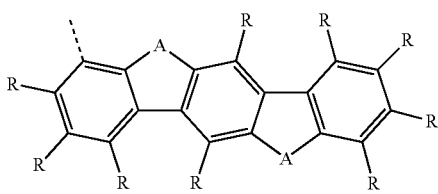
Ar-31
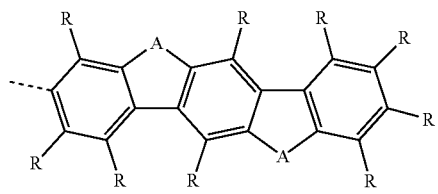
Ar-32
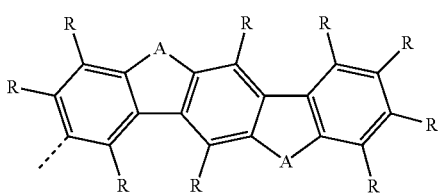
Ar-33
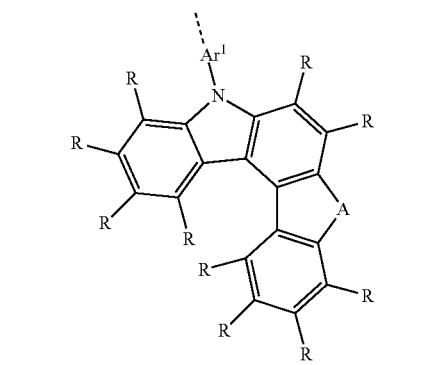
Ar-34
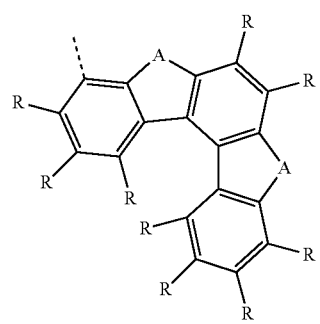
Ar-35
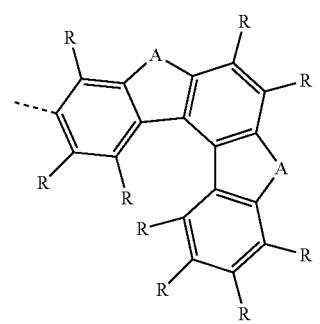
Ar-36
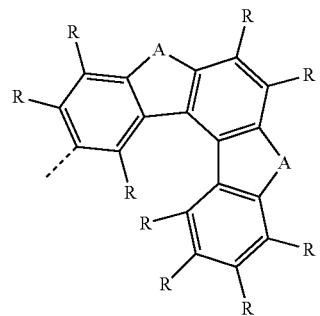
Ar-37
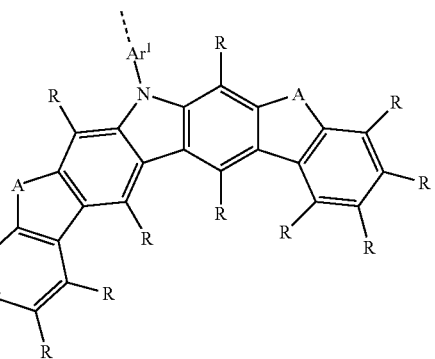
Ar-38

-continued
Ar-39
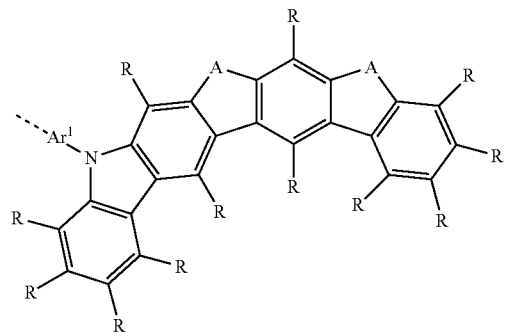
Ar-40
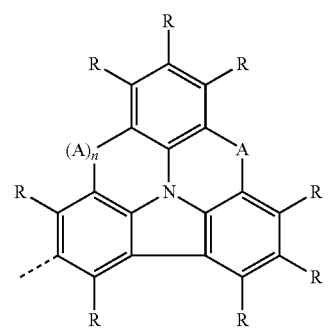
Ar-41
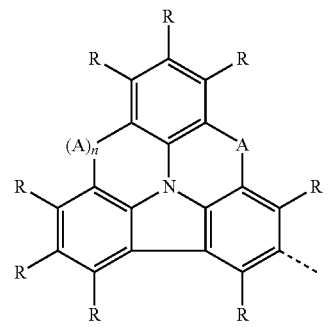
Ar-42
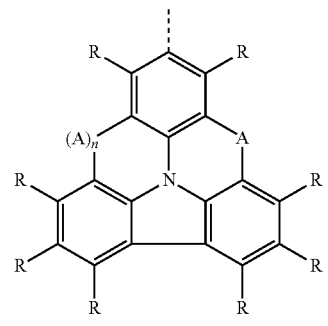
Ar-43
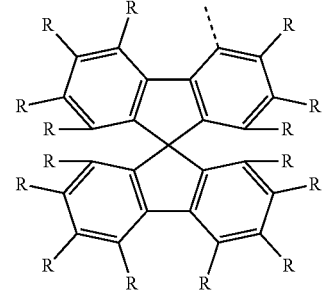
-continued
Ar-44
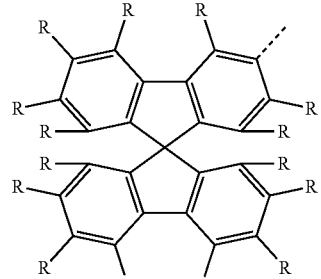
Ar-45
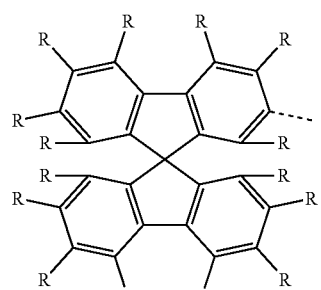
Ar-46
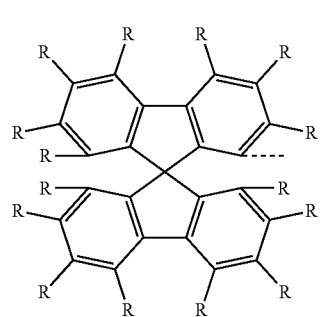
Ar-47
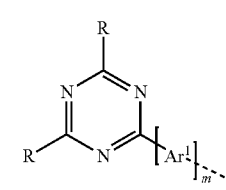
Ar-48
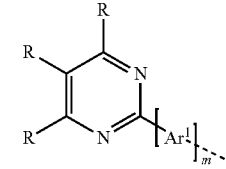
Ar-49
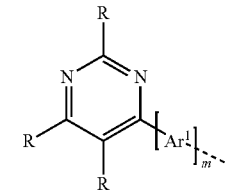
Ar-50
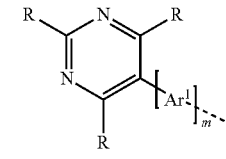

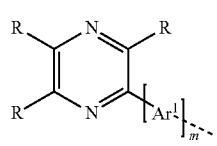
Ar-51
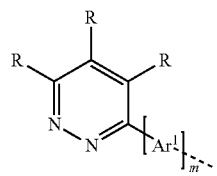
Ar-52
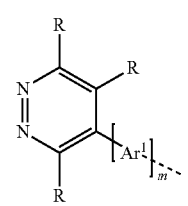
Ar-53
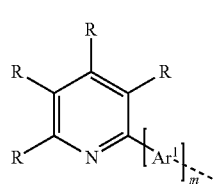
Ar-54
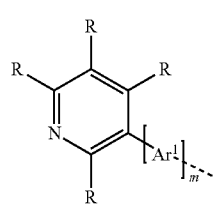
Ar-55
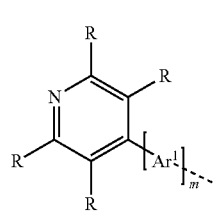
Ar-56
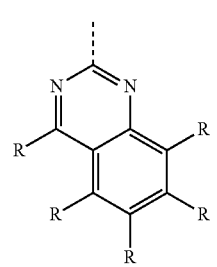
Ar-57
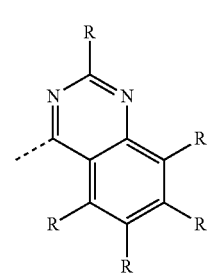
Ar-58
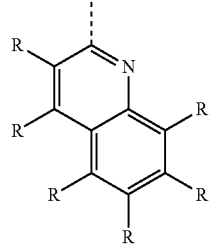
Ar-59
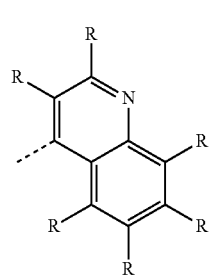
Ar-60
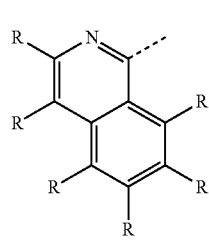
Ar-61
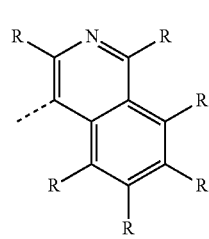
Ar-62
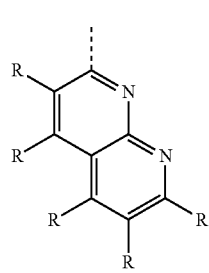
Ar-63
Ar-64

Ar-65
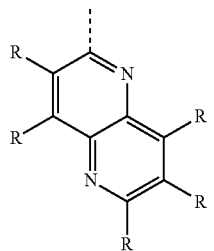
Ar-66
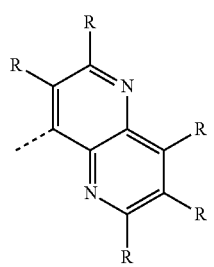
Ar-67
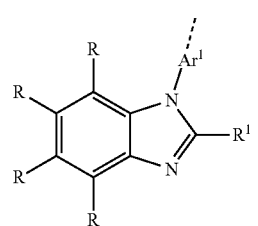
Ar-68
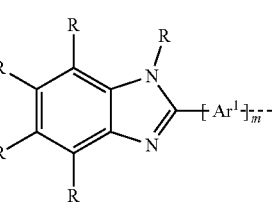
Ar-69
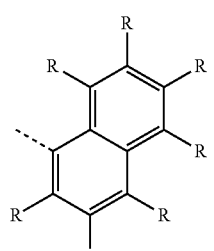
Ar-70
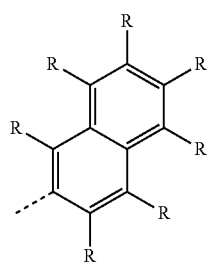
Ar-71
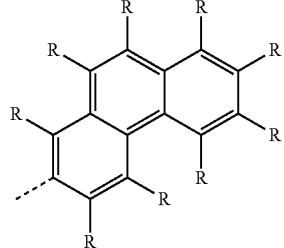
Ar-72
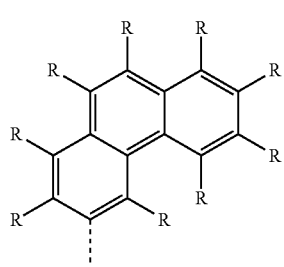
Ar-73
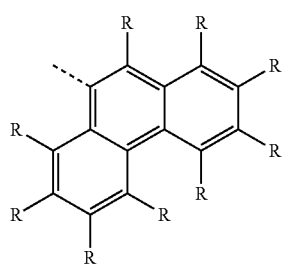
Ar-74
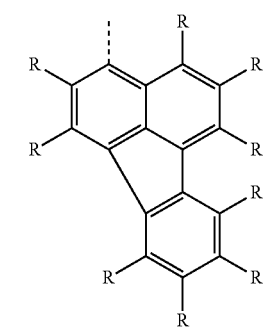
Ar-75
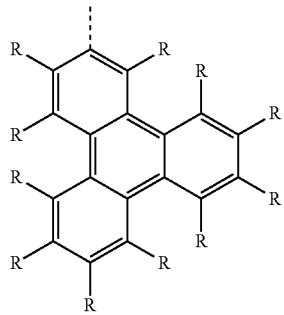

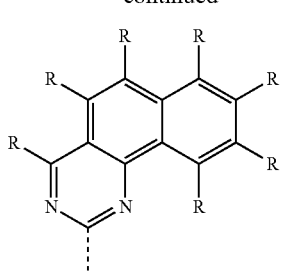

Ar-76 where R is as defined above, the dotted bond represents the bond to the nitrogen atom and, in addition:

Ar' is the same or different at each instance and is a divalent aromatic or heteroaromatic ring system which has 6 to 18 aromatic ring atoms and may be substituted in each case by one or more R radicals;

A is the same or different at each instance and is $C(R)_2$, NR, O or S;

n is 0 or 1, where n=0 means that no A group is bonded at this position and R radicals are bonded to the corresponding carbon atoms instead;

m is 0 or 1, where m=0 means that the $Ar^1$ group is absent and that the corresponding aromatic or heteroaromatic group is bonded directly to the nitrogen atom.

In a preferred embodiment of the invention, R in formula (1) is the same or different at each instance and is selected from the group consisting of H, D, F, $N(Ar')_2$, CN, $OR^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more $R^1$ radicals, but is preferably unsubstituted, and where one or more nonadjacent $CH_2$ groups may be replaced by O, or an aromatic or heteroaromatic ring system which has 6 to 30 aromatic ring atoms and may be substituted in each case by one or more $R^1$ radicals; at the same time, two R radicals together may also form a ring system, preferably an aliphatic ring system. More preferably, R is the same or different at each instance and is selected from the group consisting of H, $N(Ar')_2$, a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more $R^1$ radicals, but is preferably unsubstituted, or an aromatic or heteroaromatic ring system which has 6 to 24 aromatic ring atoms and may be substituted in each case by one or more $R^1$ radicals, preferably nonaromatic $R^1$ radicals. Most preferably, R is the same or different at each instance and is selected from the group consisting of H or an aromatic or heteroaromatic ring system which has 6 to 24 aromatic ring atoms and may be substituted in each case by one or more $R^1$ radicals, preferably nonaromatic $R^1$ radicals. It may additionally be preferable when R is a triaryl- or -heteroarylamine group which may be substituted by one or more $R^1$ radicals. This group is one embodiment of an aromatic or heteroaromatic ring system, in which case two or more aryl or heteroaryl groups are joined to one another by a nitrogen atom. When R is a triaryl- or -heteroarylamine group, this group preferably has 18 to 30 aromatic ring atoms and may be substituted by one or more $R^1$ radicals, preferably nonaromatic $R^1$ radicals.

In a further preferred embodiment of the invention, Ar' is an aromatic or heteroaromatic ring system which has 6 to 30 aromatic ring atoms and may be substituted by one or more $R^1$ radicals. In a particularly preferred embodiment of the invention, Ar' is an aromatic or heteroaromatic ring system which has 6 to 24 aromatic ring atoms, especially 6 to 13 aromatic ring atoms, and may be substituted by one or more preferably nonaromatic $R^1$ radicals.

In a further preferred embodiment of the invention, $R^1$ is the same or different at each instance and is selected from the group consisting of H, D, F, CN, $OR^2$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more $R^2$ radicals, and where one or more nonadjacent $CH_2$ groups may be replaced by O, or an aromatic or heteroaromatic ring system which has 6 to 30 aromatic ring atoms and may be substituted in each case by one or more $R^2$ radicals; at the same time, two or more $R^1$ radicals together may form an aliphatic ring system. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 24 aromatic ring atoms and may be substituted in each case by one or more $R^2$ radicals, but is preferably unsubstituted.

In a further preferred embodiment of the invention, $R^2$ is the same or different at each instance and is H, F, an alkyl group having 1 to 4 carbon atoms or an aryl group having 6 to 10 carbon atoms, which may be substituted by an alkyl group having 1 to 4 carbon atoms, but is preferably unsubstituted.

Suitable aromatic or heteroaromatic ring systems R or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene, especially 1- or 2-bonded naphthalene, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more $R^1$ radicals. When R or Ar' is a heteroaryl group, especially triazine, pyrimidine or quinazoline, preference may also be given to aromatic or heteroaromatic $R^1$ radicals on this heteroaryl group.

The R groups, when they are an aromatic or heteroaromatic ring system, or Ar' groups here are preferably selected from the groups of the following formulae R-1 to R-76:

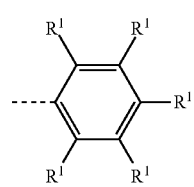

R-1

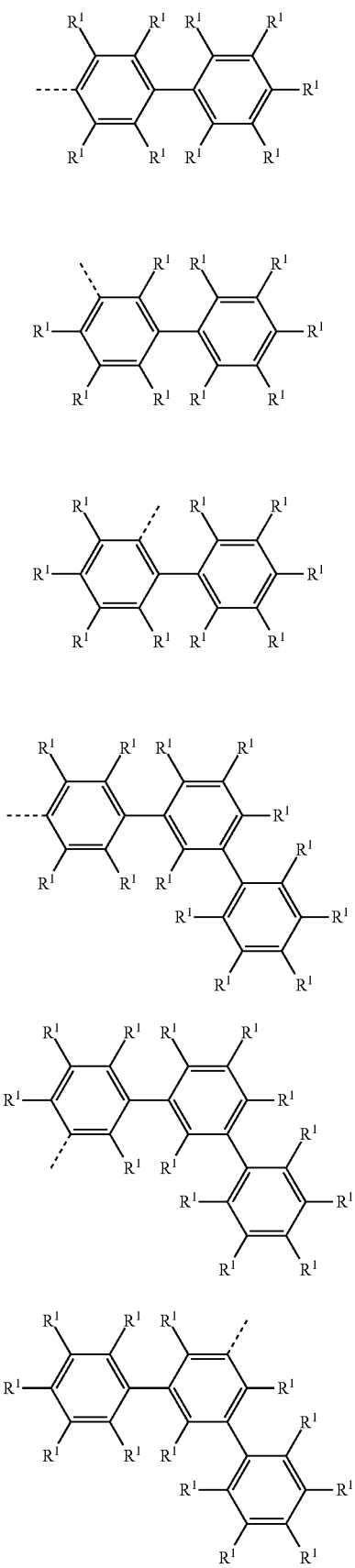
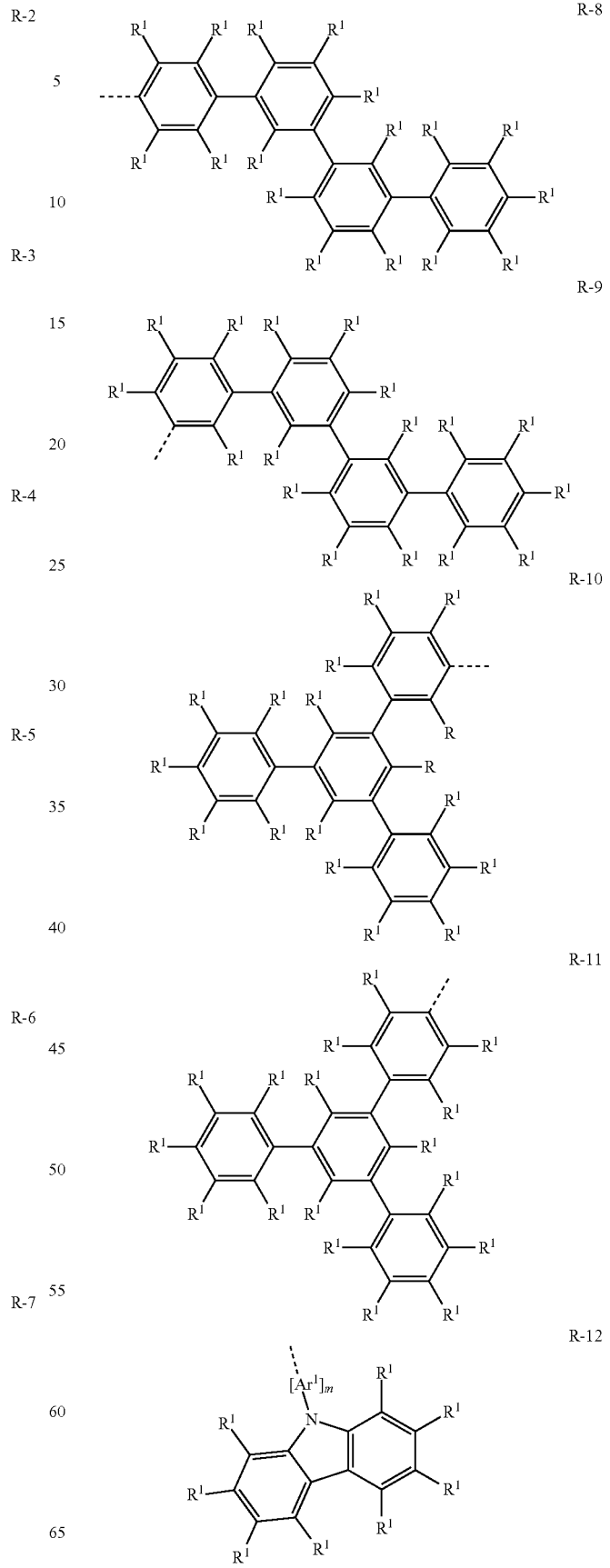

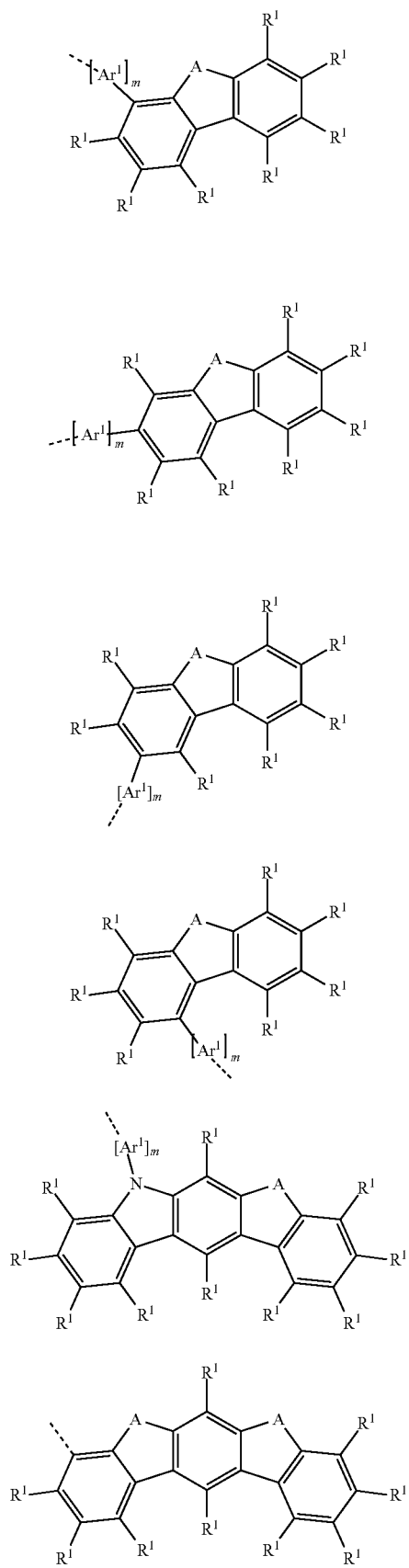
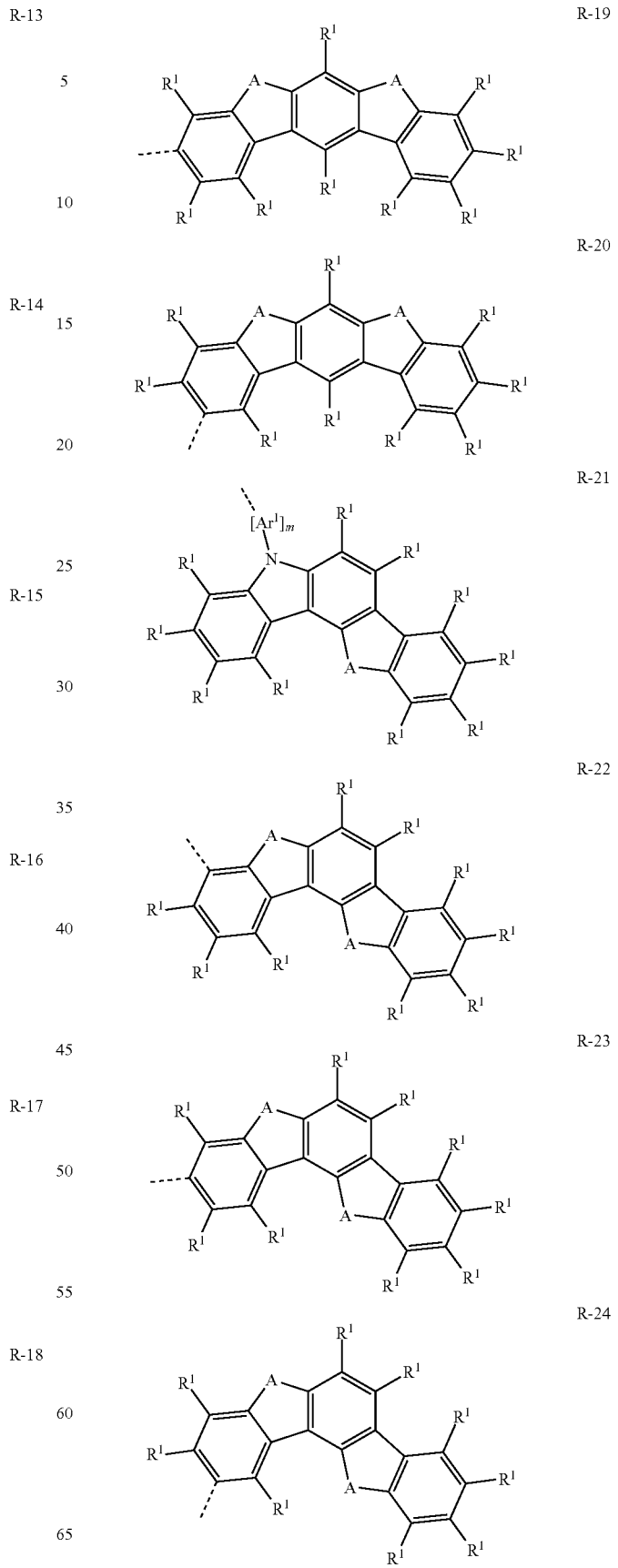

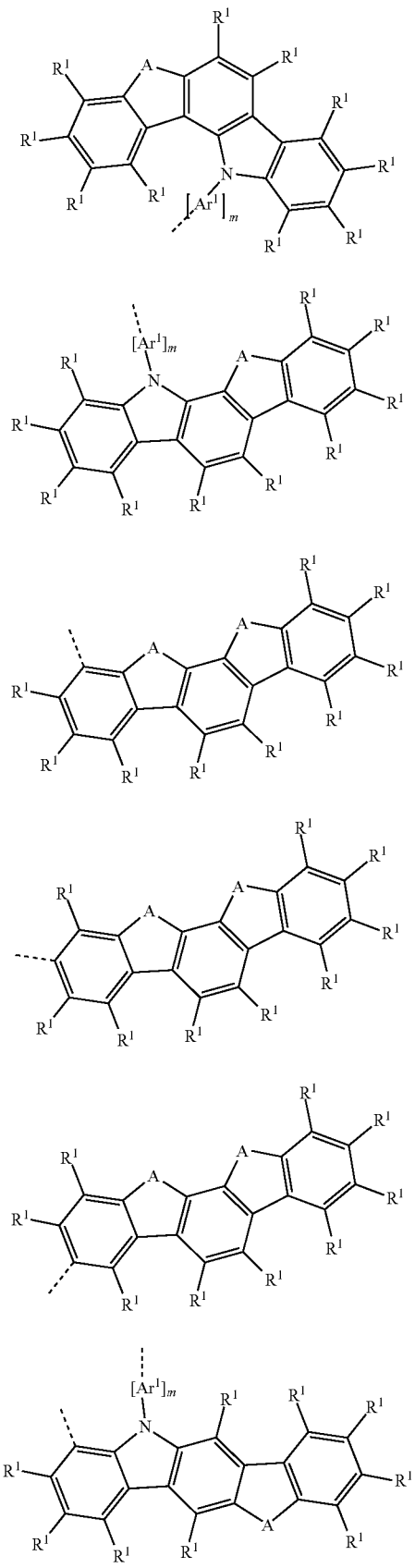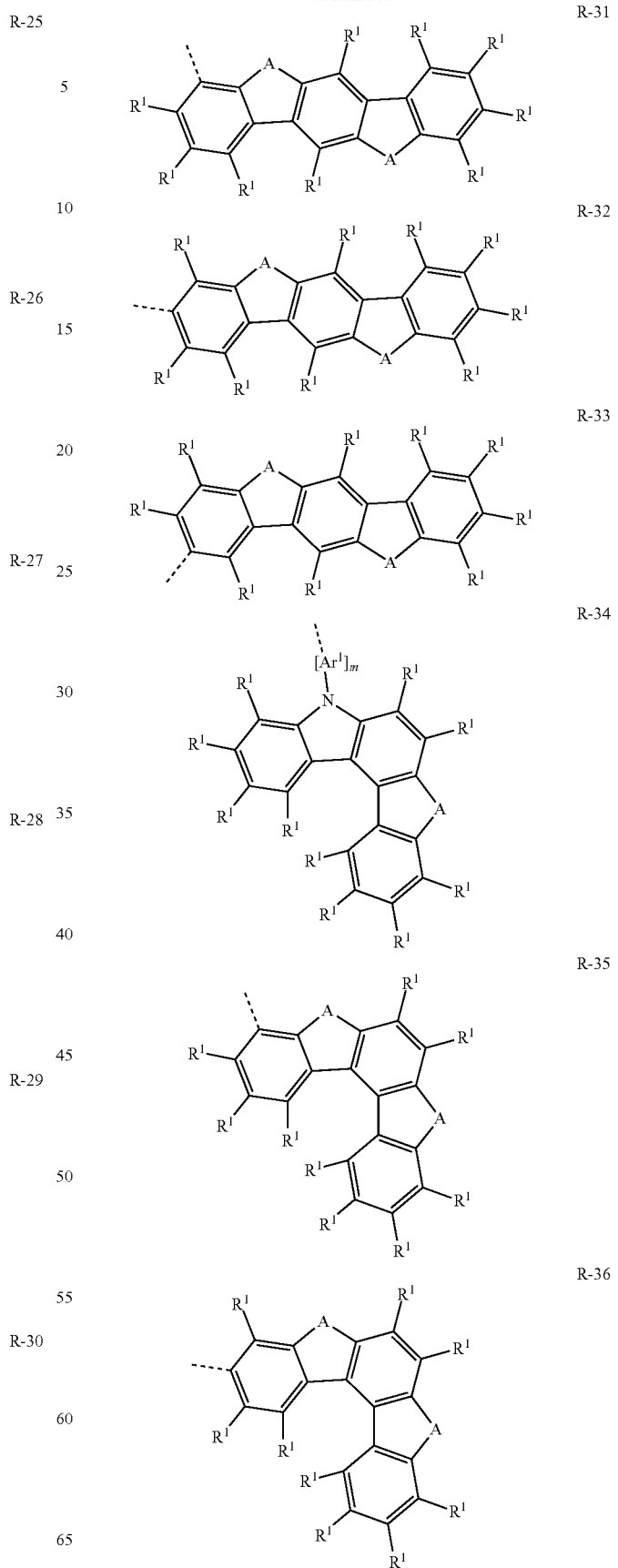

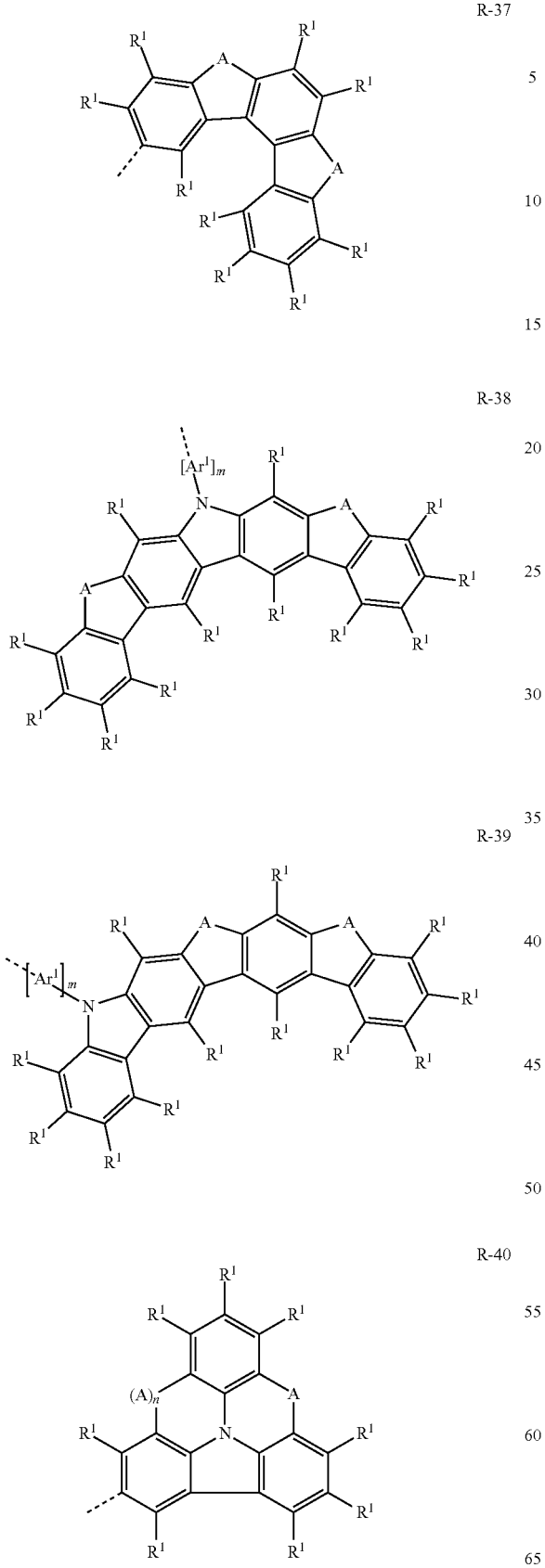
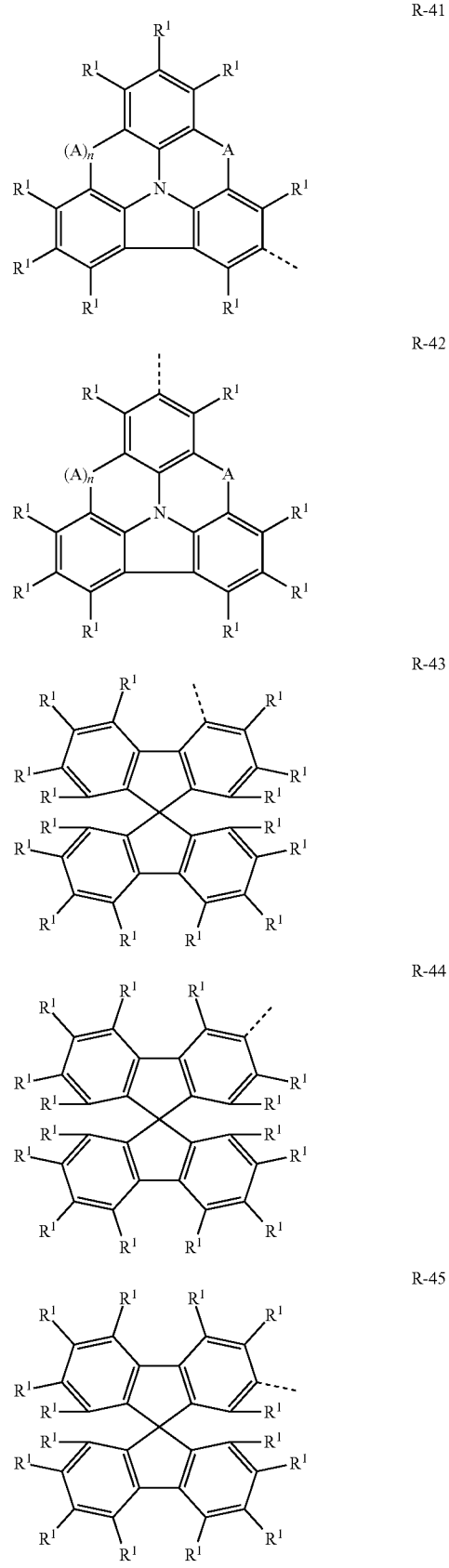

R-46
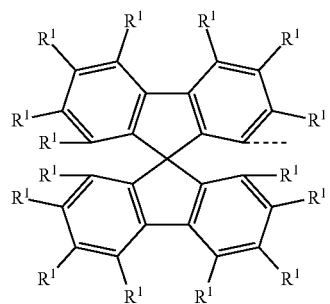
R-47
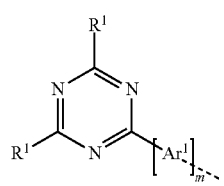
R-48
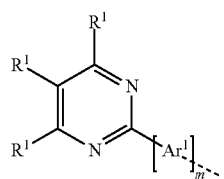
R-49
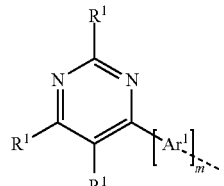
R-50
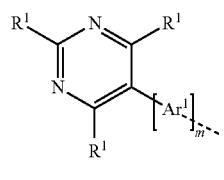
R-51
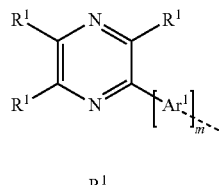
R-52
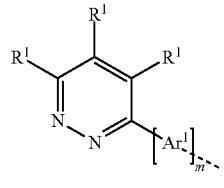
R-53
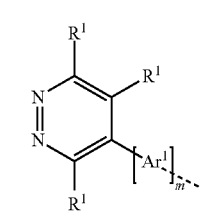
R-54
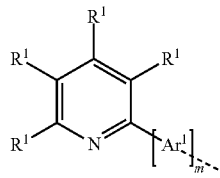
R-55
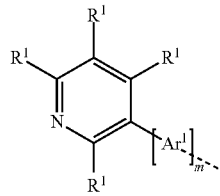
R-56
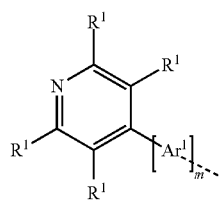
R-57
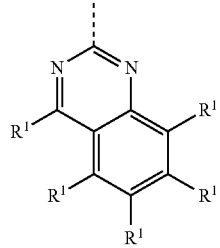
R-58
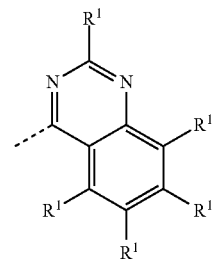
R-59
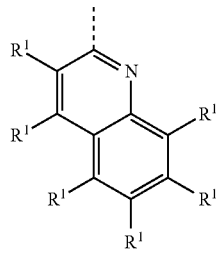

-continued
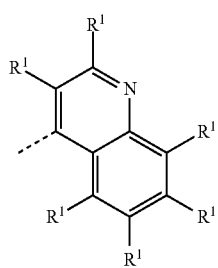
R-60
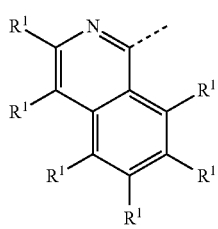
R-61
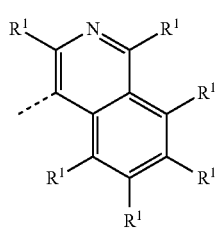
R-62
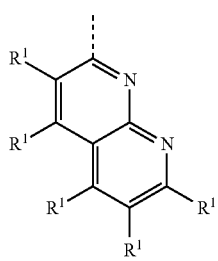
R-63
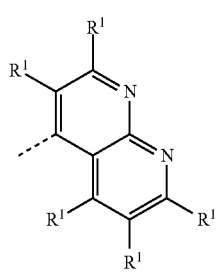
R-64
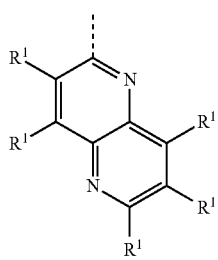
R-65
-continued
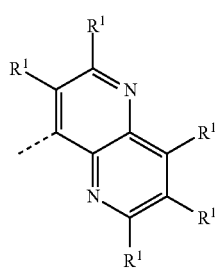
R-66
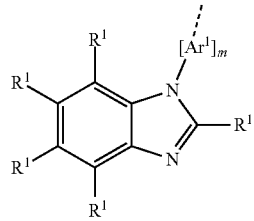
R-67
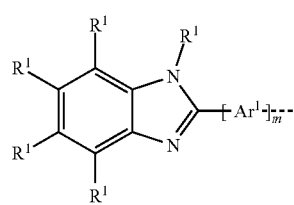
R-68
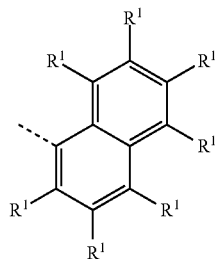
R-69
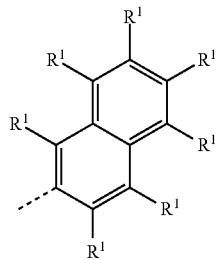
R-70
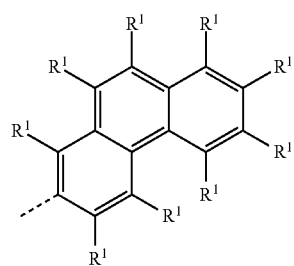
R-71

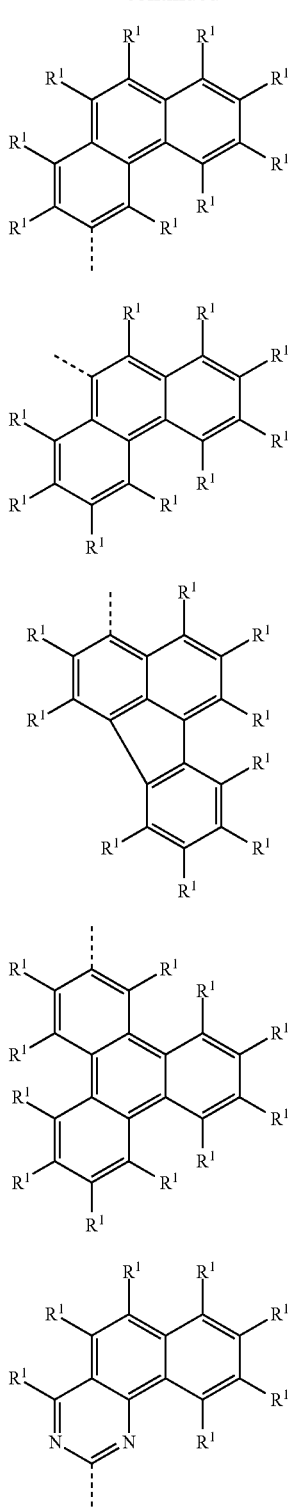

where R¹ has the definitions given above, the dotted bond represents the bond to a carbon atom of the base skeleton in formula (1) or in the preferred embodiments or to the nitrogen atom in the N(Ar')₂ group and, in addition:
Ar¹ is the same or different at each instance and is a bivalent aromatic or heteroaromatic ring system which has 6 to 18 aromatic ring atoms and may be substituted in each case by one or more R¹ radicals;

A is the same or different at each instance and is C(R¹)₂, NR¹, O or S;
n is 0 or 1, where n=0 means that no A group is bonded at this position and R¹ radicals are bonded to the corresponding carbon atoms instead;
m is 0 or 1, where m=0 means that the Ar¹ group is absent and that the corresponding aromatic or heteroaromatic group is bonded directly to a carbon atom of the base skeleton in formula (1) or in the preferred embodiments, or to the nitrogen atom in the N(Ar')₂ group; with the proviso that m=1 for the structures (R-12), (R-17), (R-21), (R-25), (R-26), (R-30), (R-34), (R-38) and (R-39) when these groups are embodiments of Ar'.

When the abovementioned Ar-1 to Ar-76 groups for Ar or R-1 to R-76 groups for R or Ar' have two or more A groups, possible options for these include all combinations from the definition of A. Preferred embodiments in that case are those in which one A group is NR or NR¹ and the other A group is C(R)₂ or C(R¹)₂ or in which both A groups are NR or NR¹ or in which both A groups are O. In a particularly preferred embodiment of the invention, in Ar, R or Ar' groups having two or more A groups, at least one A group is C(R)₂ or C(R¹)₂ or is NR or NR¹.

When A is NR or NR¹, the substituent R or R¹ bonded to the nitrogen atom is preferably an aromatic or heteroaromatic ring system which has 5 to 24 aromatic ring atoms and may also be substituted by one or more R¹ or R² radicals. In a particularly preferred embodiment, this R or R¹ substituent is the same or different at each instance and is an aromatic or heteroaromatic ring system which has 6 to 24 aromatic ring atoms, preferably 6 to 12 aromatic ring atoms, and which does not have any fused aryl groups or heteroaryl groups in which two or more aromatic or heteroaromatic 6-membered ring groups are fused directly to one another, and which may also be substituted in each case by one or more R¹ or R² radicals. Particular preference is given to phenyl, biphenyl, terphenyl and quaterphenyl having bonding patterns as listed above for Ar-1 to Ar-11 or R-1 to R-11, where these structures may be substituted by one or more R¹ or R² radicals, but are preferably unsubstituted.

When A is C(R)₂ or C(R¹)₂, the substituents R or R¹ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system which has 5 to 24 aromatic ring atoms and may also be substituted by one or more R¹ or R² radicals. Most preferably, R or R¹ is a methyl group or a phenyl group. In this case, the R or R¹ radicals together may also form a ring system, which leads to a spiro system.

Further suitable Ar, R or Ar' groups are groups of the formula —Ar⁴—N(Ar²)(Ar³) where Ar², Ar³ and Ar⁴ are the same or different at each instance and are an aromatic or heteroaromatic ring system which has 5 to 24 aromatic ring atoms and may be substituted in each case by one or more R¹ radicals. Ar results in such a group when the Ar group is substituted by an N(Ar')₂ group. The total number of aromatic ring atoms in Ar², Ar³ and Ar⁴ here is not more than 60 and preferably not more than 40.

In this case, Ar⁴ and Ar² may also be bonded to one another and/or Ar² and Ar³ to one another via a group selected from C(R¹)₂, NR¹, O and S. Preferably, Ar⁴ and Ar² are joined to one another and Ar² and Ar³ to one another in the respective ortho position to the bond to the nitrogen atom. In a further embodiment of the invention, none of the Ar², Ar³ and Ar⁴ groups are bonded to one another.

Preferably, Ar⁴ is an aromatic or heteroaromatic ring system which has 6 to 24 aromatic ring atoms, especially 6 to 12 aromatic ring atoms, and may be substituted in each case by one or more R¹ radicals. More preferably, Ar⁴ is selected from the group consisting of ortho-, meta- or para-phenylene or ortho-, meta- or para-biphenyl, each of which may be substituted by one or more R¹ radicals, but are preferably unsubstituted. Most preferably, Ar⁴ is an unsubstituted phenylene group. This is the case particularly when Ar⁴ is joined to Ar² by a single bond.

Preferably, Ar² and Ar³ are the same or different at each instance and are an aromatic or heteroaromatic ring system which has 6 to 24 aromatic ring atoms and may be substituted in each case by one or more R¹ radicals. Particularly preferred Ar² and Ar³ groups are the same or different at each instance and are selected from the group consisting of benzene, ortho-, meta- or para-biphenyl, ortho-, meta- or para-terphenyl or branched terphenyl, ortho-, meta- or para-quaterphenyl or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene, triphenylene or combinations of two, three or four of these groups, each of which may be substituted by one or more R¹ radicals. More preferably, Ar² and Ar³ are the same or different at each instance and are an aromatic ring system which has 6 to 24 aromatic ring atoms and may be substituted by one or more R¹ radicals, especially selected from the groups consisting of benzene, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene, especially 1-, 2-, 3- or 4-fluorene, or spirobifluorene, especially 1-, 2-, 3- or 4-spirobifluorene.

At the same time, the alkyl groups in compounds of the invention which are processed by vacuum evaporation preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta-, para- or branched terphenyl or quaterphenyl groups.

When the compounds of the formula (1) or the preferred embodiments are used as matrix material for a phosphorescent emitter or in a layer directly adjoining a phosphorescent layer, it is further preferable when the compound does not contain any fused aryl or heteroaryl groups in which more than two six-membered rings are fused directly to one another. It is especially preferable when the Ar, R, Ar', R¹ and R² radicals do not contain any fused aryl or heteroaryl groups in which two or more six-membered rings are fused directly to one another. An exception to this is formed by phenanthrene and triphenylene which, because of their high triplet energy, may be preferable in spite of the presence of fused aromatic six-membered rings.

The abovementioned preferred embodiments may be combined with one another as desired within the restrictions defined in claim 1. In a particularly preferred embodiment of the invention, the abovementioned preferences occur simultaneously.

Examples of preferred compounds according to the embodiments detailed above are the compounds detailed in the following table:

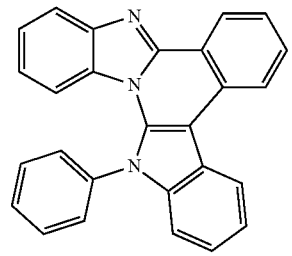 [SMILES: c1ccc(-n2c3ccccc3c3c4ccccc4c4nc5ccccc5n4c32)cc1]

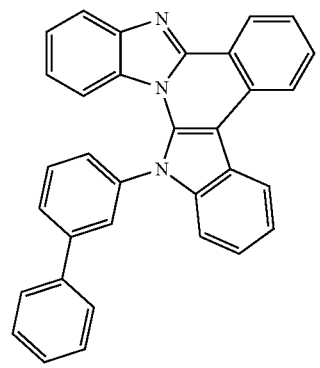 [SMILES: c1ccc(-c2cccc(-n3c4ccccc4c4c5ccccc5c5nc6ccccc6n5c43)c2)cc1]

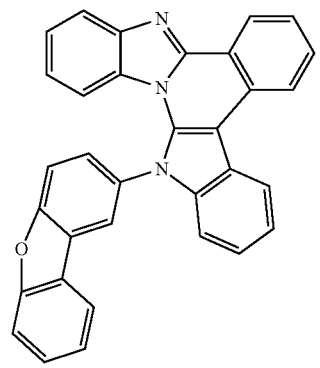 [SMILES: c1ccc2c(c1)nc1c3ccccc3c3c4ccccc4n(-c4ccc5oc6ccccc6c5c4)c3n21]

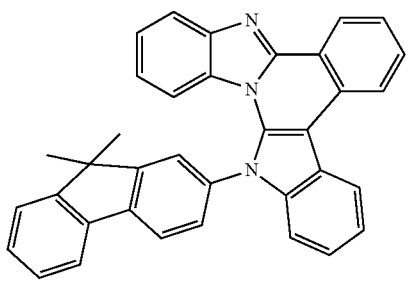 [SMILES: CC1(C)c2ccccc2-c2ccc(-n3c4ccccc4c4c5ccccc5c5nc6ccccc6n5c43)cc21]

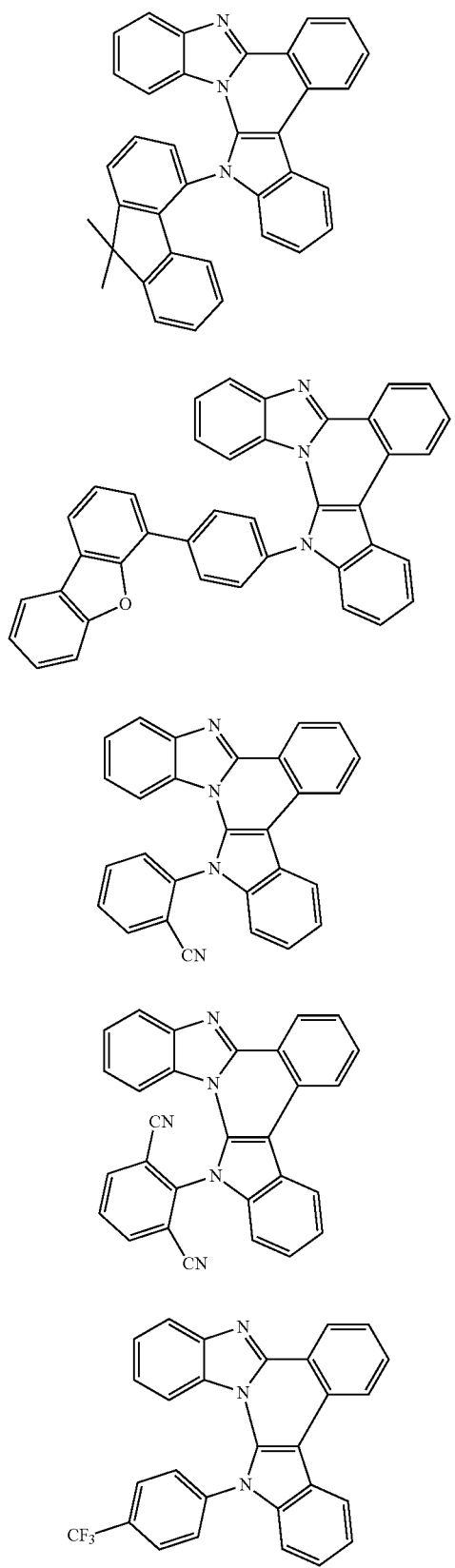
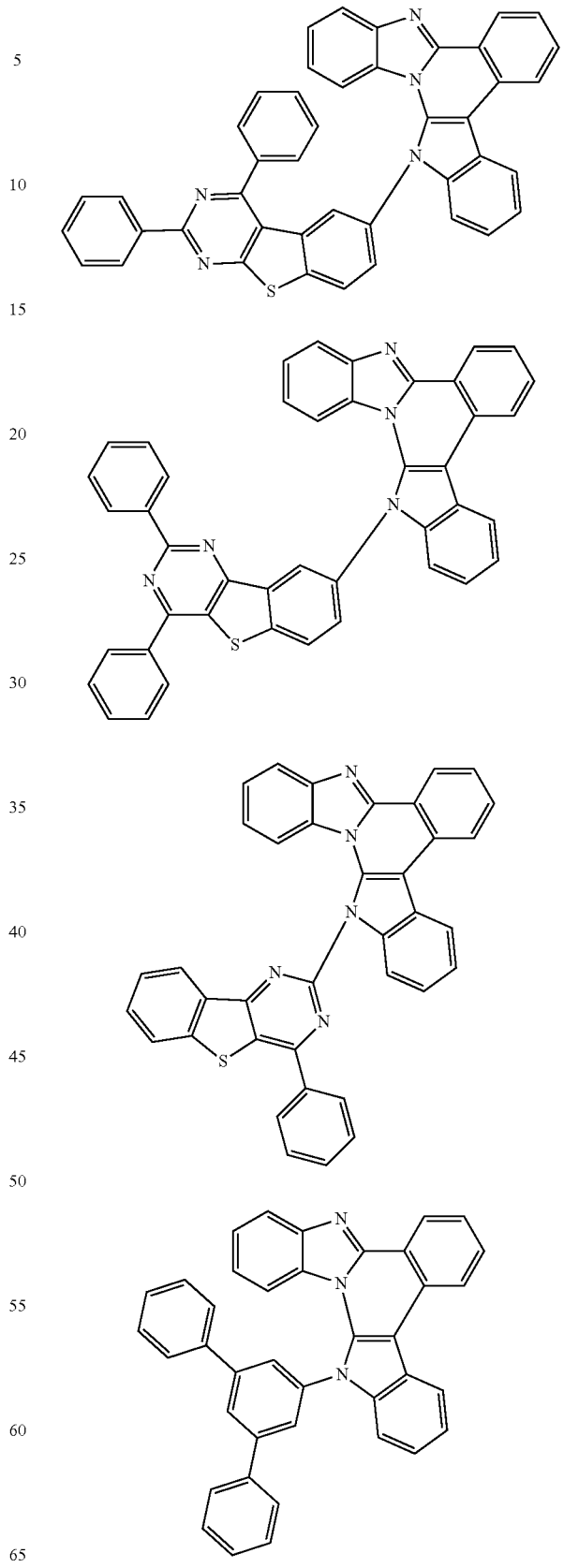

57
-continued
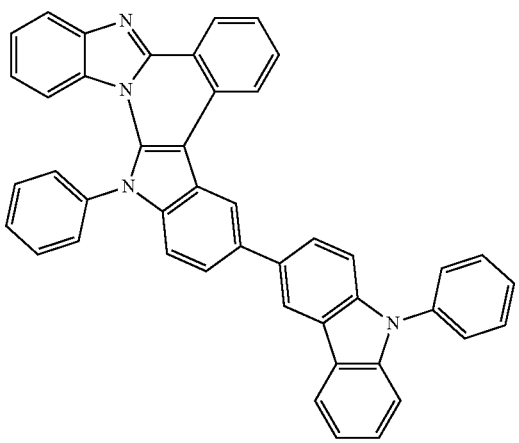 [SMILES: c1ccc(-n2c3ccccc3c3cc(-c4ccc5c(c4)c4c6ccccc6c6nc7ccccc7n6c4n5-c4ccccc4)ccc32)cc1]
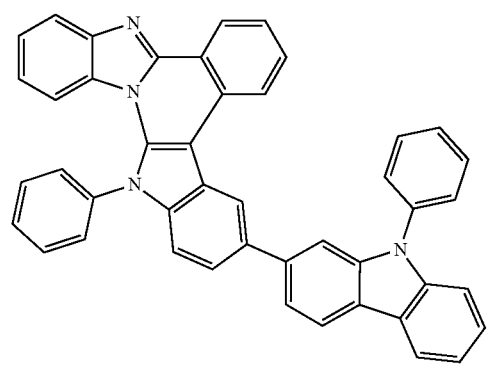 [SMILES: c1ccc(-n2c3ccccc3c3ccc(-c4ccc5c(c4)c4c6ccccc6c6nc7ccccc7n6c4n5-c4ccccc4)cc32)cc1]
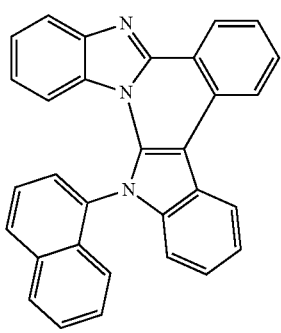 [SMILES: c1ccc2c(-n3c4ccccc4c4c5ccccc5c5nc6ccccc6n5c43)cccc2c1]
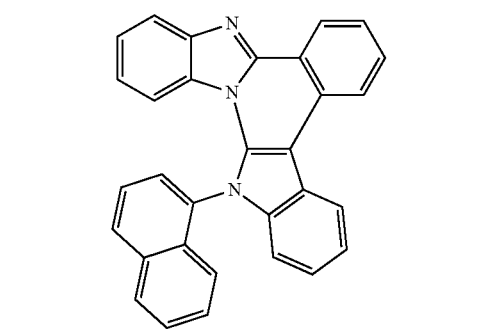
58
-continued
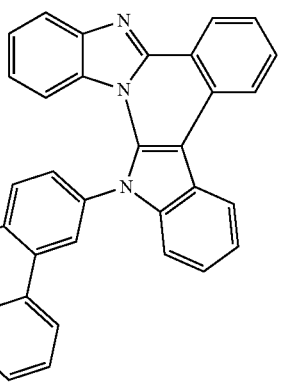
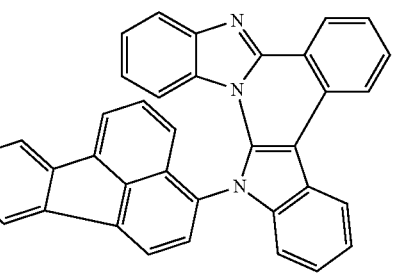
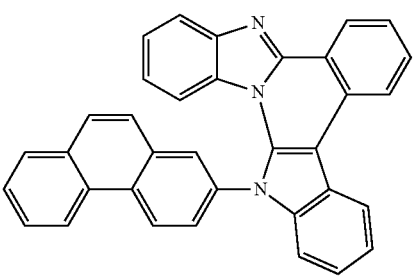 [SMILES: c1ccc2c(c1)ccc1cc(-n3c4ccccc4c4c5ccccc5c5nc6ccccc6n5c43)ccc12]
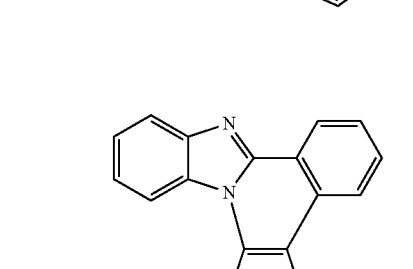
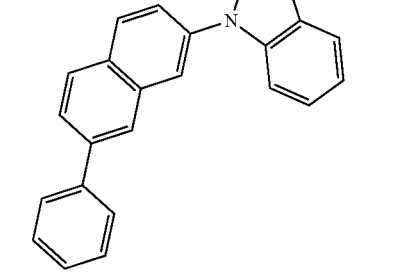

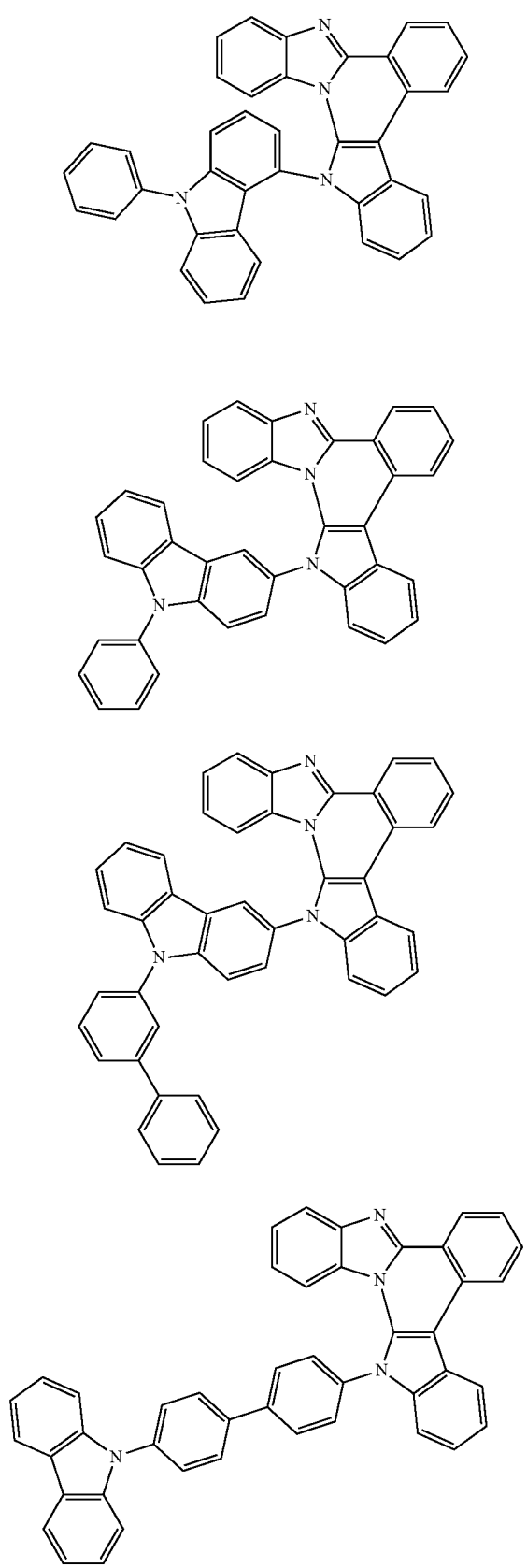
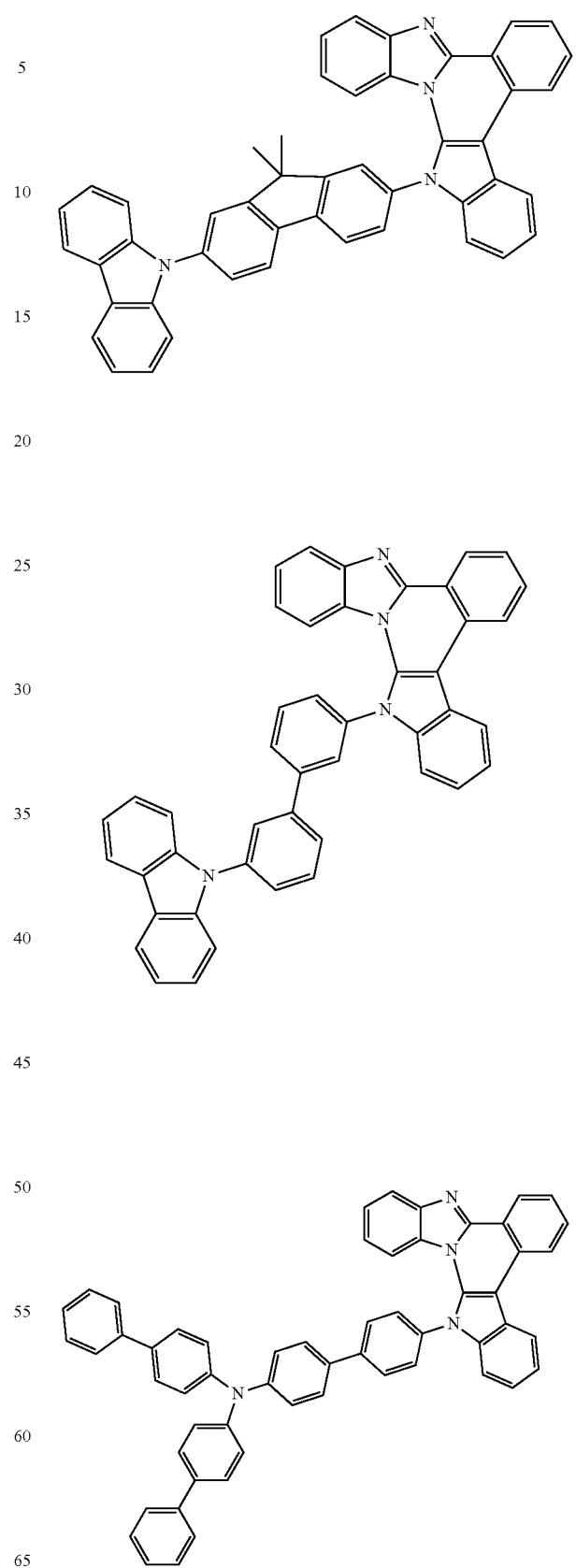

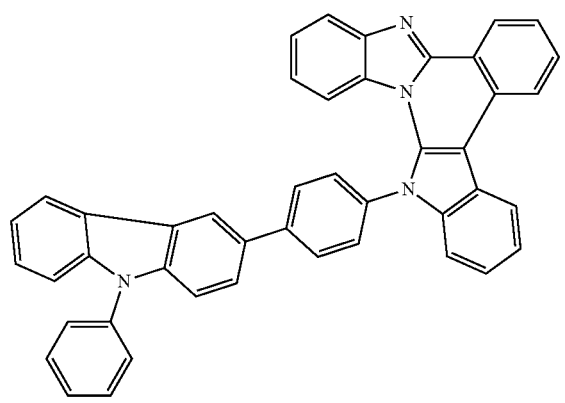 [SMILES: c1ccc(-n2c3ccccc3c3cc(-c4ccc(-n5c6ccccc6c6c7ccccc7c7nc8ccccc8n7c65)cc4)ccc32)cc1]
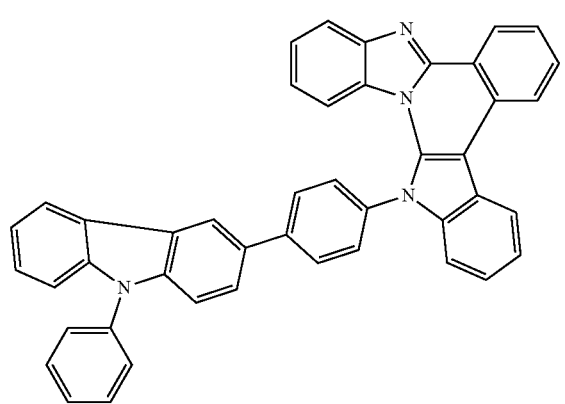 [SMILES: c1ccc(-n2c3ccccc3c3cc(-c4ccc(-n5c6ccccc6c6c7ccccc7c7nc8ccccc8n7c65)cc4)ccc32)cc1]
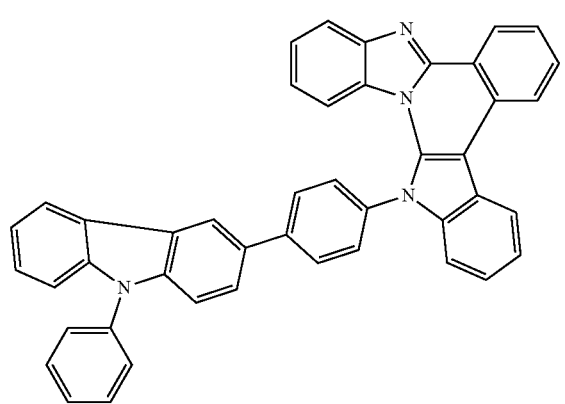 [SMILES: c1ccc(-n2c3ccccc3c3cc(-c4ccc(-n5c6ccccc6c6c7ccccc7c7nc8ccccc8n7c65)cc4)ccc32)cc1]
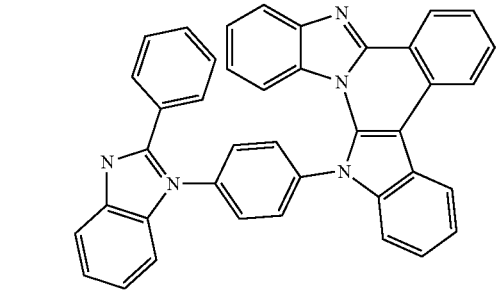
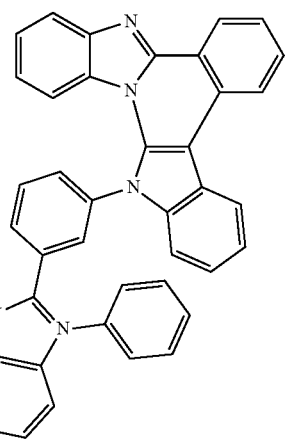
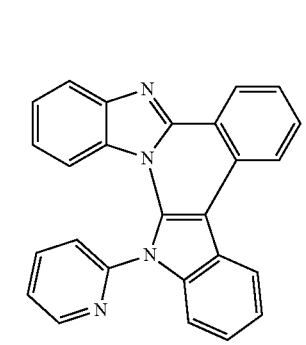 [SMILES: c1ccc(-n2c3ccccc3c3c4ccccc4c4nc5ccccc5n4c32)nc1]
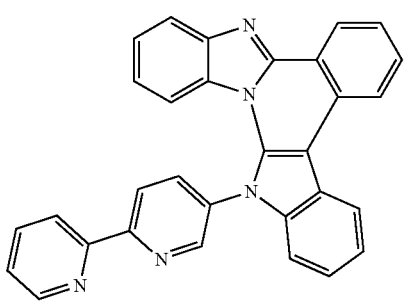 [SMILES: c1ccc(-c2ccc(-n3c4ccccc4c4c5ccccc5c5nc6ccccc6n5c43)cn2)nc1]
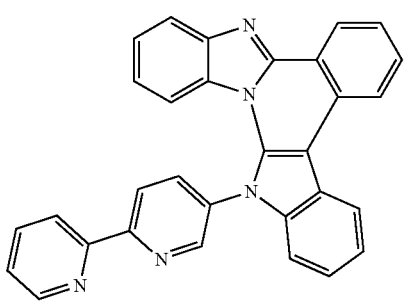 [SMILES: c1ccc(-c2ccc(-n3c4ccccc4c4c5ccccc5c5nc6ccccc6n5c43)cn2)nc1]

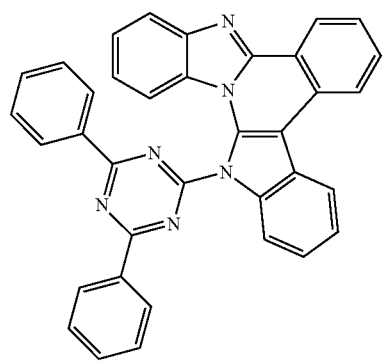 [SMILES: c1ccc(-c2nc(-c3ccccc3)nc(-n3c4ccccc4c4c5ccccc5c5nc6ccccc6n5c43)n2)cc1]
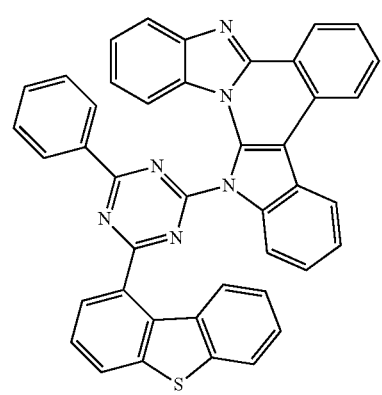 [SMILES: c1ccc(-c2nc(-c3cccc4sc5ccccc5c34)nc(-n3c4ccccc4c4c5ccccc5c5nc6ccccc6n5c43)n2)cc1]
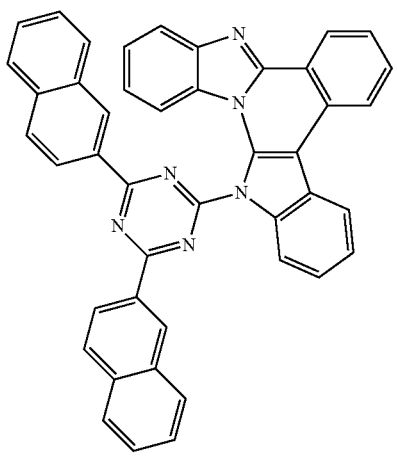 [SMILES: c1ccc2cc(-c3nc(-c4ccc5ccccc5c4)nc(-n4c5ccccc5c5c6ccccc6c6nc7ccccc7n6c54)n3)ccc2c1]
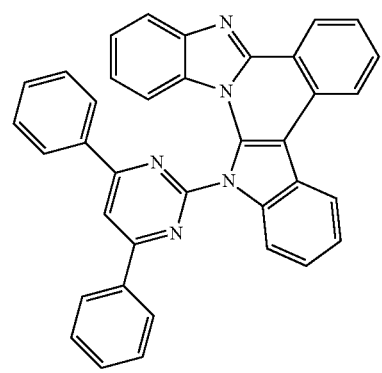 [SMILES: c1ccc(-c2cc(-c3ccccc3)nc(-n3c4ccccc4c4c5ccccc5c5nc6ccccc6n5c43)n2)cc1]
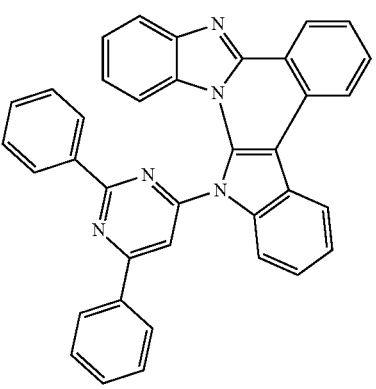 [SMILES: c1ccc(-c2cc(-n3c4ccccc4c4c5ccccc5c5nc6ccccc6n5c43)nc(-c3ccccc3)n2)cc1]
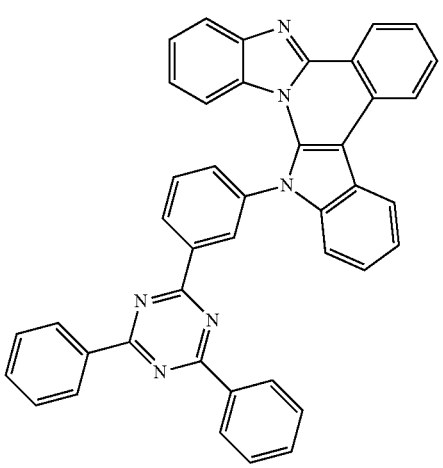 [SMILES: c1ccc(-c2nc(-c3ccccc3)nc(-c3cccc(-n4c5ccccc5c5c6ccccc6c6nc7ccccc7n6c54)c3)n2)cc1]
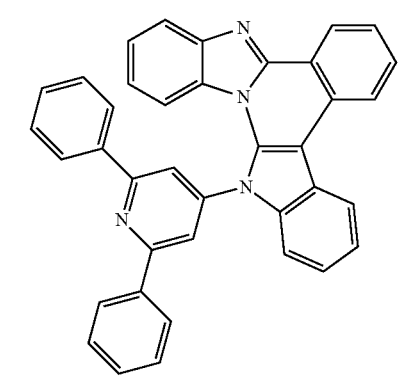 [SMILES: c1ccc(-c2cc(-n3c4ccccc4c4c5ccccc5c5nc6ccccc6n5c43)cc(-c3ccccc3)n2)cc1]
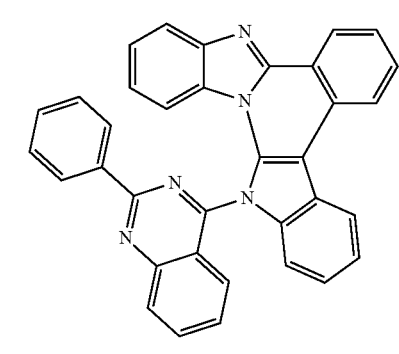 [SMILES: c1ccc(-c2nc(-n3c4ccccc4c4c5ccccc5c5nc6ccccc6n5c43)c3ccccc3n2)cc1]

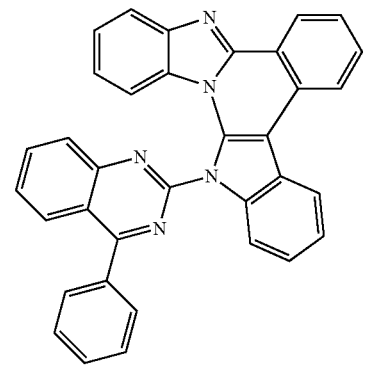 [SMILES: c1ccc(-c2nc(-n3c4ccccc4c4c5ccccc5c5nc6ccccc6n5c43)nc3ccccc23)cc1]
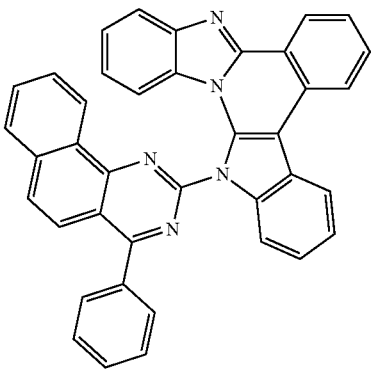
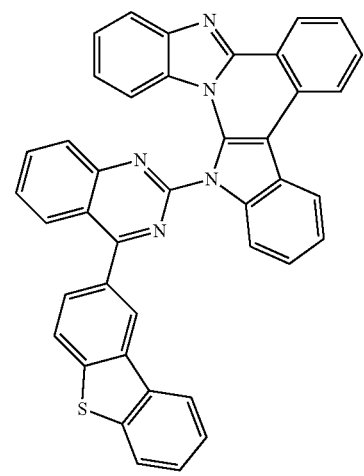 [SMILES: c1ccc2c(-c3ccc4sc5ccccc5c4c3)nc(-n3c4ccccc4c4c5ccccc5c5nc6ccccc6n5c43)nc2c1]
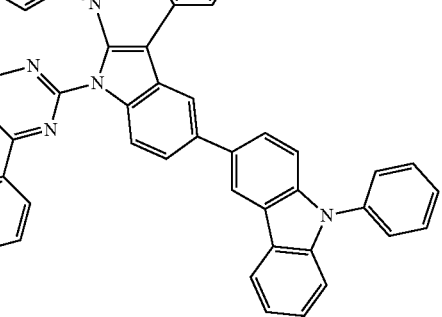
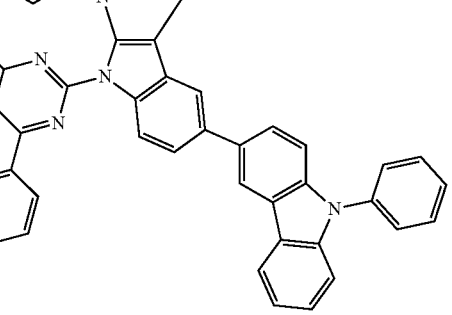
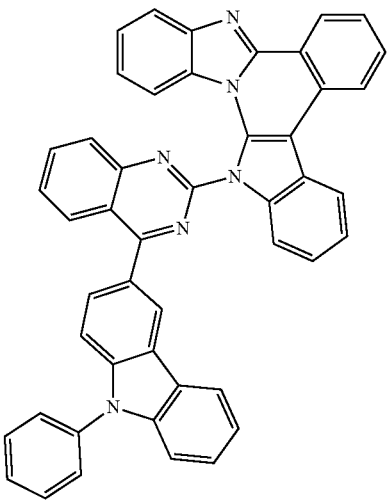 [SMILES: c1ccc(-n2c3ccccc3c3cc(-c4nc(-n5c6ccccc6c6c7ccccc7c7nc8ccccc8n7c65)nc5ccccc45)ccc32)cc1]
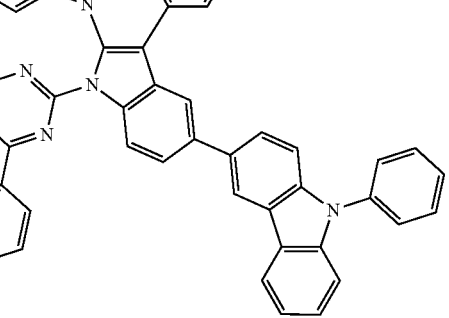

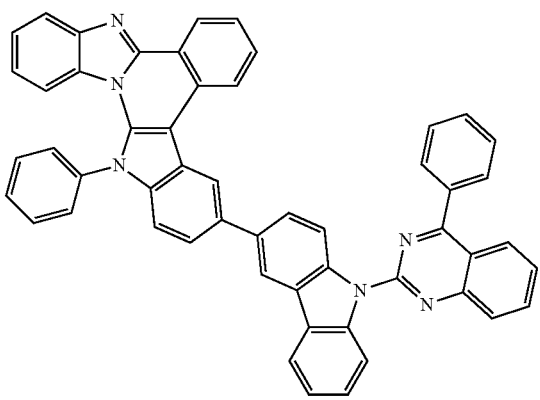 [SMILES: c1ccc(-c2nc(-n3c4ccccc4c4cc(-c5ccc6c(c5)c5c7ccccc7c7nc8ccccc8n7c5n6-c5ccccc5)ccc43)nc3ccccc23)cc1]
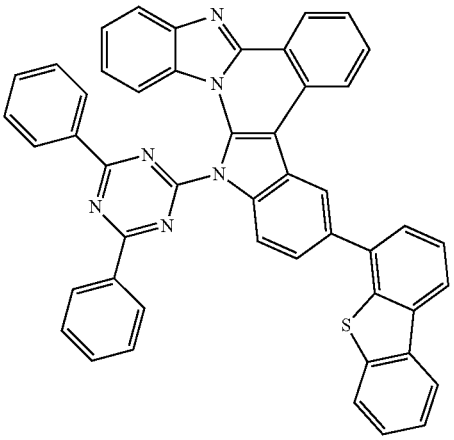
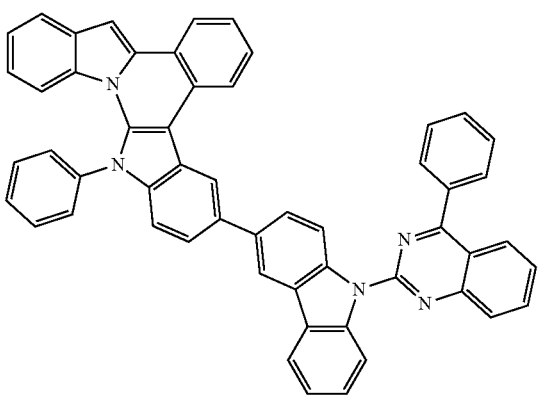 [SMILES: c1ccc(-c2nc(-n3c4ccccc4c4cc(-c5ccc6c(c5)c5c7ccccc7c7cc8ccccc8n7c5n6-c5ccccc5)ccc43)nc3ccccc23)cc1]
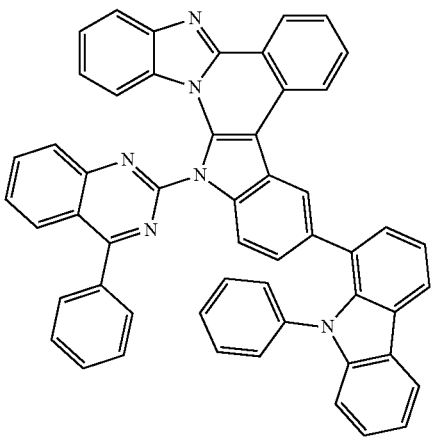
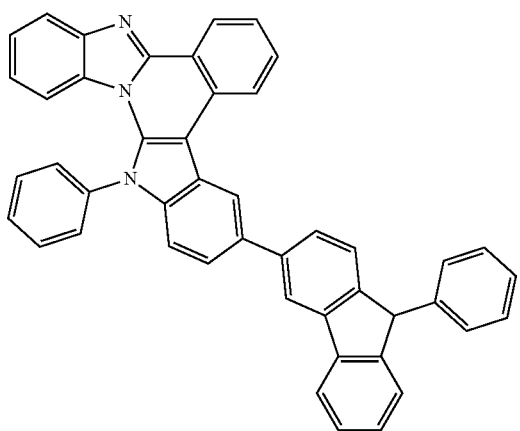 [SMILES: c1ccc(C2c3ccccc3-c3cc(-c4ccc5c(c4)c4c6ccccc6c6nc7ccccc7n6c4n5-c4ccccc4)ccc32)cc1]
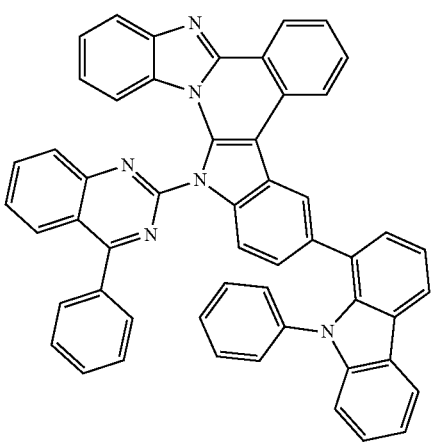 [SMILES: c1ccc(-c2nc(-n3c4ccc(-c5cccc6c7ccccc7n(-c7ccccc7)c56)cc4c4c5ccccc5c5nc6ccccc6n5c43)nc3ccccc23)cc1]

| 69 -continued | 70 -continued |
|---|---|
| 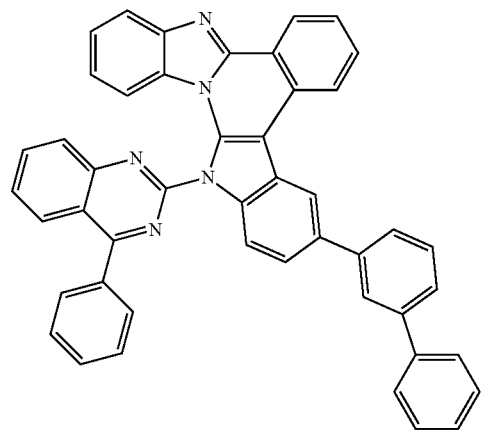 [SMILES: c1ccc(-c2cccc(-c3ccc4c(c3)c3c5ccccc5c5nc6ccccc6n5c3n4-c3nc(-c4ccccc4)c4ccccc4n3)c2)cc1] | 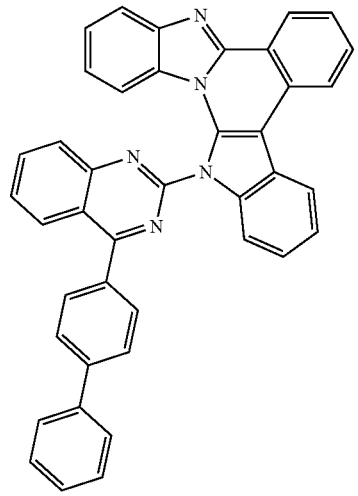 |
| 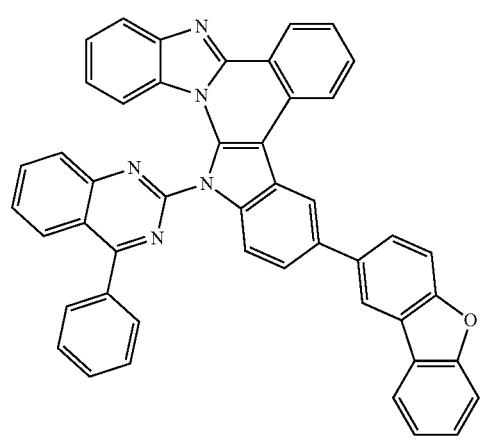 [SMILES: c1ccc(-c2nc(-n3c4ccc(-c5ccc6oc7ccccc7c6c5)cc4c4c5ccccc5c5nc6ccccc6n5c43)nc3ccccc23)cc1] | 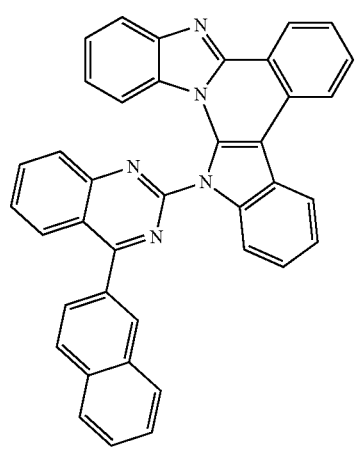 |
| 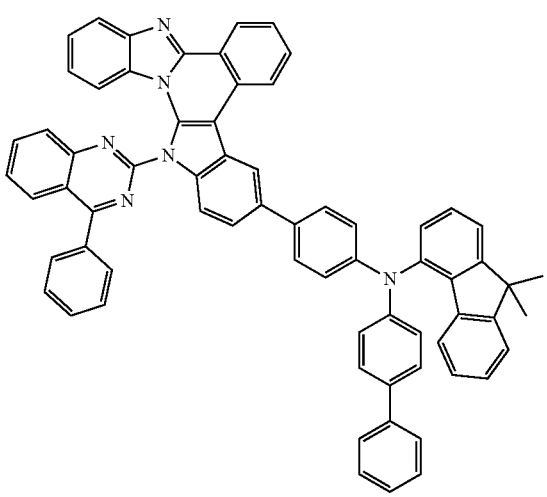 [SMILES: CC1(C)c2ccccc2-c2c(N(c3ccc(-c4ccccc4)cc3)c3ccc(-c4ccc5c(c4)c4c6ccccc6c6nc7ccccc7n6c4n5-c4nc(-c5ccccc5)c5ccccc5n4)cc3)cccc21] | 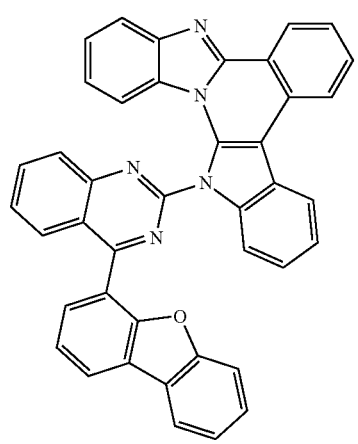 [SMILES: c1ccc2c(-c3cccc4c3oc3ccccc34)nc(-n3c4ccccc4c4c5ccccc5c5nc6ccccc6n5c43)nc2c1] |

| 71 -continued | 72 -continued |
|---|---|
| 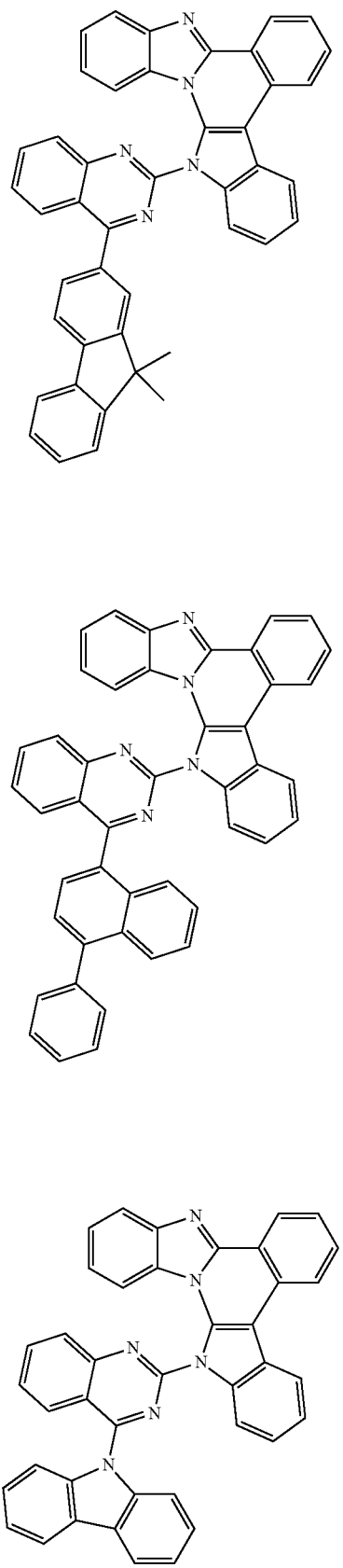 | 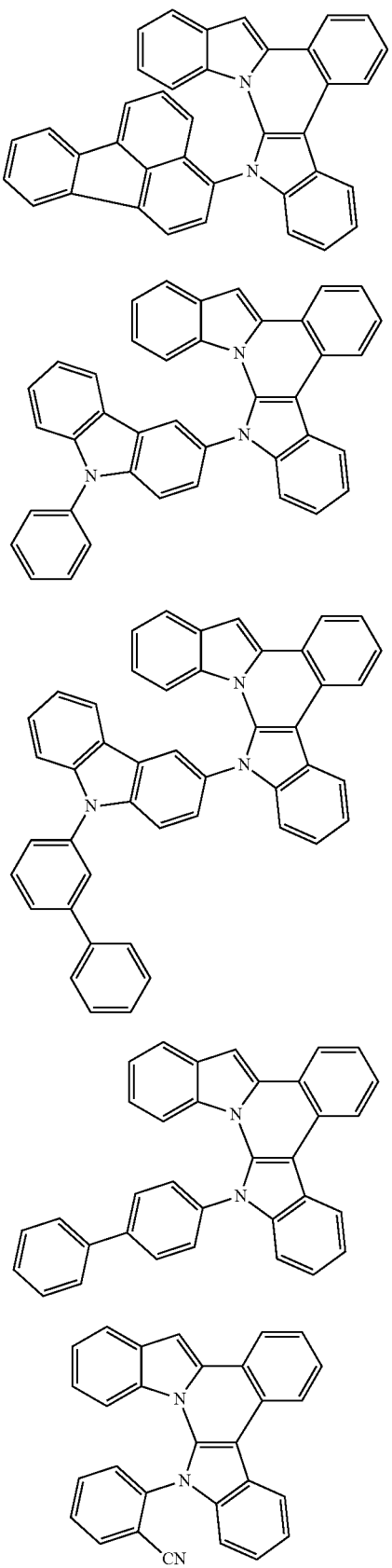 |

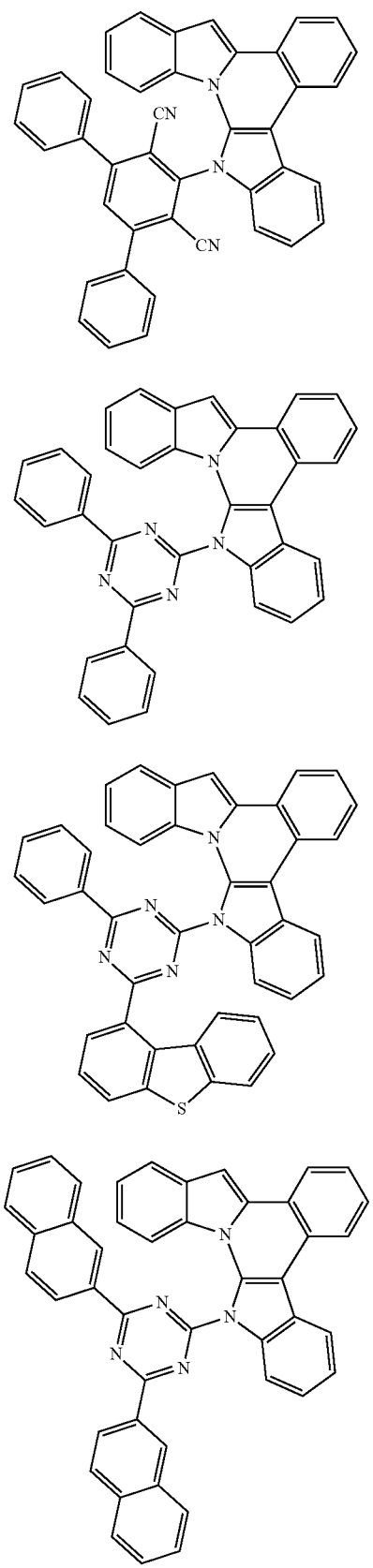
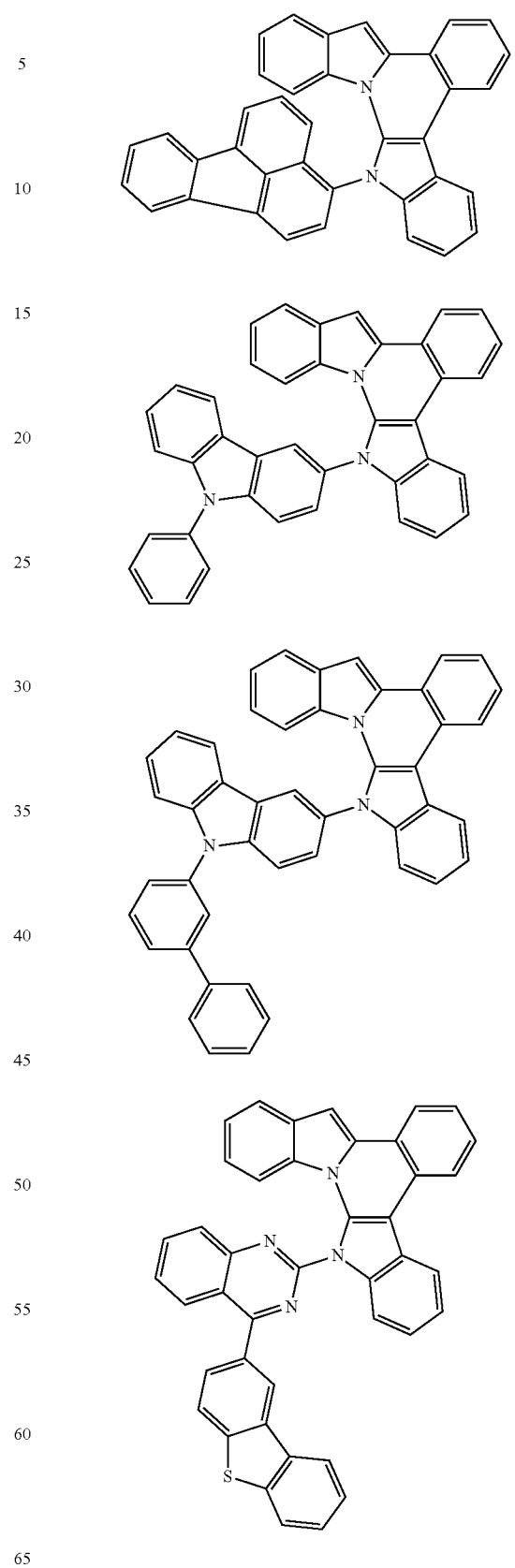

75
-continued
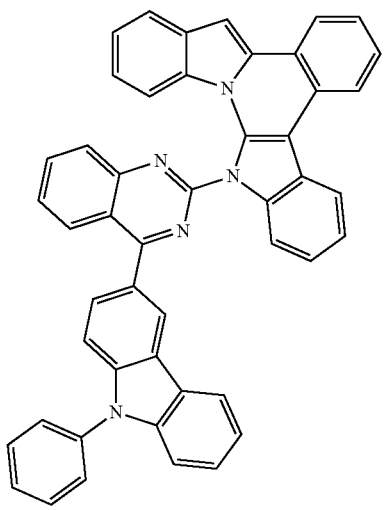 [SMILES: c1ccc(-n2c3ccccc3c3cc(-c4nc(-n5c6ccccc6c6c7ccccc7c7cc8ccccc8n7c65)nc5ccccc45)ccc32)cc1]
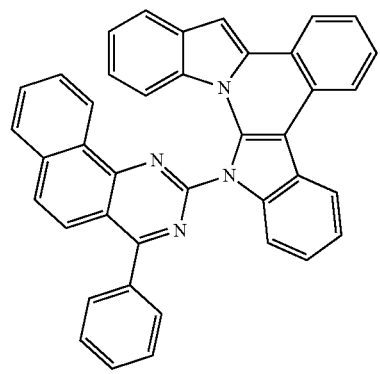
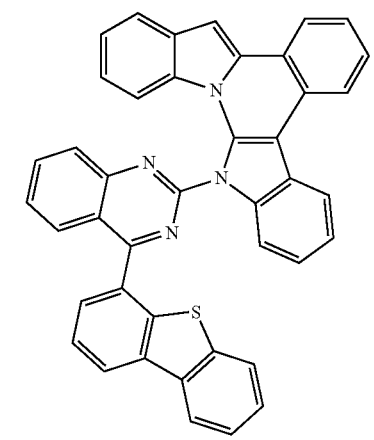 [SMILES: c1ccc2c(c1)cc1c3ccccc3c3c4ccccc4n(-c4nc(-c5cccc6c5sc5ccccc56)c5ccccc5n4)c3n21]
76
-continued
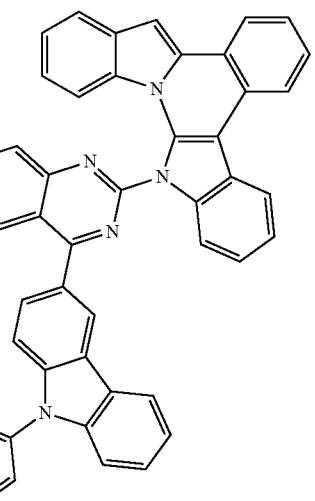
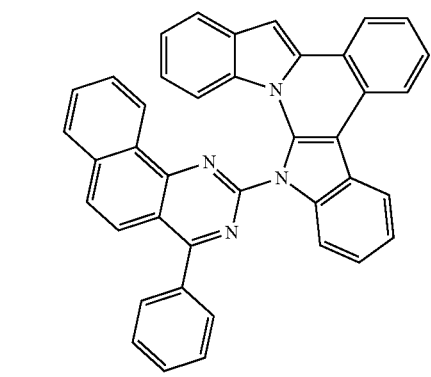
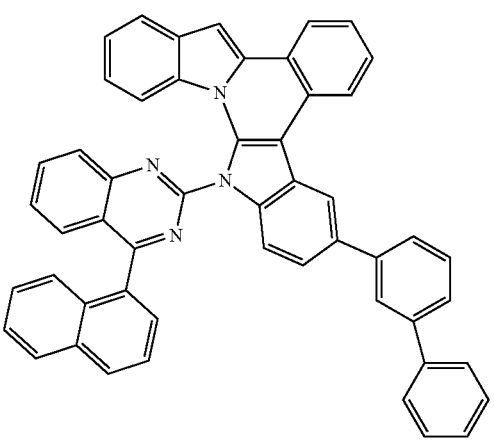 [SMILES: c1ccc(-c2cccc(-c3ccc4c(c3)c3c5ccccc5c5cc6ccccc6n5c3n4-c3nc(-c4cccc5ccccc45)c4ccccc4n3)c2)cc1]

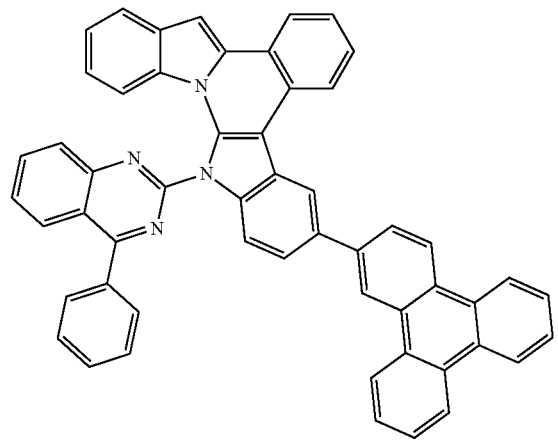 [SMILES: c1ccc(-c2nc(-n3c4ccc(-c5ccc6c7ccccc7c7ccccc7c6c5)cc4c4c5ccccc5c5cc6ccccc6n5c43)nc3ccccc23)cc1]
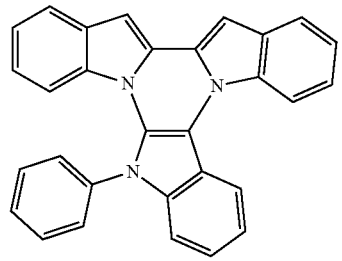 [SMILES: c1ccc(-n2c3ccccc3c3c2n2c4ccccc4cc2c2cc4ccccc4n23)cc1]
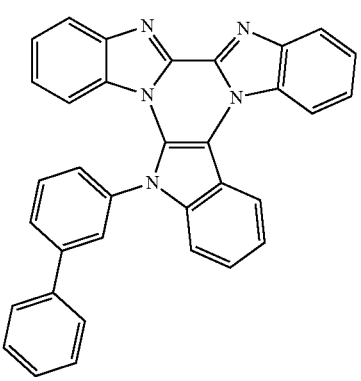 [SMILES: c1ccc(-c2cccc(-n3c4ccccc4c4c3n3c5ccccc5nc3c3nc5ccccc5n34)c2)cc1]
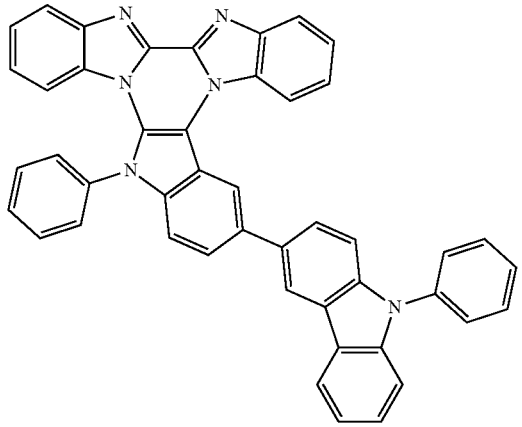 [SMILES: c1ccc(-n2c3ccccc3c3cc(-c4ccc5c(c4)c4c(n5-c5ccccc5)n5c6ccccc6nc5c5nc6ccccc6n54)ccc32)cc1]
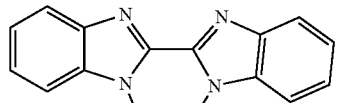
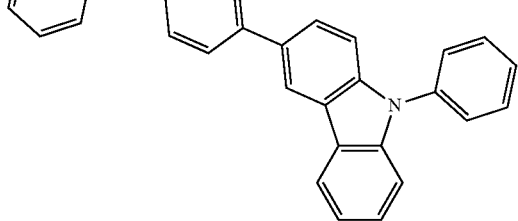

-continued
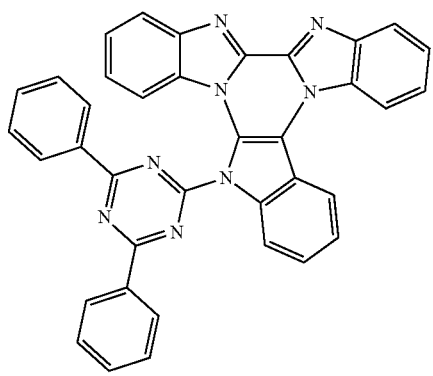 [SMILES: c1ccc(-c2nc(-c3ccccc3)nc(-n3c4ccccc4c4c3n3c5ccccc5nc3c3nc5ccccc5n34)n2)cc1]
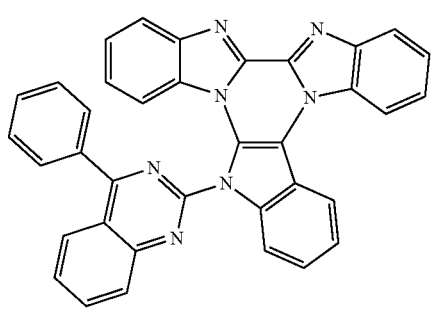 [SMILES: c1ccc(-c2nc(-n3c4ccccc4c4c3n3c5ccccc5nc3c3nc5ccccc5n34)nc3ccccc23)cc1]
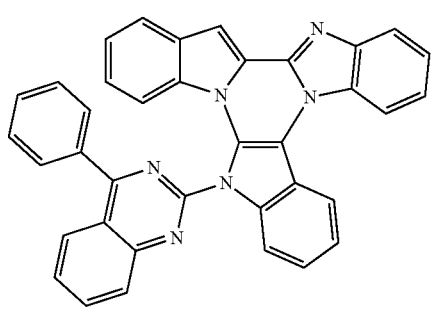 [SMILES: c1ccc(-c2nc(-n3c4ccccc4c4c3n3c5ccccc5cc3c3nc5ccccc5n34)nc3ccccc23)cc1]
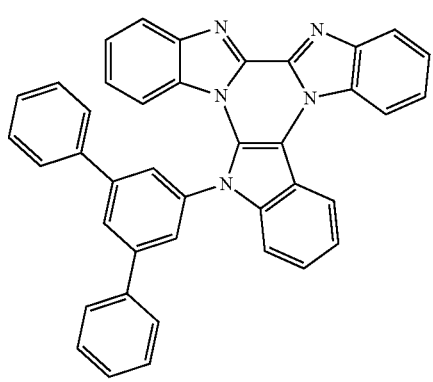 [SMILES: c1ccc(-c2cc(-c3ccccc3)cc(-n3c4ccccc4c4c3n3c5ccccc5nc3c3nc5ccccc5n34)c2)cc1]
-continued
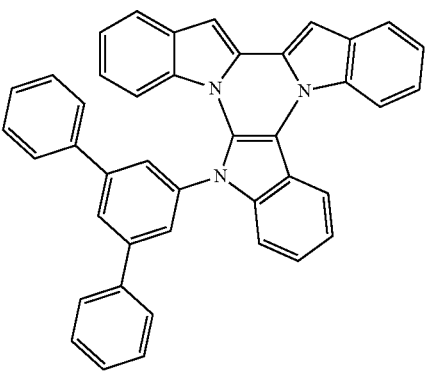 [SMILES: c1ccc(-c2cc(-c3ccccc3)cc(-n3c4ccccc4c4c3n3c5ccccc5cc3c3cc5ccccc5n34)c2)cc1]
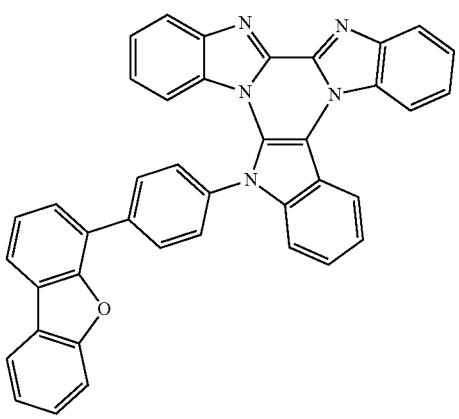 [SMILES: c1ccc2c(c1)nc1c3nc4ccccc4n3c3c(c4ccccc4n3-c3ccc(-c4cccc5c4oc4ccccc45)cc3)n21]
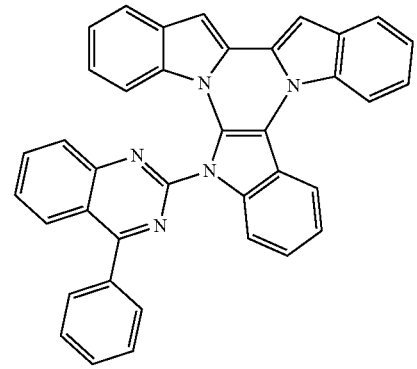 [SMILES: c1ccc(-c2nc(-n3c4ccccc4c4c3n3c5ccccc5cc3c3cc5ccccc5n34)nc3ccccc23)cc1]
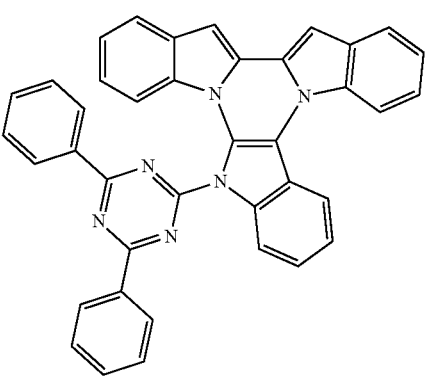 [SMILES: c1ccc(-c2nc(-c3ccccc3)nc(-n3c4ccccc4c4c3n3c5ccccc5cc3c3cc5ccccc5n34)n2)cc1]

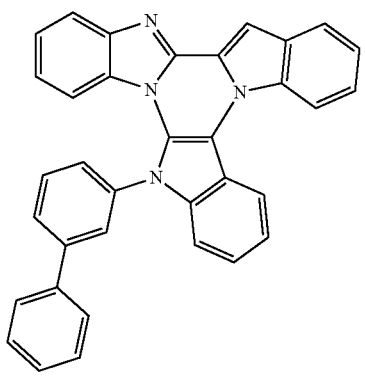 [SMILES: c1ccc(-c2cccc(-n3c4ccccc4c4c3n3c5ccccc5nc3c3cc5ccccc5n34)c2)cc1]
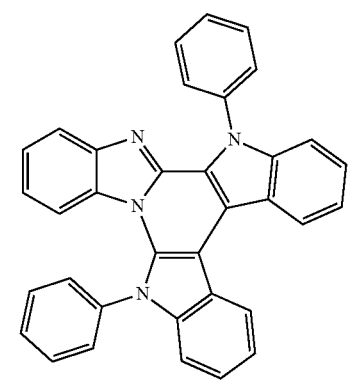 [SMILES: c1ccc(-n2c3ccccc3c3c4c5ccccc5n(-c5ccccc5)c4n4c5ccccc5nc4c32)cc1]
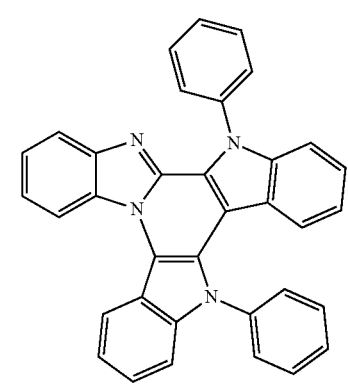 [SMILES: c1ccc(-n2c3ccccc3c3c2c2nc4ccccc4n2c2c4ccccc4n(-c4ccccc4)c32)cc1]
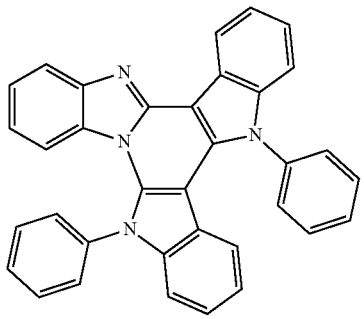 [SMILES: c1ccc(-n2c3ccccc3c3c2c2c4ccccc4n(-c4ccccc4)c2n2c4ccccc4nc32)cc1]
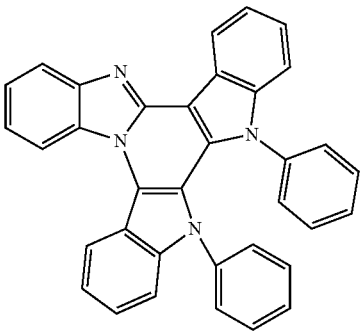 [SMILES: c1ccc(-n2c3ccccc3c3c2c2c(c4ccccc4n2-c2ccccc2)n2c4ccccc4nc32)cc1]
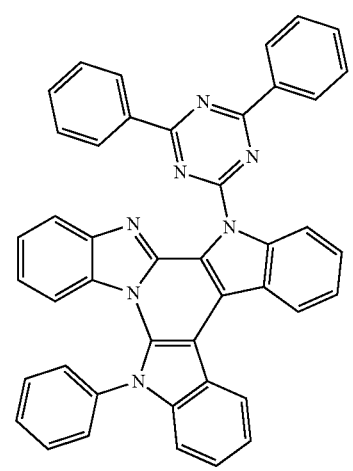 [SMILES: c1ccc(-c2nc(-c3ccccc3)nc(-n3c4ccccc4c4c5c6ccccc6n(-c6ccccc6)c5n5c6ccccc6nc5c43)n2)cc1]
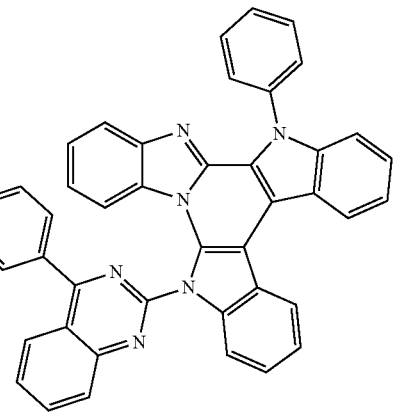
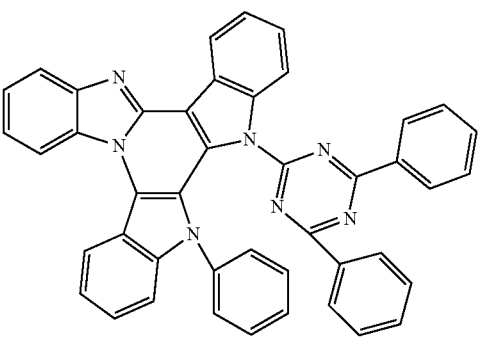 [SMILES: c1ccc(-c2nc(-c3ccccc3)nc(-n3c4ccccc4c4c3c3c(c5ccccc5n3-c3ccccc3)n3c5ccccc5nc43)n2)cc1]

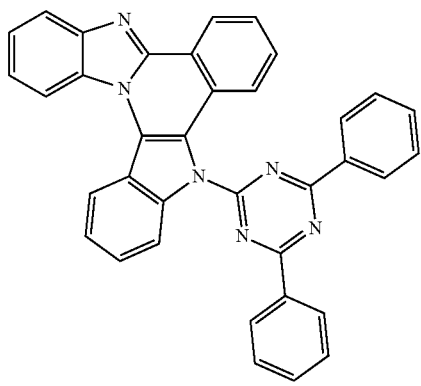 [SMILES: c1ccc(-c2nc(-c3ccccc3)nc(-n3c4ccccc4c4c3c3ccccc3c3nc5ccccc5n34)n2)cc1]
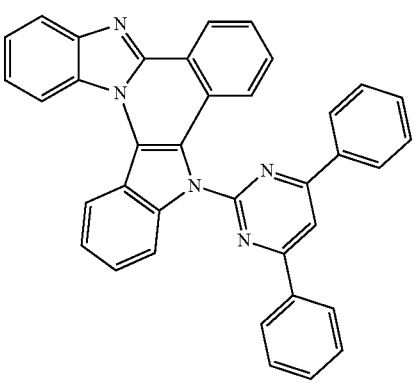
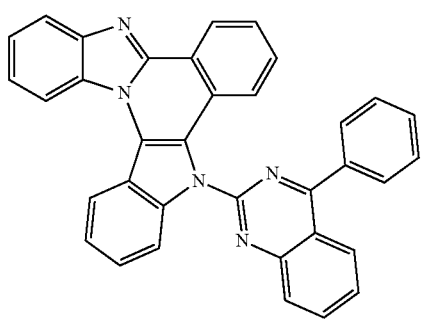 [SMILES: c1ccc(-c2nc(-n3c4ccccc4c4c3c3ccccc3c3nc5ccccc5n34)nc3ccccc23)cc1]
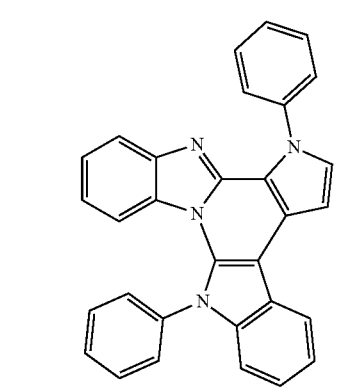
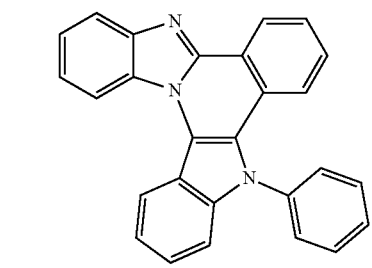 [SMILES: c1ccc(-n2c3ccccc3c3c2c2ccccc2c2nc4ccccc4n23)cc1]
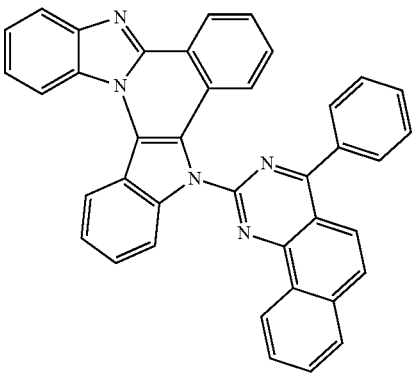
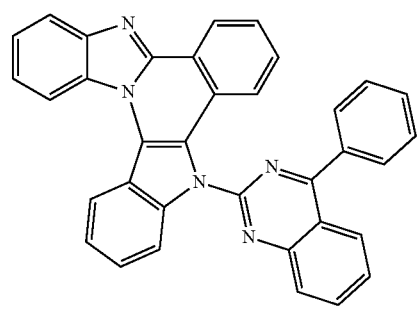 [SMILES: c1ccc(-c2nc(-n3c4ccccc4c4c3c3ccccc3c3nc5ccccc5n34)nc3ccccc23)cc1]
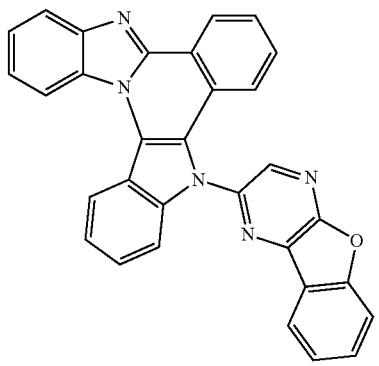 [SMILES: c1ccc2c(c1)nc1c3ccccc3c3c(c4ccccc4n3-c3cnc4oc5ccccc5c4n3)n21]

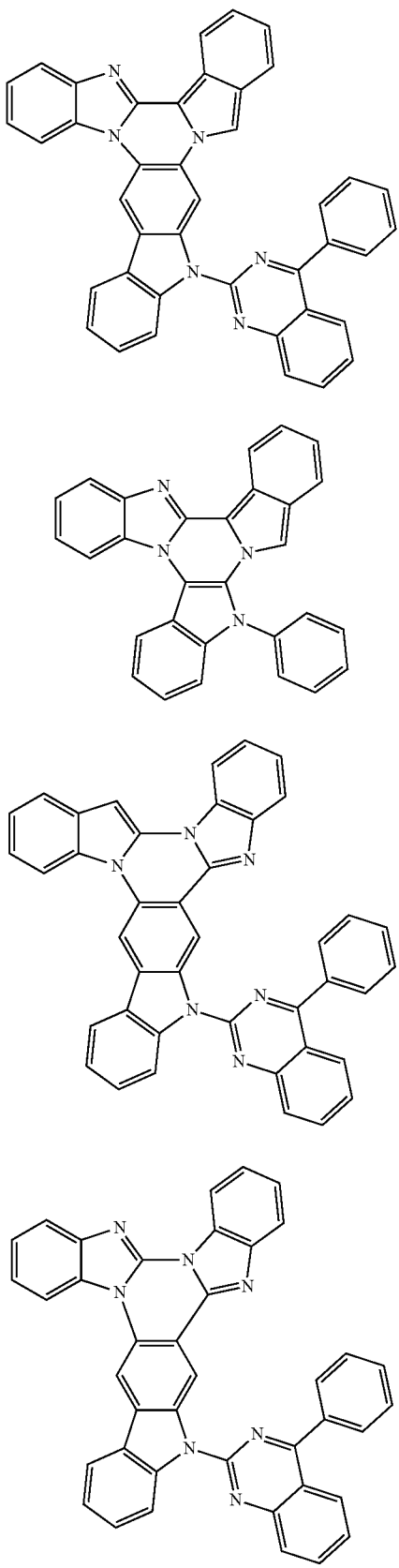
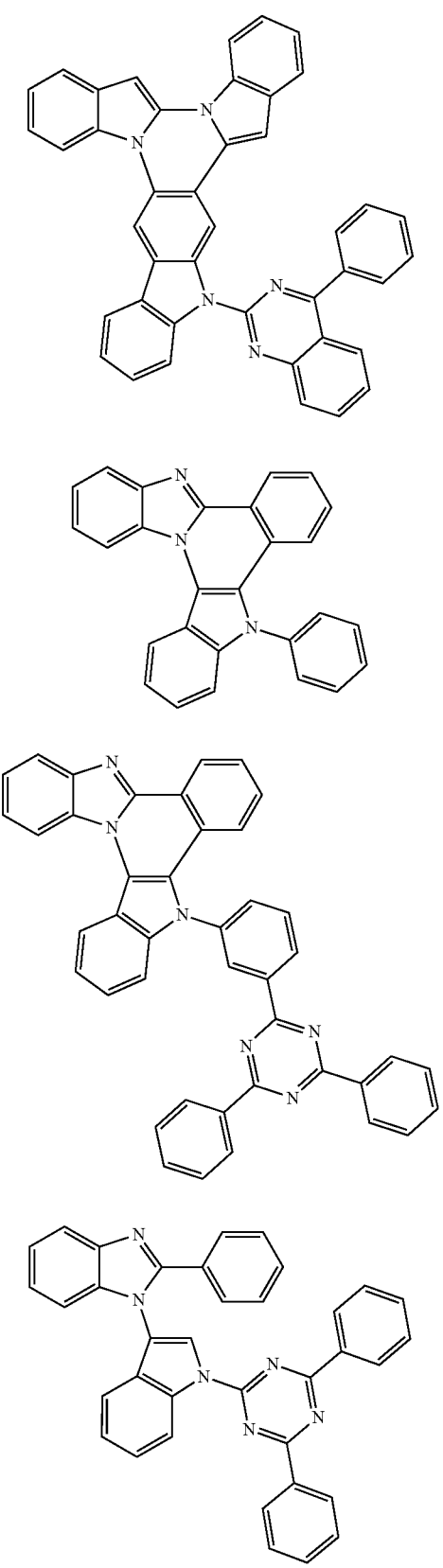

87
-continued
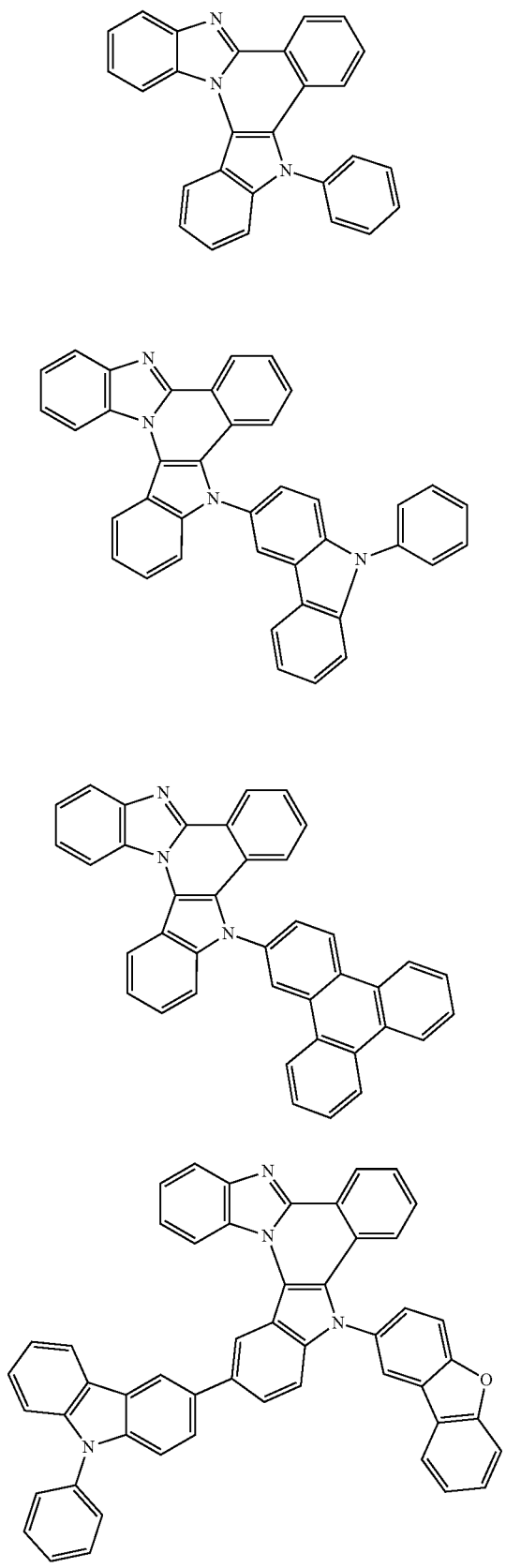
88
-continued
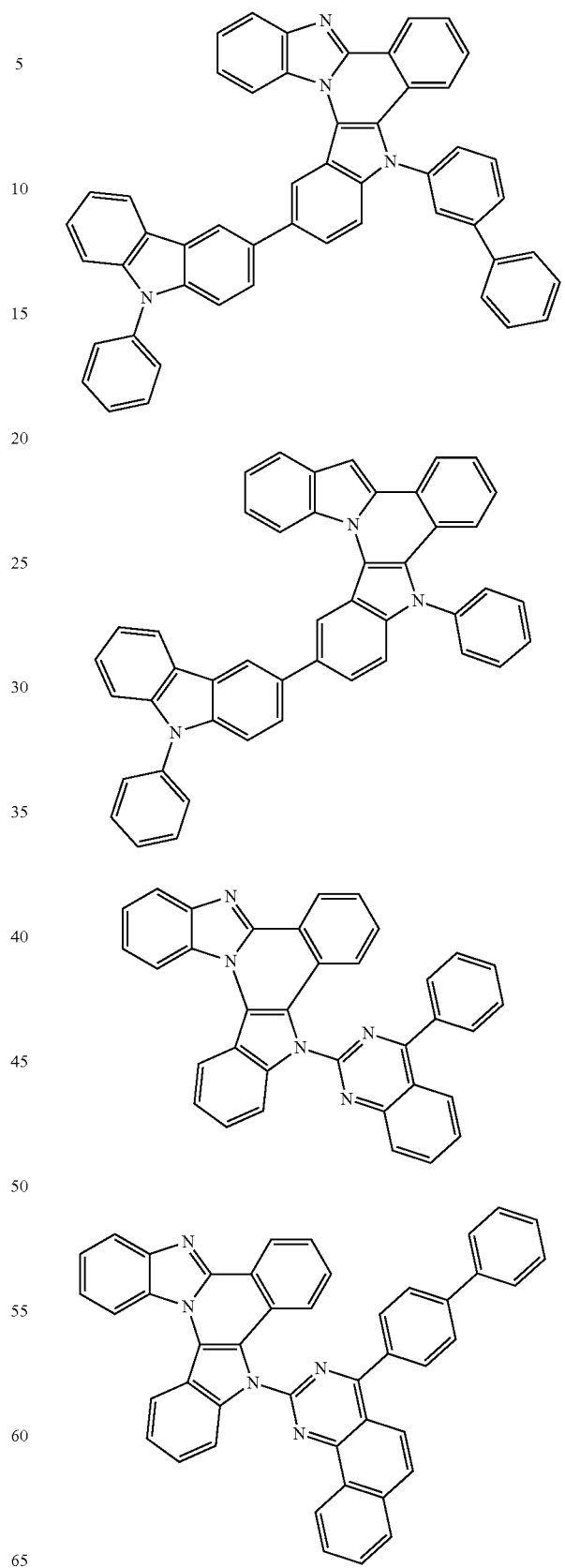

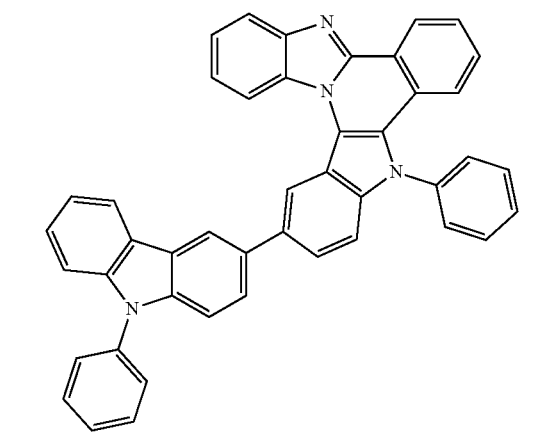 [SMILES: c1ccc(-n2c3ccccc3c3cc(-c4ccc5c(c4)c4c(c6ccccc6c6nc7ccccc7n64)n5-c4ccccc4)ccc32)cc1]
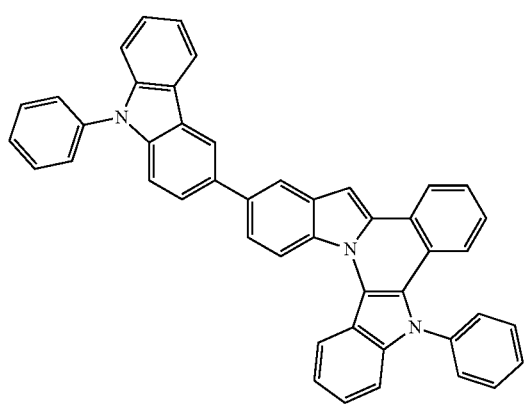
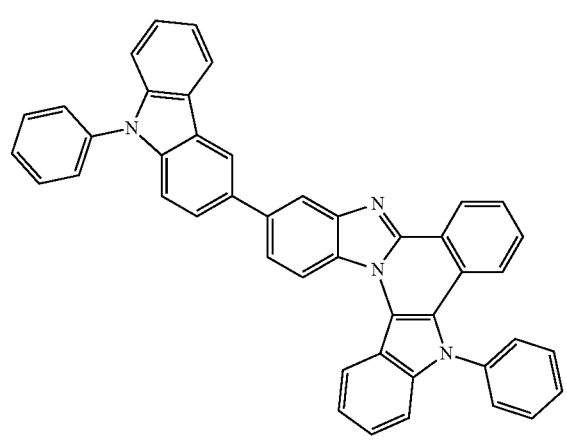 [SMILES: c1ccc(-n2c3ccccc3c3cc(-c4ccc5c(c4)nc4c6ccccc6c6c(c7ccccc7n6-c6ccccc6)n54)ccc32)cc1]
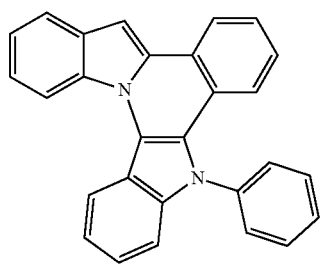 [SMILES: c1ccc(-n2c3ccccc3c3c2c2ccccc2c2cc4ccccc4n23)cc1]
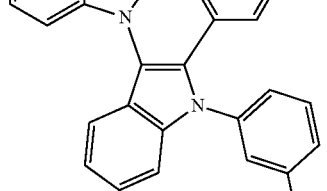
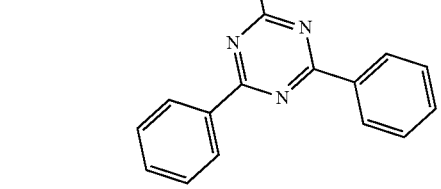
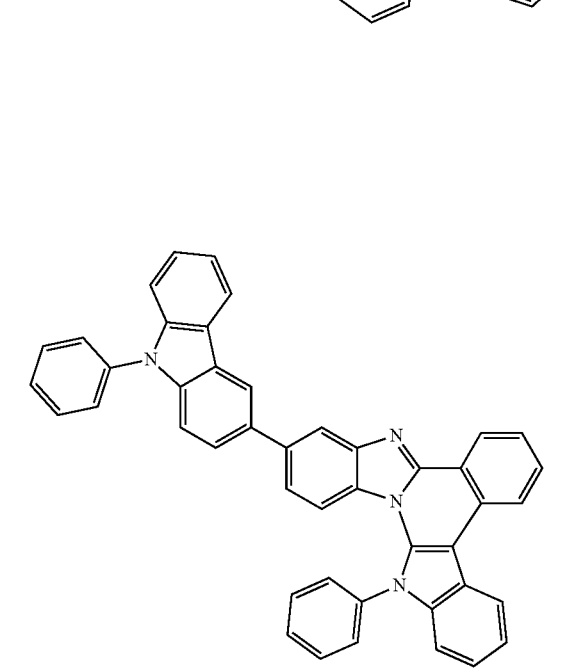
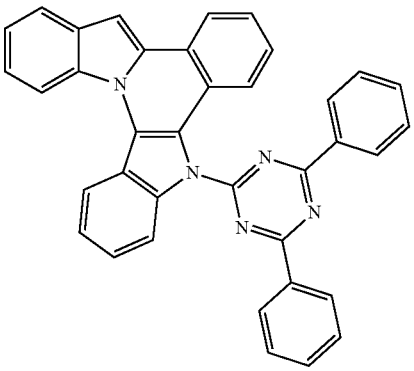 [SMILES: c1ccc(-c2nc(-c3ccccc3)nc(-n3c4ccccc4c4c3c3ccccc3c3cc5ccccc5n34)n2)cc1]

91
-continued
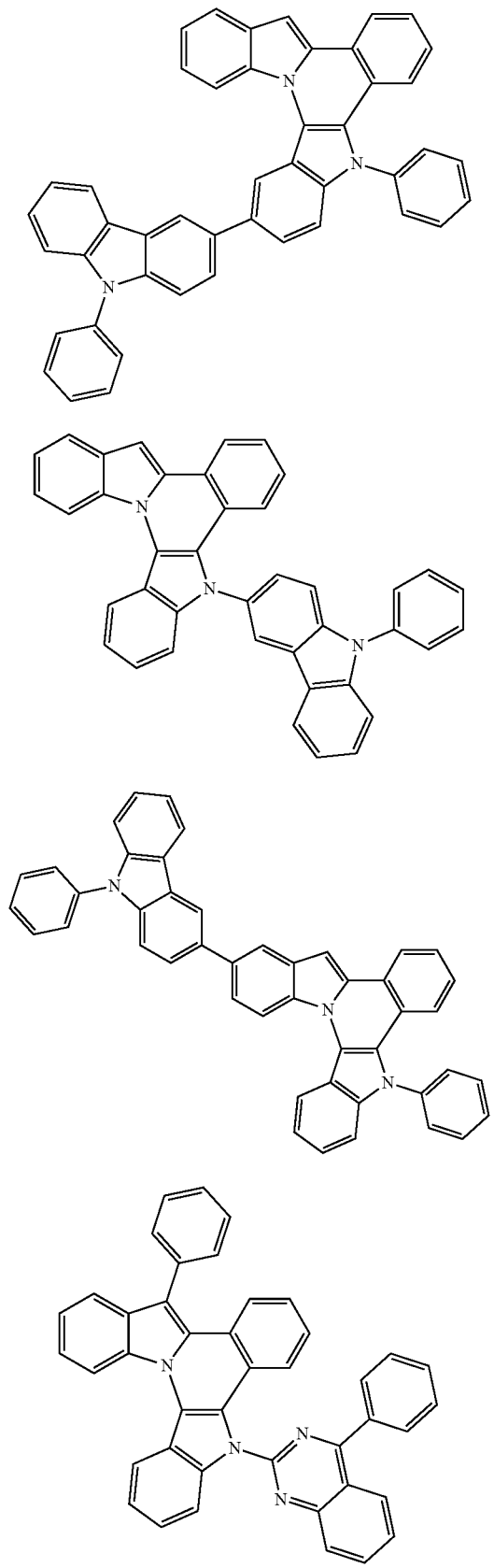
92
-continued
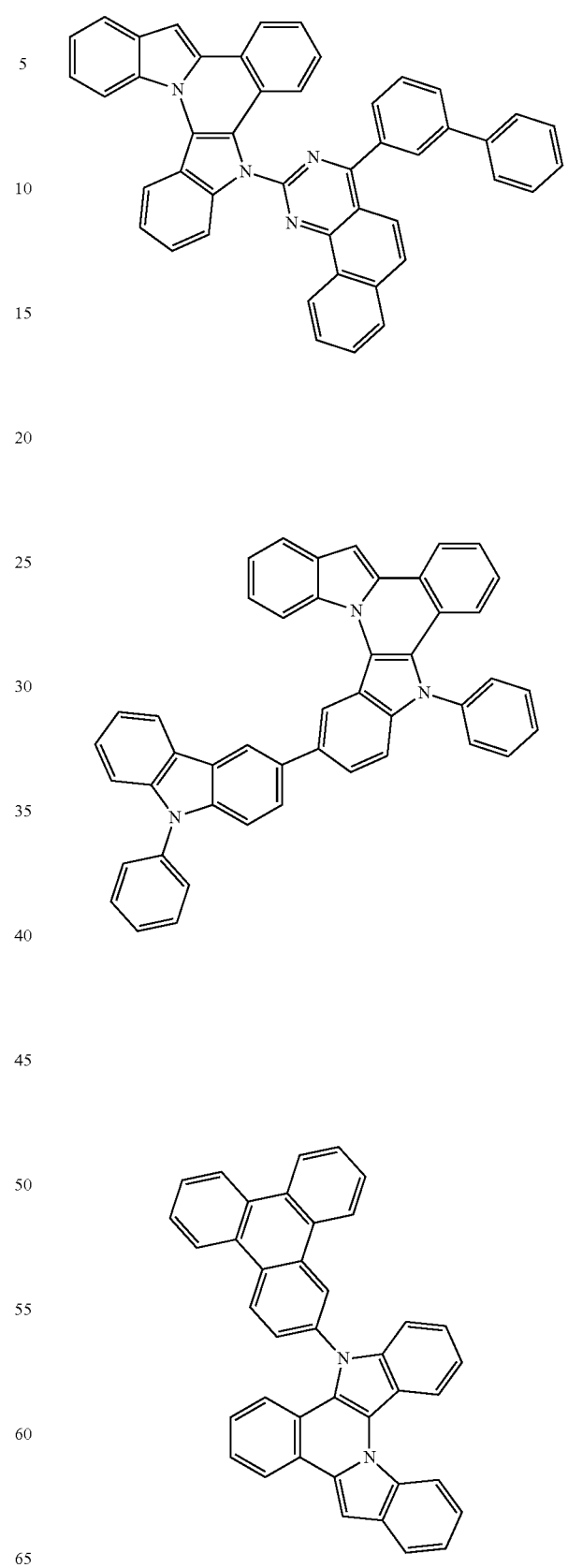

93
-continued
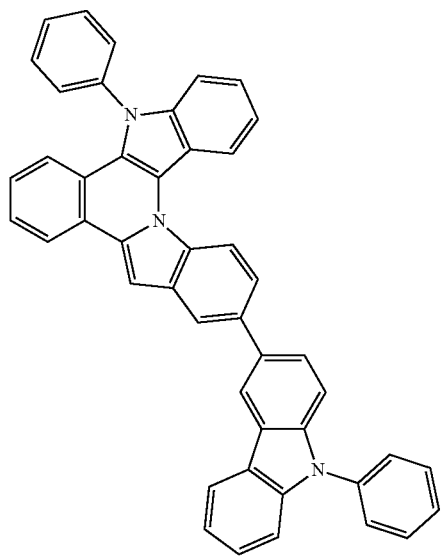 [SMILES: c1ccc(-n2c3ccccc3c3cc(-c4ccc5c(c4)cc4c6ccccc6c6c(c7ccccc7n6-c6ccccc6)n54)ccc32)cc1]
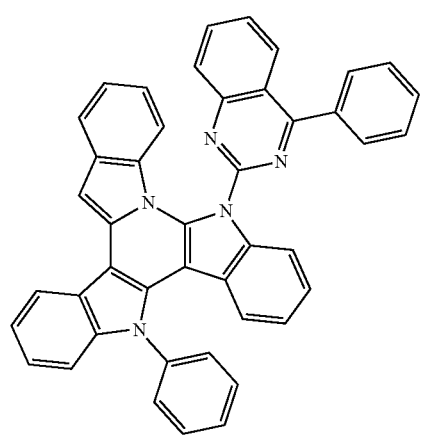 [SMILES: c1ccc(-c2nc(-n3c4ccccc4c4c5c(c6ccccc6n5-c5ccccc5)c5cc6ccccc6n5c43)nc3ccccc23)cc1]
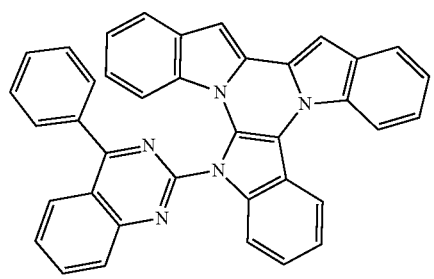 [SMILES: c1ccc(-c2nc(-n3c4ccccc4c4c3n3c5ccccc5cc3c3cc5ccccc5n34)nc3ccccc23)cc1]
94
-continued
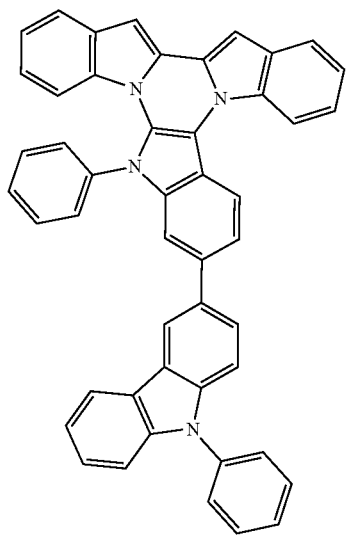 [SMILES: c1ccc(-n2c3ccccc3c3cc(-c4ccc5c(c4)n(-c4ccccc4)c4c5n5c6ccccc6cc5c5cc6ccccc6n54)ccc32)cc1]
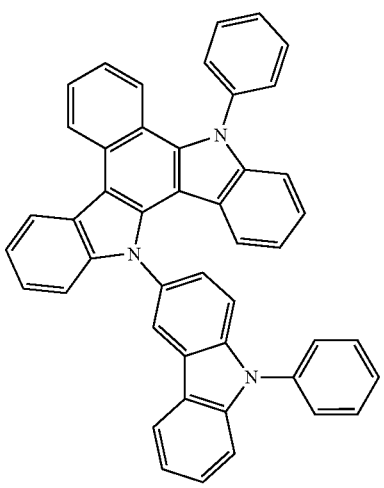 [SMILES: c1ccc(-n2c3ccccc3c3cc(-n4c5ccccc5c5c6ccccc6c6c(c7ccccc7n6-c6ccccc6)c54)ccc32)cc1]
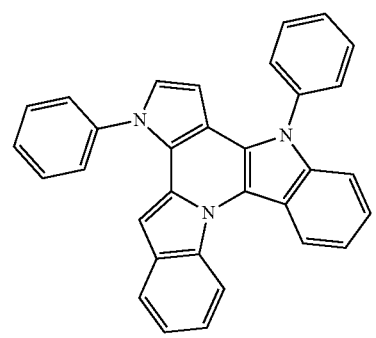 [SMILES: c1ccc(-n2ccc3c2c2cc4ccccc4n2c2c4ccccc4n(-c4ccccc4)c32)cc1]

-continued
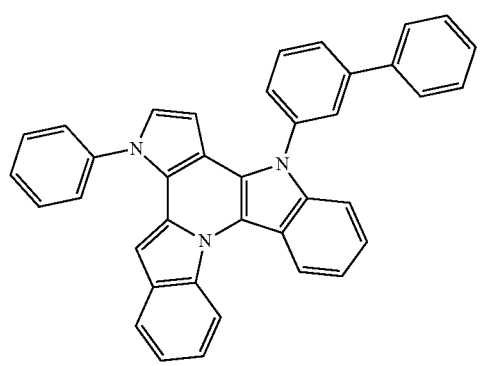 [SMILES: c1ccc(-c2cccc(-n3c4ccccc4c4c3c3ccn(-c5ccccc5)c3c3cc5ccccc5n34)c2)cc1]
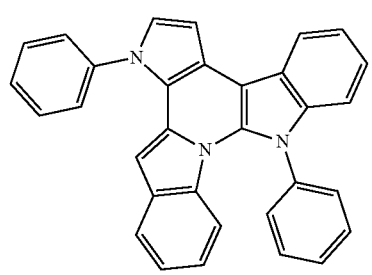 [SMILES: c1ccc(-n2ccc3c4c5ccccc5n(-c5ccccc5)c4n4c5ccccc5cc4c32)cc1]
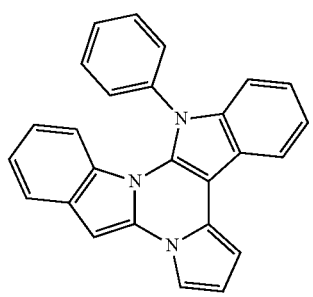 [SMILES: c1ccc(-n2c3ccccc3c3c4cccn4c4cc5ccccc5n4c32)cc1]
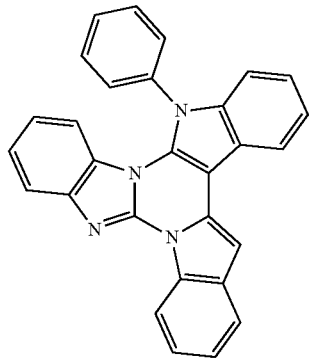 [SMILES: c1ccc(-n2c3ccccc3c3c4cc5ccccc5n4c4nc5ccccc5n4c32)cc1]
-continued
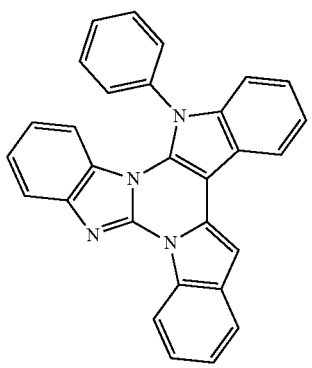 [SMILES: c1ccc(-n2c3ccccc3c3c4cc5ccccc5n4c4nc5ccccc5n4c32)cc1]
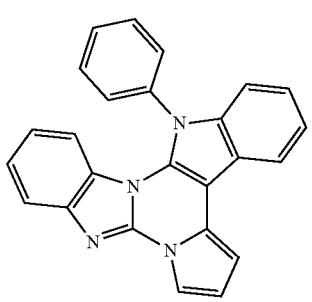 [SMILES: c1ccc(-n2c3ccccc3c3c4cccn4c4nc5ccccc5n4c32)cc1]
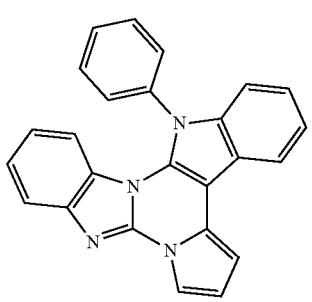 [SMILES: c1ccc(-n2c3ccccc3c3c4cccn4c4nc5ccccc5n4c32)cc1]
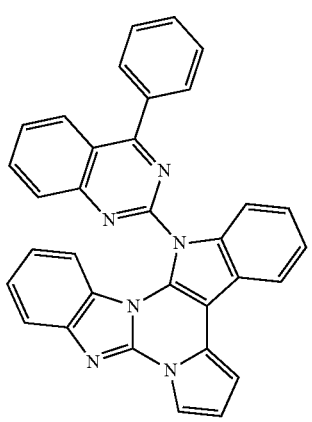 [SMILES: c1ccc(-c2nc(-n3c4ccccc4c4c5cccn5c5nc6ccccc6n5c43)nc3ccccc23)cc1]
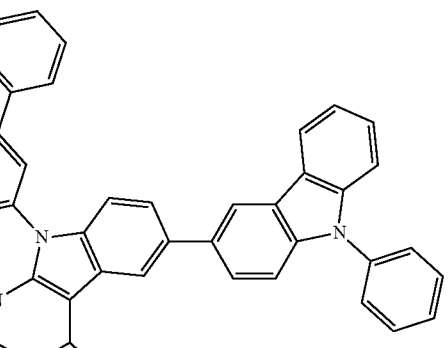

97
-continued
98
-continued
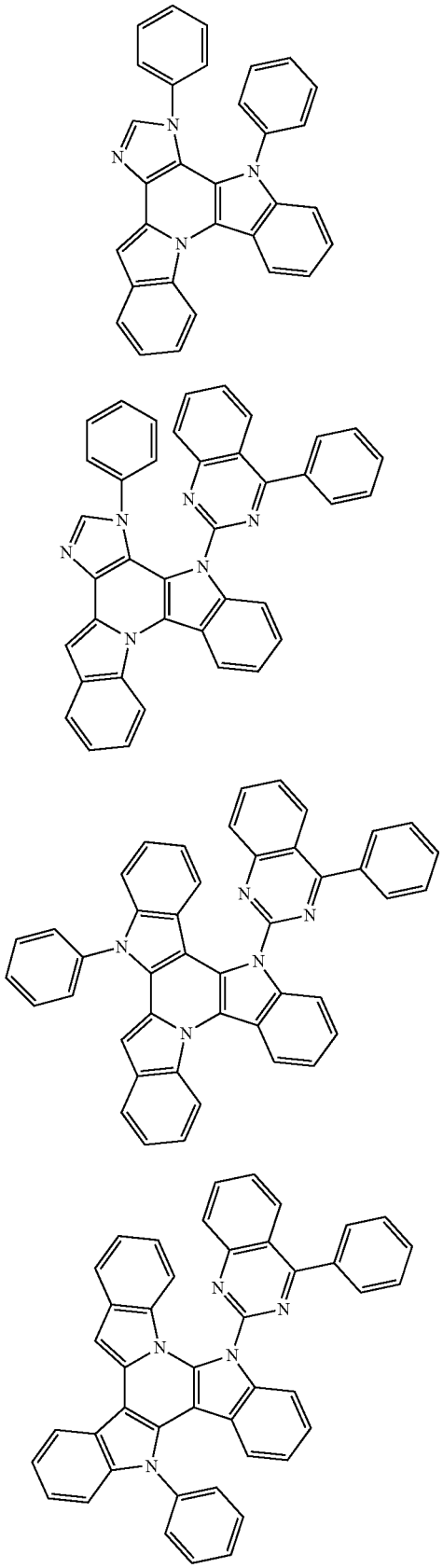
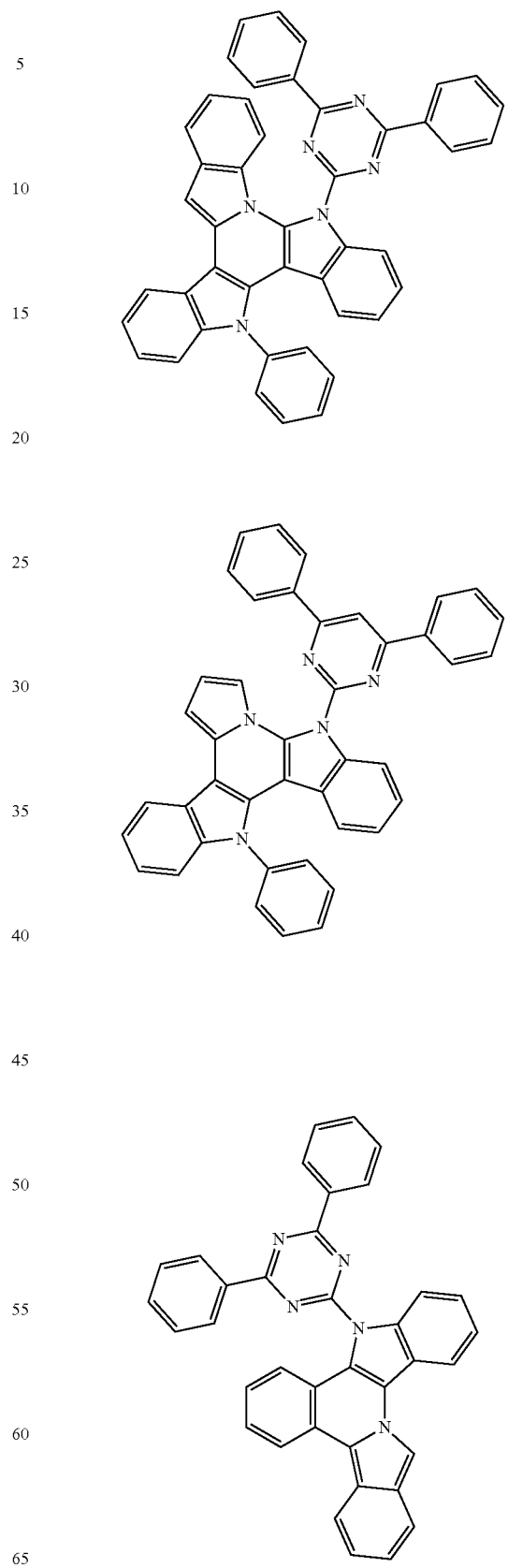

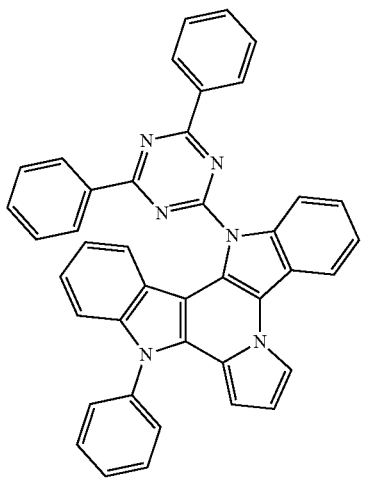 [SMILES: c1ccc(-c2nc(-c3ccccc3)nc(-n3c4ccccc4c4c3c3c5ccccc5n(-c5ccccc5)c3c3cccn34)n2)cc1]
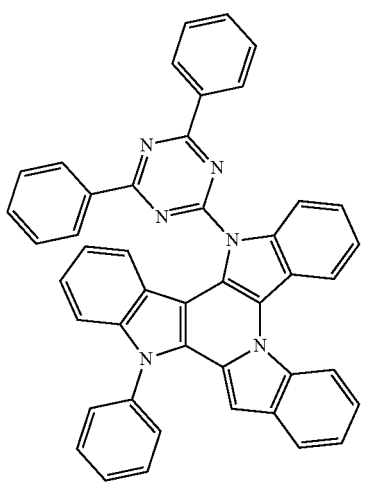 [SMILES: c1ccc(-c2nc(-c3ccccc3)nc(-n3c4ccccc4c4c3c3c5ccccc5n(-c5ccccc5)c3c3cc5ccccc5n34)n2)cc1]
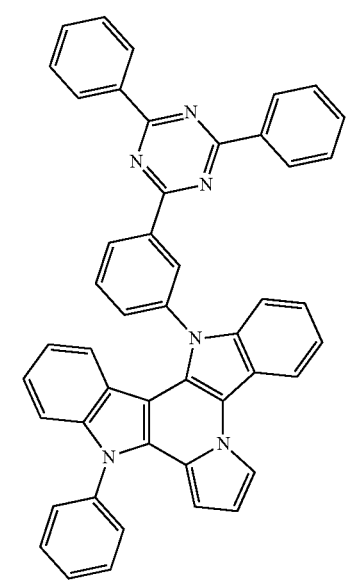 [SMILES: c1ccc(-c2nc(-c3ccccc3)nc(-c3cccc(-n4c5ccccc5c5c4c4c6ccccc6n(-c6ccccc6)c4c4cccn45)c3)n2)cc1]
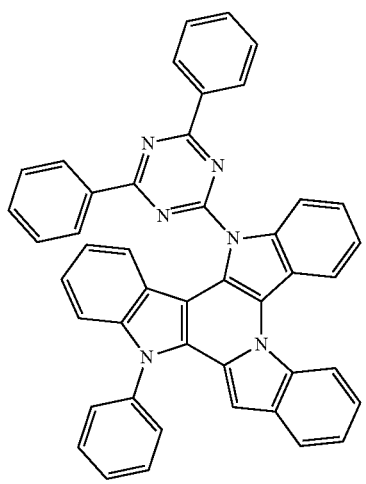 [SMILES: c1ccc(-c2nc(-c3ccccc3)nc(-n3c4ccccc4c4c3c3c5ccccc5n(-c5ccccc5)c3c3cc5ccccc5n34)n2)cc1]
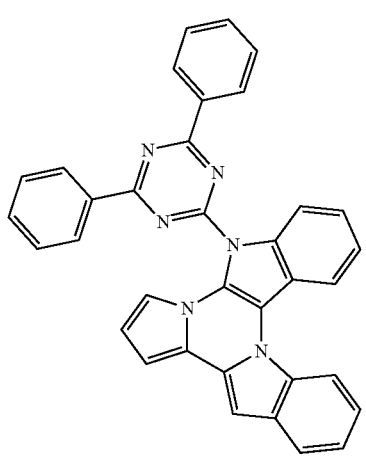 [SMILES: c1ccc(-c2nc(-c3ccccc3)nc(-n3c4ccccc4c4c3n3cccc3c3cc5ccccc5n34)n2)cc1]
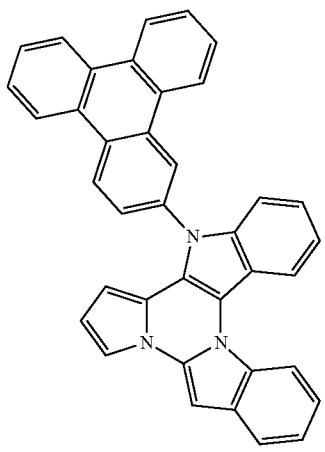 [SMILES: c1ccc2c(c1)cc1n3cccc3c3c(c4ccccc4n3-c3ccc4c5ccccc5c5ccccc5c4c3)n21]

101
-continued
102
-continued
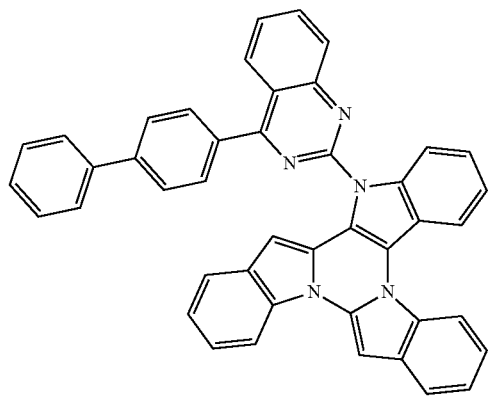 [SMILES: c1ccc(-c2ccc(-c3nc(-n4c5ccccc5c5c4c4cc6ccccc6n4c4cc6ccccc6n54)nc4ccccc34)cc2)cc1]
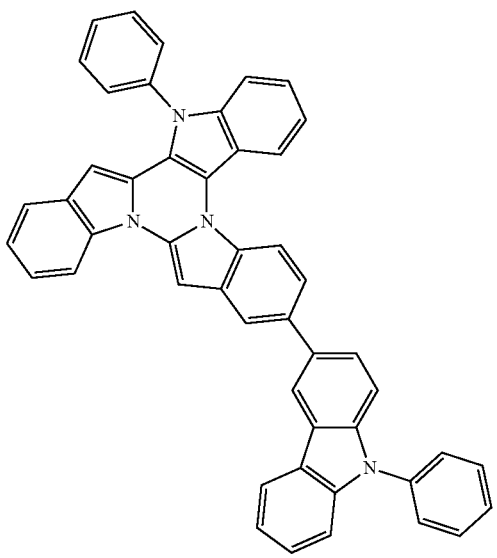 [SMILES: c1ccc(-n2c3ccccc3c3cc(-c4ccc5c(c4)cc4n6c7ccccc7cc6c6c(c7ccccc7n6-c6ccccc6)n54)ccc32)cc1]

103
-continued
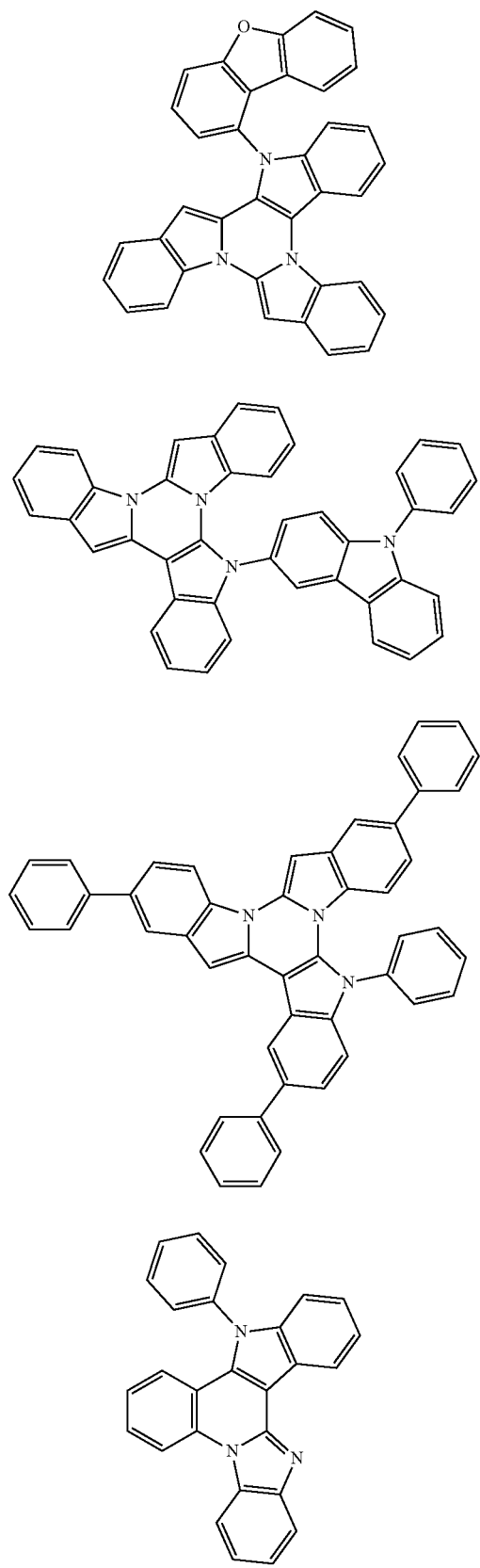
104
-continued
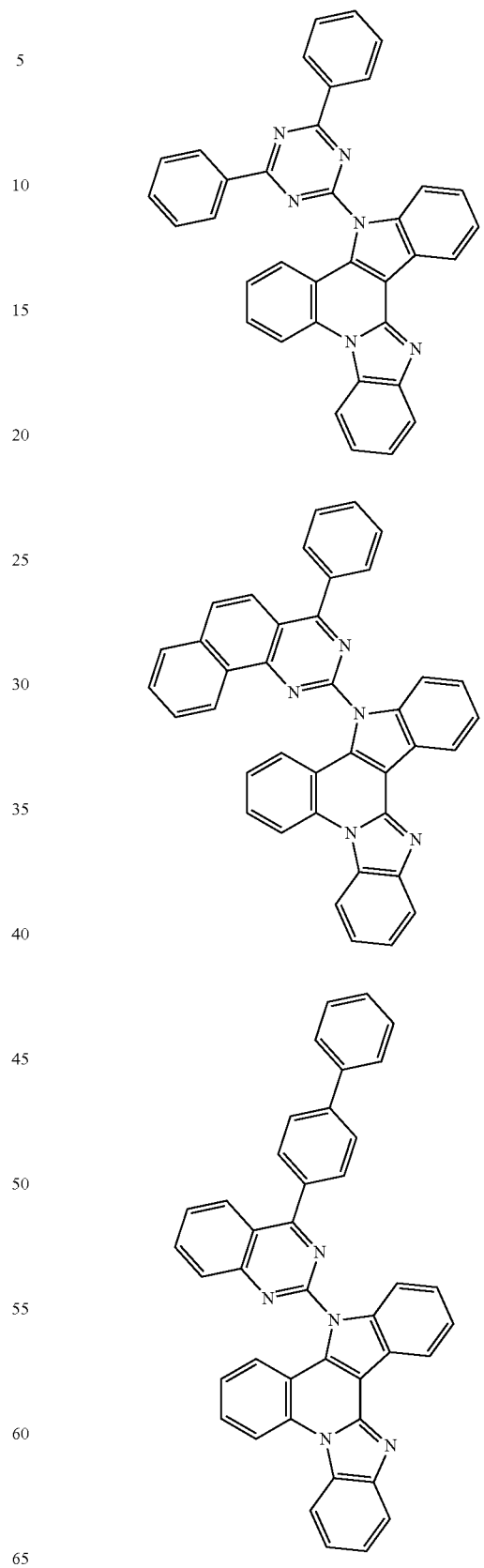

-continued
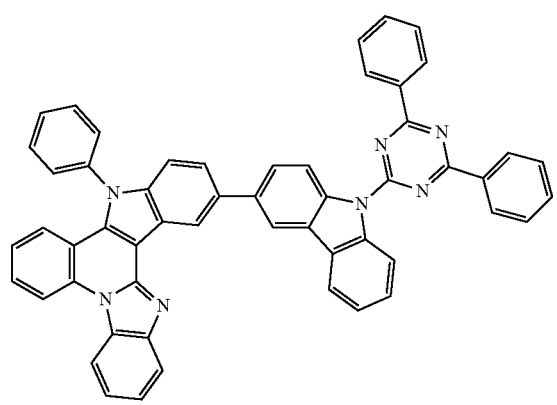 [SMILES: c1ccc(-c2nc(-c3ccccc3)nc(-n3c4ccccc4c4cc(-c5ccc6c(c5)c5c(c7ccccc7n7c8ccccc8nc57)n6-c5ccccc5)ccc43)n2)cc1]
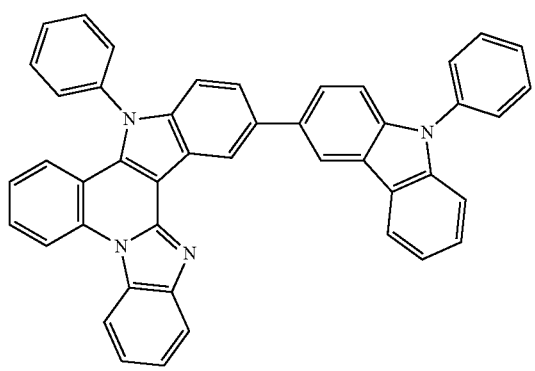 [SMILES: c1ccc(-n2c3ccccc3c3cc(-c4ccc5c(c4)c4c(c6ccccc6n6c7ccccc7nc46)n5-c4ccccc4)ccc32)cc1]
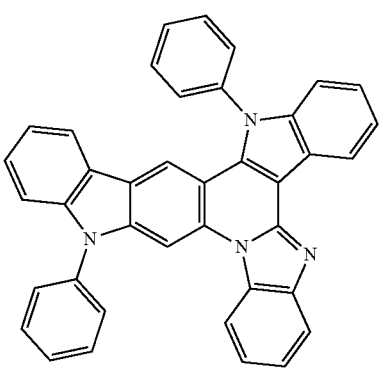 [SMILES: c1ccc(-n2c3ccccc3c3cc4c5c(c6ccccc6n5-c5ccccc5)c5nc6ccccc6n5c4cc32)cc1]
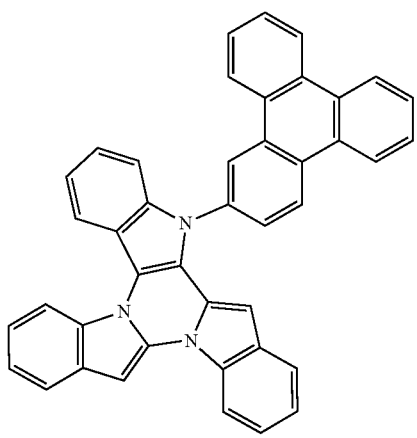 [SMILES: c1ccc2c(c1)cc1c3c(c4ccccc4n3-c3ccc4c5ccccc5c5ccccc5c4c3)n3c4ccccc4cc3n21]
-continued
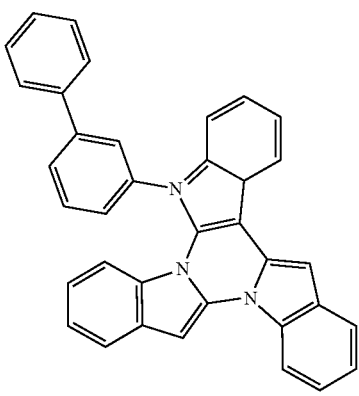
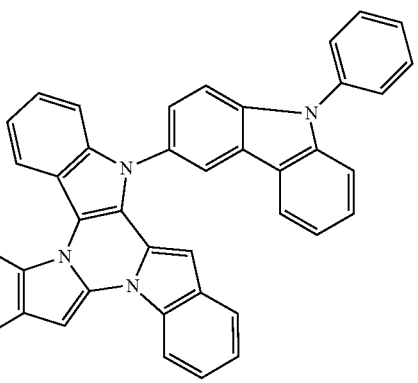
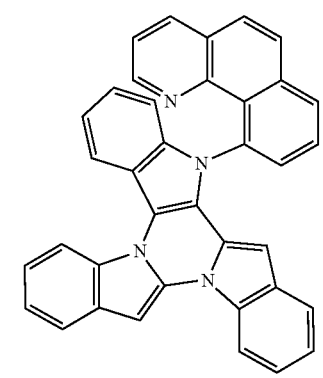 [SMILES: c1cnc2c(c1)ccc1cccc(-n3c4ccccc4c4c3c3cc5ccccc5n3c3cc5ccccc5n43)c12]
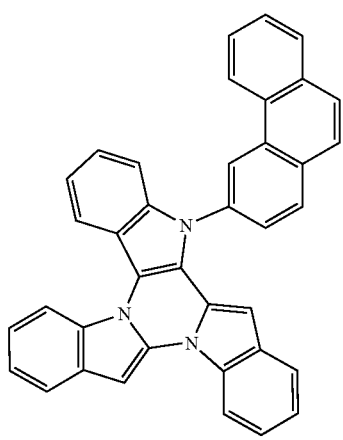 [SMILES: c1ccc2c(c1)ccc1ccc(-n3c4ccccc4c4c3c3cc5ccccc5n3c3cc5ccccc5n43)cc12]

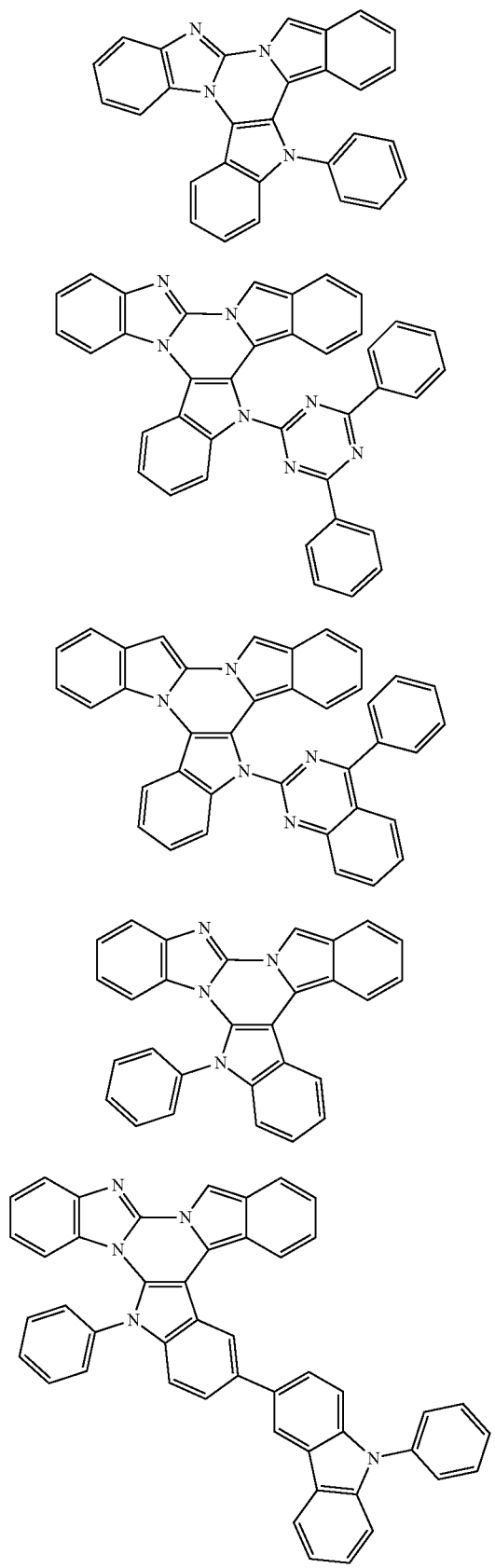

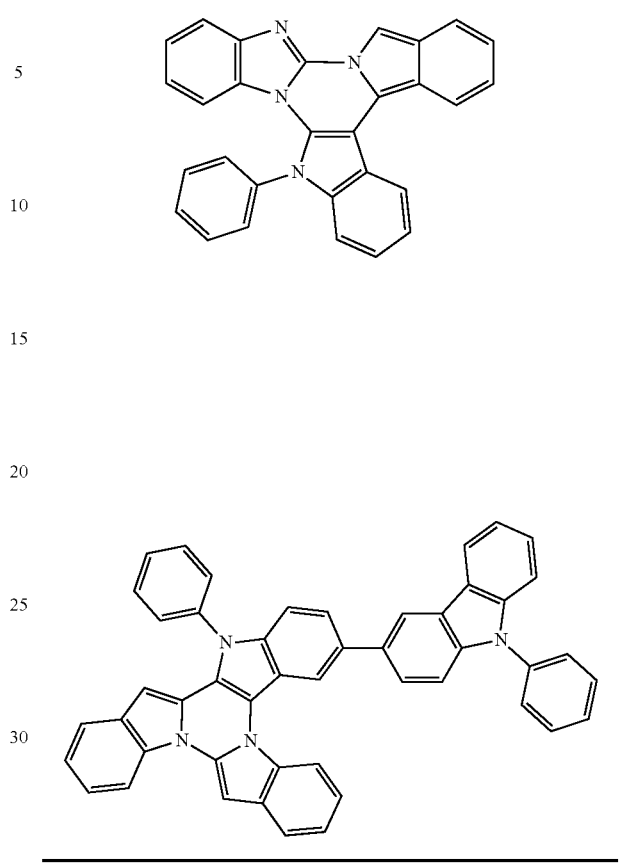

The base structure of the compounds of the invention can be prepared by the route outlined in schemes 1 to 4. Scheme 1 shows the synthesis of N-aryldichloroindole proceeding from indole. This can be reacted with 2-phenylindole or 2-phenylbenzimidazole (scheme 2) or with a corresponding 2-indolyl- or 2-benzimidazolylindole or -benzimidazole (scheme 3) to give the compounds of the invention. These may also be halogenated further, especially in the para position to the nitrogen on the indole ring, and converted to further derivatives, for example via a Buchwald coupling or a Suzuki coupling.

Scheme 1

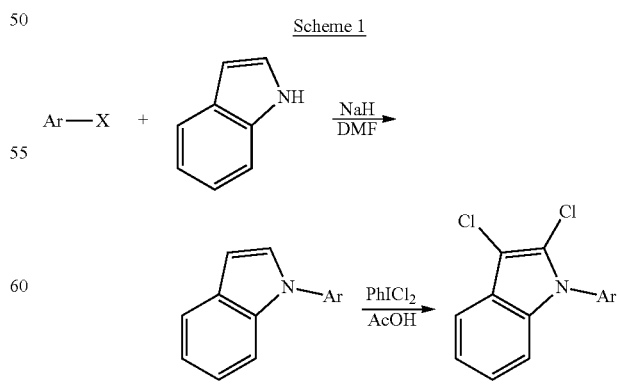

analogously to Journal of Organic Chemistry 2016, 81(22), 11081-11094

Scheme 2
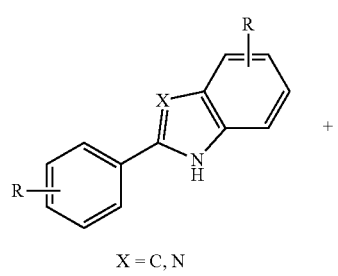
X = C, N
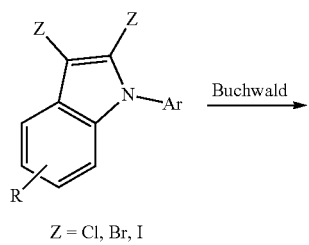
Z = Cl, Br, I
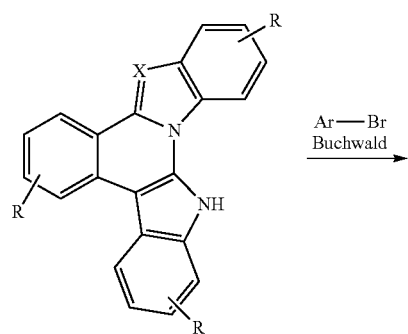
analogously to Org. Biomol. Chem. 2013, 11, 7966-7977
Scheme 3
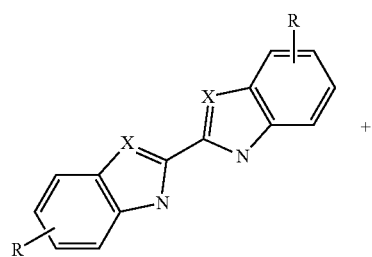
X = C, N
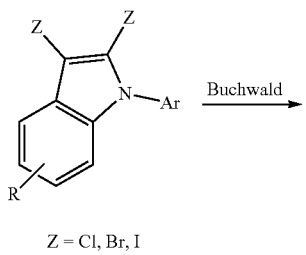
Z = Cl, Br, I
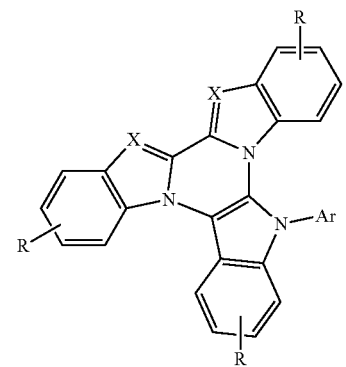
analogously to Org. Biomol. Chem. 2013, 11, 7966-7977
Scheme 4
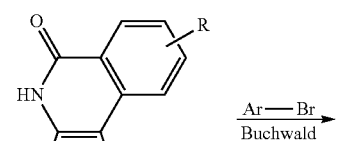
WO 2008/156879
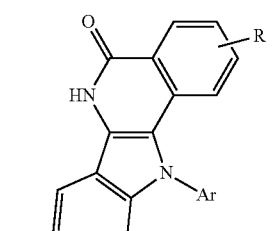
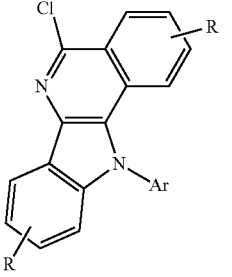 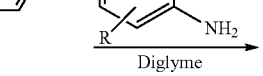

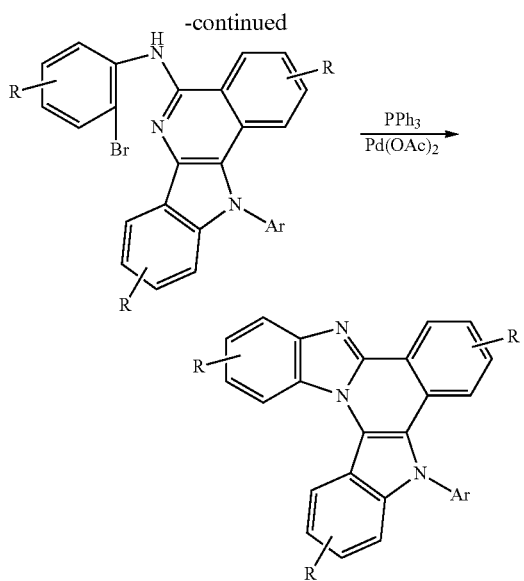

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device.

The present invention therefore further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound of the invention according to the above-detailed embodiments may be used in different layers, according to the exact structure. Preference is given to an organic electroluminescent device comprising a compound of formula (1) or the above-recited preferred embodiments in an emitting layer as matrix material for phosphorescent emitters or for emitters that exhibit TADF (thermally activated delayed fluorescence), especially for phosphorescent emitters. In this case, the organic electroluminescent device may contain an emitting layer, or it may contain a plurality of emitting layers, where at least one emitting layer contains at least one compound of the invention as matrix material. In addition, the compound of the invention can also be used in an electron transport layer and/or in a hole blocker layer and/or in a hole transport layer and/or in an exciton blocker layer.

The compound of the invention may additionally also be used as matrix for semiconductive light-emitting nanoparticles. The term "nano" here in the context of the present invention means a size in the range from 0.1 to 999 nm, preferably from 1 to 150 nm. In a preferred embodiment, the semiconductive light-emitting nanoparticle is a "quantum sized material". The term "quantum sized material" in the context of the present invention relates to the size of the semiconductor material itself without further compounds or any further surface modification that exhibits what is called the quantum confinement effect, as described, for example, in ISBN:978-3-662-44822-9. In one embodiment of the invention, the overall size of the quantum sized material is in the range from 1 to 100 nm, preferably from 1 to 30 nm and more preferably from 5 to 15 nm.

The "core" of the semiconductive light-emitting nanoparticle may vary. Suitable examples include CdS, CdSe, CdTe, ZnS, ZnSe, ZnSeS, ZnTe, ZnO, GaAs, GaP, GaSb, HgS, HgSe, HgSe, HgTe, InAs, InP, InPS, InPZnS, InPZn, InPGa, InSb, AlAs, AlP, AlSb, $Cu_2S$, $Cu_2Se$, $CuInS_2$, $CuInSe_2$, $Cu_2(ZnSn)S_4$, $Cu_2(InGa)S_4$, $TiO_2$, or a combination of the materials mentioned. In a preferred embodiment, the core of the semiconductive light-emitting particle contains one or more elements of group 13 and one or more elements of group 15 of the Periodic Table of the Elements, e.g. GaAs, GaP, GaSb, InAs, InP, InPS, InPZnS, InPZn, InPGa, InSb, AlAs, AlP, AlSb, $CuInS_2$, $CuInSe_2$, $Cu_2(InGa)S_4$ or a combination of the materials mentioned. More preferably, the core contains indium and phosphorus atoms, e.g. InP, InPS, InPZnS, InPZn or InPGa.

In a further embodiment of the invention, the nanoparticle contains one or more "shell layers" that contain a first element from group 12, 13 or 14 of the Periodic Table of the Elements and a second element from group 15 or 16 of the Periodic Table of the Elements. Preferably, all shell layers contain a first element from group 12, 13 or 14 of the Periodic Table of the Elements and a second element from group 15 or 16 of the Periodic Table of the Elements. In a preferred embodiment of the invention, at least one of the shell layers contains a first element from group 12 and a second element from group 16 of the Periodic Table of the Elements, e.g. CdS, CdZnS, ZnS, ZnSe, ZnSSe, ZnSSeTe, CdS/ZnS, ZnSe/ZnS or ZnS/ZnSe. More preferably, all shell layers contain a first element from group 12 and a second element from group 16 of the Periodic Table of the Elements.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state>1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, biscarbazole derivatives, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, or dibenzofuran derivatives, for example according to WO 2015/169412, WO 2016/015810, WO 2016/023608, WO 2017/148564 or WO 2017/148565. It is likewise possible for a further phosphorescent emitter having shorter-wavelength emission than the actual emitter to be present as co-host in the mixture. Also suitable in combination with the compound of the invention as co-matrix material are compounds which have a large bandgap and themselves take part at least not to a significant degree, if any at all, in the charge transport of the emitting layer. Such materials are preferably pure hydrocarbons. Examples of such materials can be found, for example, in WO 2009/124627, WO 2010/108579 or WO 2010/006680.

Preferred co-host materials are triarylamine derivatives, especially monoamines, indenocarbazole derivatives, 4-spirocarbazole derivatives, carbazole derivatives and biscarbazole derivatives.

Preferred triarylamine derivatives which are used as co-host materials together with the compounds of the invention are selected from the compounds of the following formula (TA-1):

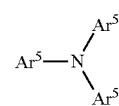

Formula (TA-1)

where $Ar^5$ is the same or different at each instance and is an aromatic or heteroaromatic ring system which has 6 to 40 carbon atoms and may be substituted in each case by one or more R radicals where R has the definition given above. Preferably, $Ar^5$ is the same or different at each instance and is an aromatic or heteroaromatic ring system which has 5 to 24, preferably 5 to 12, aromatic ring atoms and may be substituted in each case by one or more R radicals, but is preferably unsubstituted.

Examples of suitable Ar⁵ groups are selected from the group consisting of phenyl, ortho-, meta- or para-biphenyl, terphenyl, especially branched terphenyl, quaterphenyl, insbesondere branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more R radicals, but are preferably unsubstituted.

In a preferred embodiment of the compounds of the formula (TA-1), at least one Ar⁵ group is selected from a biphenyl group, which may be an ortho-, meta- or para-biphenyl group. In a further preferred embodiment of the compounds of the formula (TA-1), at least one Ar⁵ group is selected from a fluorene group or spirobifluorene group, where these groups may each be bonded to the nitrogen atom in the 1, 2, 3 or 4 position. In yet a further preferred embodiment of the compounds of the formula (TA-1), at least one Ar⁵ group is selected from a phenylene or biphenyl group, where the group is an ortho-, meta- or para-bonded group, substituted by a dibenzofuran group, a dibenzothiophene group or a carbazole group, especially a dibenzofuran group, where the dibenzofuran or dibenzothiophene group is bonded to the phenylene or biphenyl group via the 1, 2, 3 or 4 position and where the carbazole group is bonded to the phenylene or biphenyl group via the 1, 2, 3 or 4 position or via the nitrogen atom.

In a particularly preferred embodiment of the compounds of the formula (TA-1), one Ar⁵ group is selected from a fluorene or spirobifluorene group, especially a 4-fluorene or 4-spirobifluorene group, and one Ar⁵ group is selected from a biphenyl group, especially a para-biphenyl group, or a fluorene group, especially a 2-fluorene group, and the third Ar⁵ group is selected from a para-phenylene group or a para-biphenyl group, substituted by a dibenzofuran group, especially a 4-dibenzofuran group, or a carbazole group, especially an N-carbazole group or a 3-carbazole group.

Preferred indenocarbazole derivatives which are used as co-host materials together with the compounds of the invention are selected from the compounds of the following formula (TA-2):

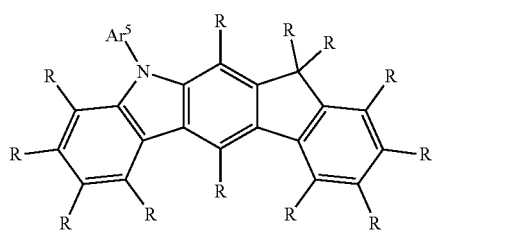

Formula (TA-2)

where Ar⁵ and R have the definitions detailed above. Preferred embodiments of the Ar⁵ group are the structures detailed above.

A preferred embodiment of the compounds of the formula (TA-2) is the compounds of the following formula (TA-2a):

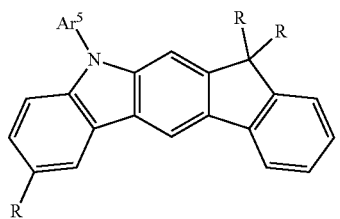

Formula (TA-2a)

where Ar⁵ and R have the definitions detailed above. The two R groups bonded to the indeno carbon atom here are preferably the same or different and are each an alkyl group having 1 to 4 carbon atoms, especially methyl groups, or an aromatic ring system having 6 to 12 carbon atoms, especially phenyl groups. More preferably, the two R groups bonded to the indeno carbon atom are methyl groups. Further preferably, the substituent R¹ bonded to the indenocarbazole base skeleton in formula (TA-2a) is H or a carbazole group which may be bonded to the indenocarbazole base skeleton via the 1, 2, 3 or 4 position or via the nitrogen atom, especially via the 3 position.

Preferred 4-spirocarbazole derivatives which are used as co-host materials together with the compounds of the invention are selected from the compounds of the following formula (TA-3):

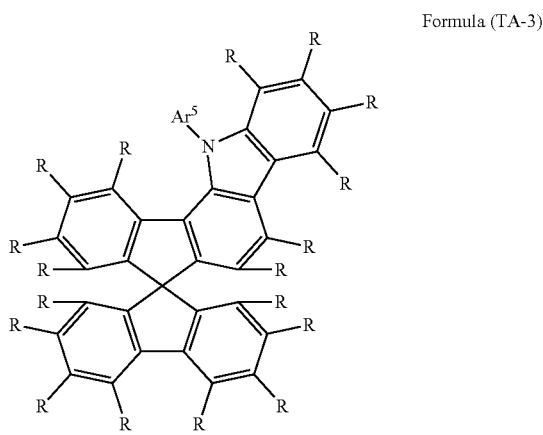

Formula (TA-3)

where Ar⁵ and R have the definitions detailed above.

A preferred embodiment of the compounds of the formula (TA-3) is the compounds of the following formula (TA-3a):

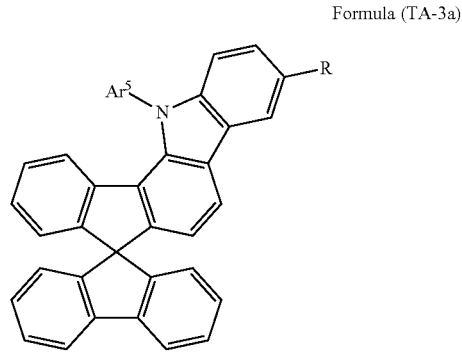

Formula (TA-3a)

where Ar and R⁵ have the definitions detailed above.

Preferred biscarbazole derivatives that can be used as co-host materials together with the compounds of the invention are selected from the compounds of the following formula (TA-4):

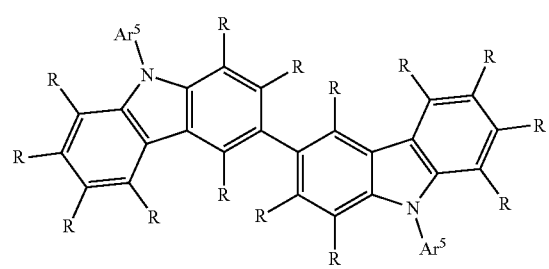

Formula (TA-4)

where Ar⁵ and R have the definitions detailed above.

A preferred embodiment of the compounds of the formula (TA-4) is the compounds of the following formula (TA-4a):

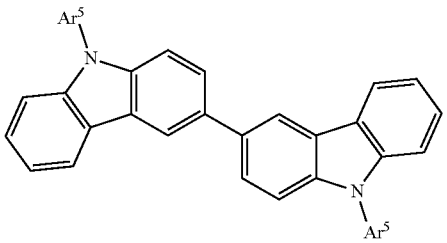

Formula (TA-4)

where Ar⁵ has the definitions detailed above.

Examples of suitable biscarbazole derivatives are the materials shown in the following table:

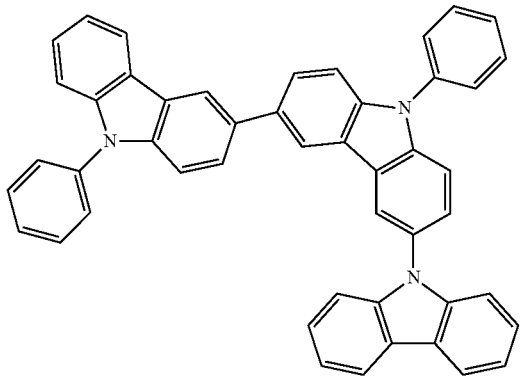 [SMILES: c1ccc(-n2c3ccccc3c3cc(-c4ccc5c(c4)c4cc(-n6c7ccccc7c7ccccc76)ccc4n5-c4ccccc4)ccc32)cc1]

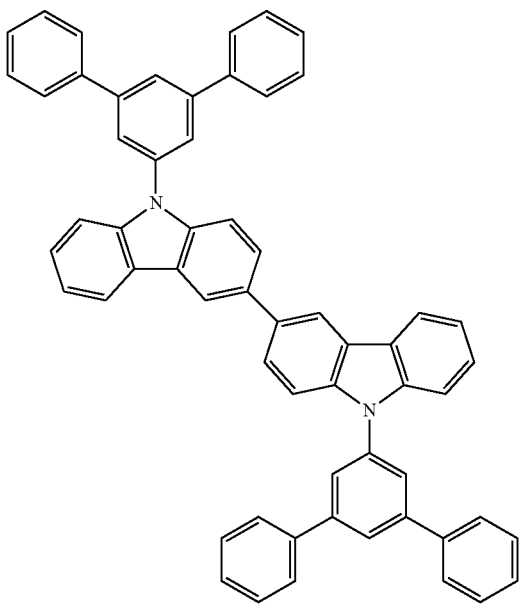 [SMILES: c1ccc(-c2cc(-c3ccccc3)cc(-n3c4ccccc4c4cc(-c5ccc6c(c5)c5ccccc5n6-c5cc(-c6ccccc6)cc(-c6ccccc6)c5)ccc43)c2)cc1]

-continued
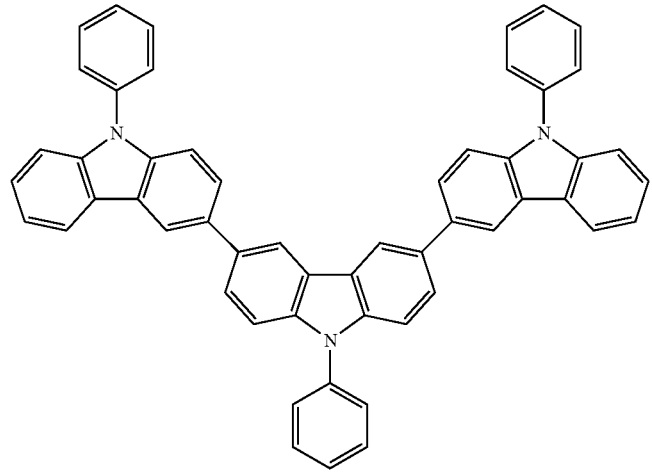 [SMILES: c1ccc(-n2c3ccccc3c3cc(-c4ccc5c(c4)c4cc(-c6ccc7c(c6)c6ccccc6n7-c6ccccc6)ccc4n5-c4ccccc4)ccc32)cc1]
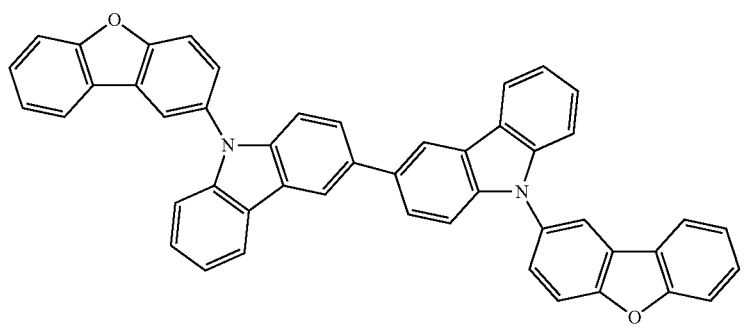 [SMILES: c1ccc2c(c1)oc1ccc(-n3c4ccccc4c4cc(-c5ccc6c(c5)c5ccccc5n6-c5ccc6oc7ccccc7c6c5)ccc43)cc12]
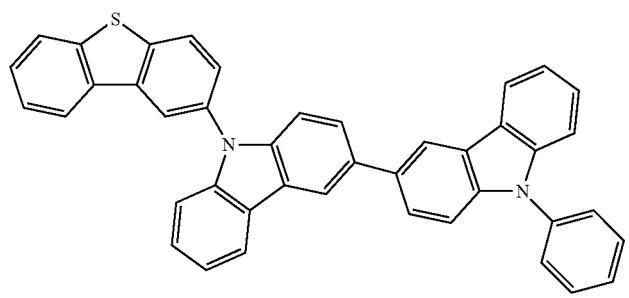 [SMILES: c1ccc(-n2c3ccccc3c3cc(-c4ccc5c(c4)c4ccccc4n5-c4ccc5sc6ccccc6c5c4)ccc32)cc1]
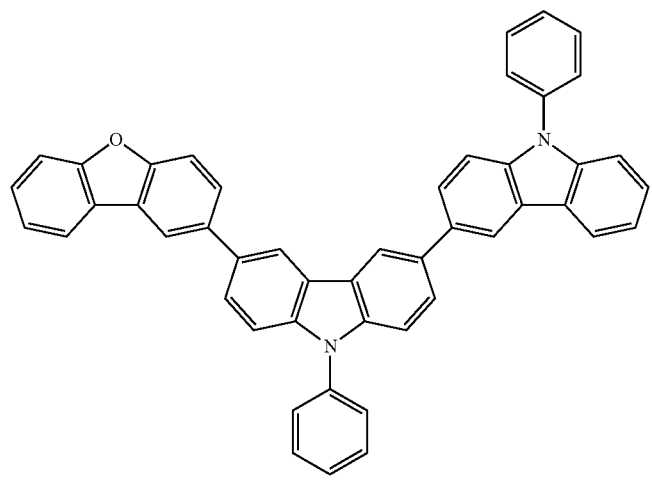 [SMILES: c1ccc(-n2c3ccccc3c3cc(-c4ccc5c(c4)c4cc(-c6ccc7oc8ccccc8c7c6)ccc4n5-c4ccccc4)ccc32)cc1]

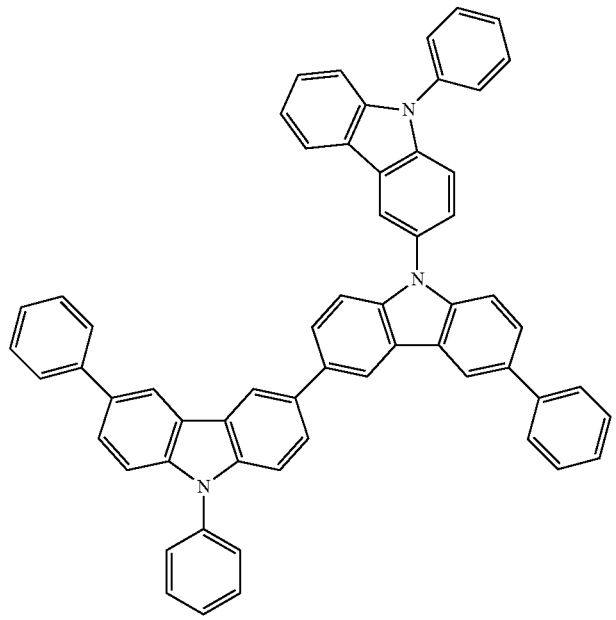 [SMILES: c1ccc(-c2ccc3c(c2)c2cc(-c4ccc5c(c4)c4cc(-c6ccccc6)ccc4n5-c4ccc5c(c4)c4ccccc4n5-c4ccccc4)ccc2n3-c2ccccc2)cc1]
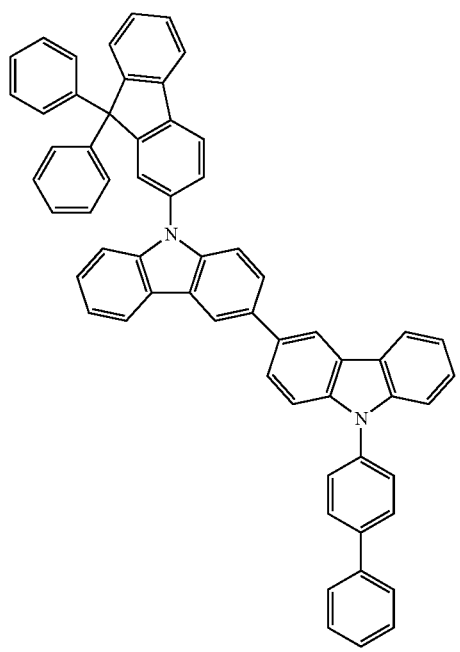 [SMILES: c1ccc(-c2ccc(-n3c4ccccc4c4cc(-c5ccc6c(c5)c5ccccc5n6-c5ccc6c(c5)C(c5ccccc5)(c5ccccc5)c5ccccc5-6)ccc43)cc2)cc1]

-continued
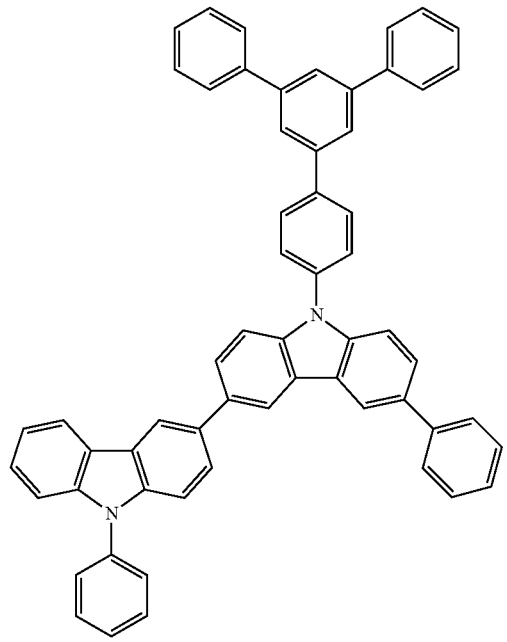 [SMILES: c1ccc(-c2cc(-c3ccccc3)cc(-c3ccc(-n4c5ccc(-c6ccccc6)cc5c5cc(-c6ccc7c(c6)c6ccccc6n7-c6ccccc6)ccc54)cc3)c2)cc1]
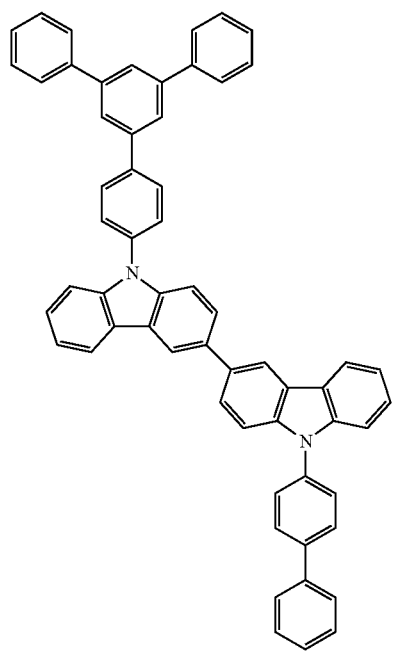 [SMILES: c1ccc(-c2ccc(-n3c4ccccc4c4cc(-c5ccc6c(c5)c5ccccc5n6-c5ccc(-c6cc(-c7ccccc7)cc(-c7ccccc7)c6)cc5)ccc43)cc2)cc1]

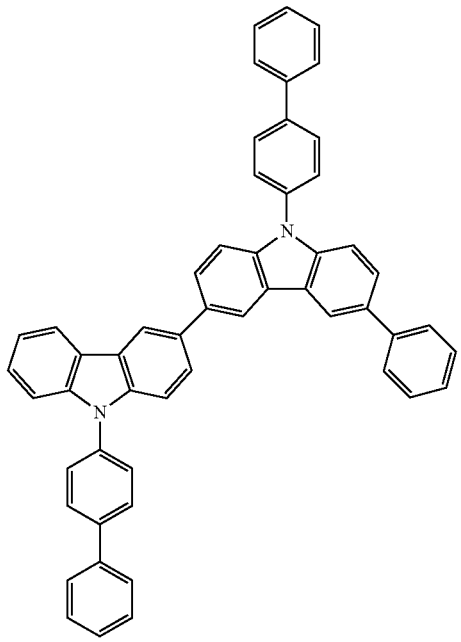 [SMILES: c1ccc(-c2ccc(-n3c4ccccc4c4cc(-c5ccc6c(c5)c5cc(-c7ccccc7)ccc5n6-c5ccc(-c6ccccc6)cc5)ccc43)cc2)cc1]
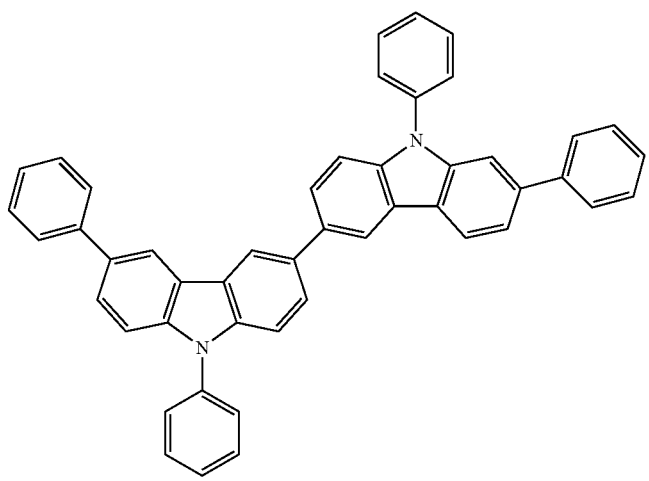 [SMILES: c1ccc(-c2ccc3c(c2)c2cc(-c4ccc5c(c4)c4ccc(-c6ccccc6)cc4n5-c4ccccc4)ccc2n3-c2ccccc2)cc1]
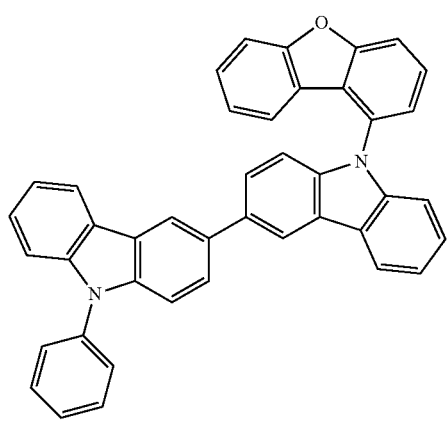 [SMILES: c1ccc(-n2c3ccccc3c3cc(-c4ccc5c(c4)c4ccccc4n5-c4cccc5oc6ccccc6c45)ccc32)cc1]

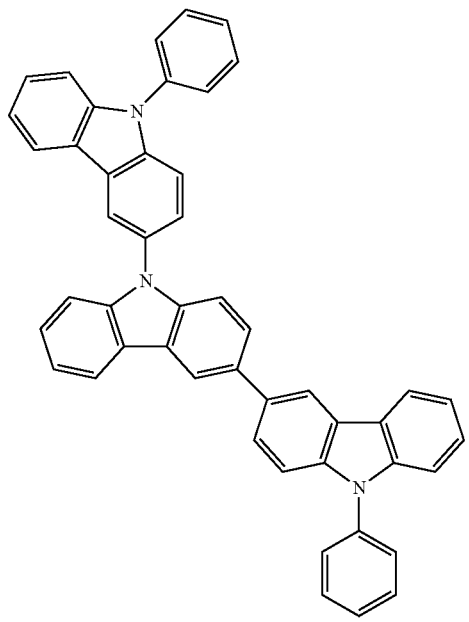 [SMILES: c1ccc(-n2c3ccccc3c3cc(-c4ccc5c(c4)c4ccccc4n5-c4ccc5c(c4)c4ccccc4n5-c4ccccc4)ccc32)cc1]
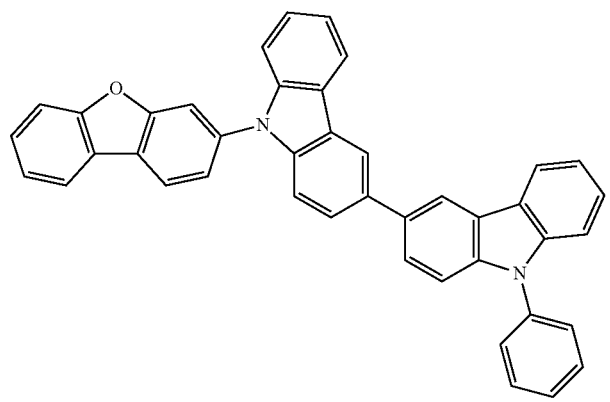 [SMILES: c1ccc(-n2c3ccccc3c3cc(-c4ccc5c(c4)c4ccccc4n5-c4ccc5c(c4)oc4ccccc45)ccc32)cc1]
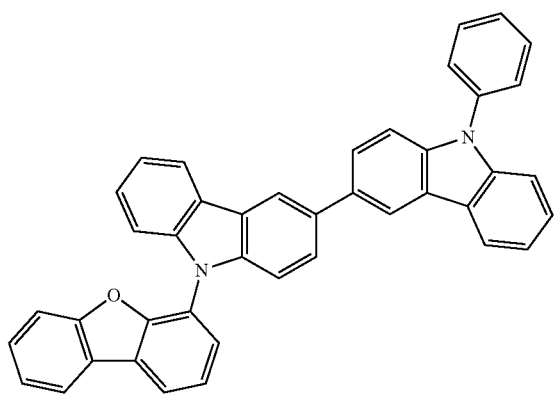 [SMILES: c1ccc(-n2c3ccccc3c3cc(-c4ccc5c(c4)c4ccccc4n5-c4cccc5c4oc4ccccc45)ccc32)cc1]

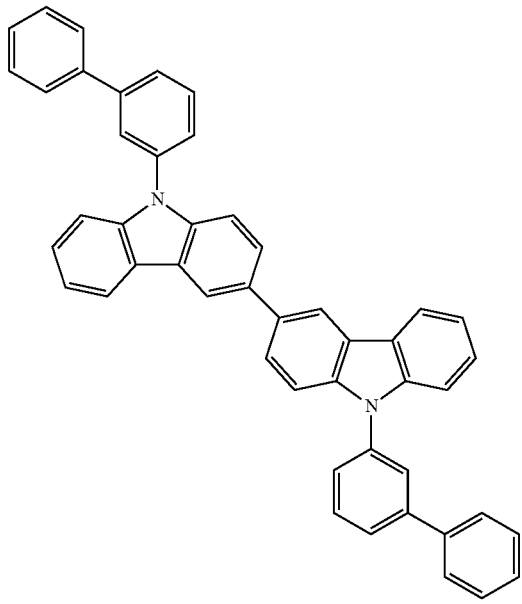 [SMILES: c1ccc(-c2cccc(-n3c4ccccc4c4cc(-c5ccc6c(c5)c5ccccc5n6-c5cccc(-c6ccccc6)c5)ccc43)c2)cc1]
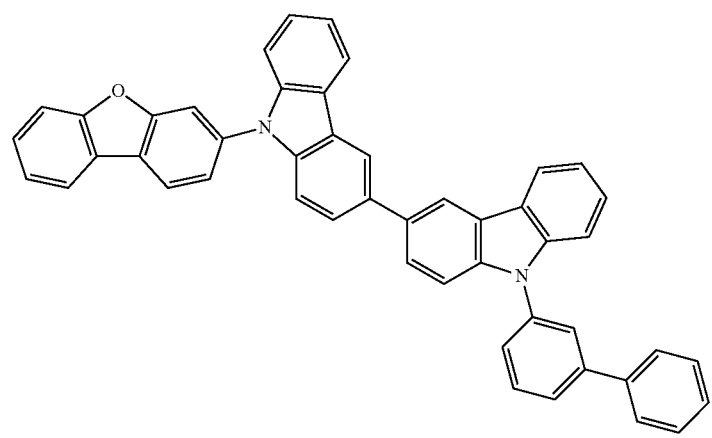 [SMILES: c1ccc(-c2cccc(-n3c4ccccc4c4cc(-c5ccc6c(c5)c5ccccc5n6-c5ccc6c(c5)oc5ccccc56)ccc43)c2)cc1]

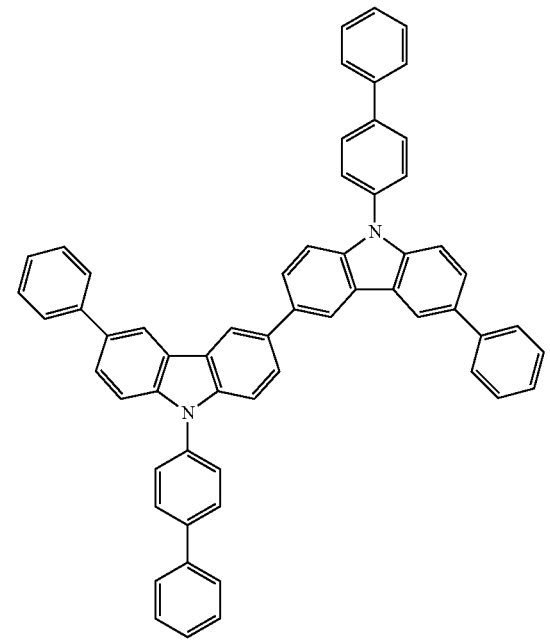 [SMILES: c1ccc(-c2ccc(-n3c4ccc(-c5ccccc5)cc4c4cc(-c5ccc6c(c5)c5cc(-c7ccccc7)ccc5n6-c5ccc(-c6ccccc6)cc5)ccc43)cc2)cc1]
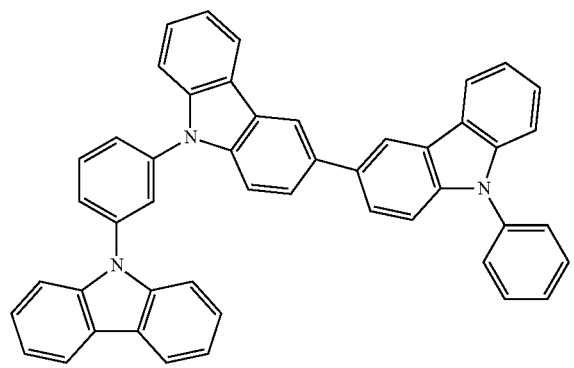 [SMILES: c1ccc(-n2c3ccccc3c3cc(-c4ccc5c(c4)c4ccccc4n5-c4cccc(-n5c6ccccc6c6ccccc65)c4)ccc32)cc1]
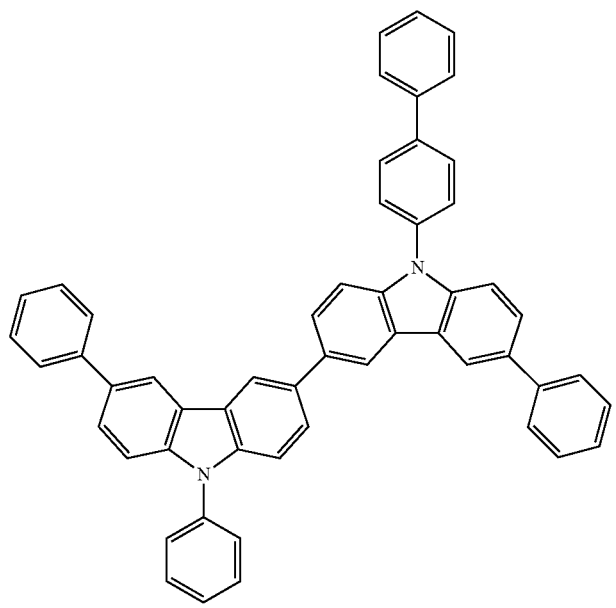 [SMILES: c1ccc(-c2ccc(-n3c4ccc(-c5ccccc5)cc4c4cc(-c5ccc6c(c5)c5cc(-c7ccccc7)ccc5n6-c5ccccc5)ccc43)cc2)cc1]

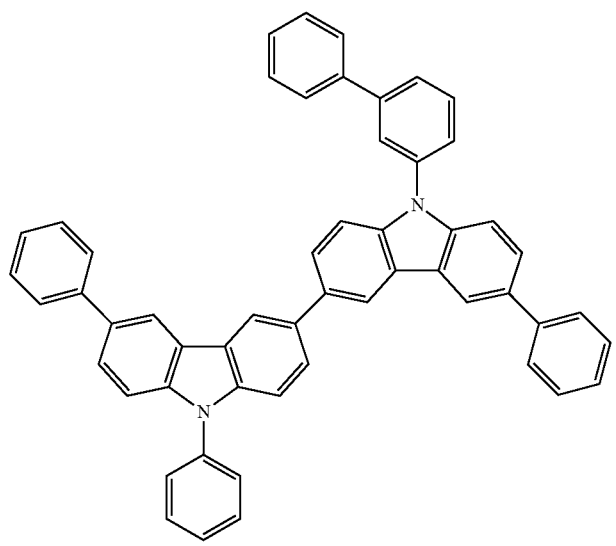 [SMILES: c1ccc(-c2cccc(-n3c4ccc(-c5ccccc5)cc4c4cc(-c5ccc6c(c5)c5cc(-c7ccccc7)ccc5n6-c5ccccc5)ccc43)c2)cc1]
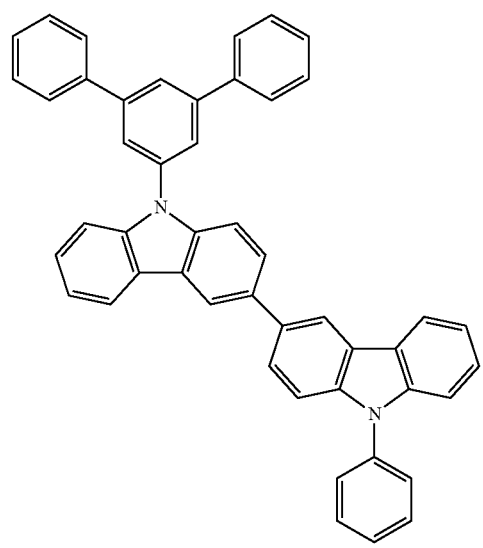 [SMILES: c1ccc(-c2cc(-c3ccccc3)cc(-n3c4ccccc4c4cc(-c5ccc6c(c5)c5ccccc5n6-c5ccccc5)ccc43)c2)cc1]

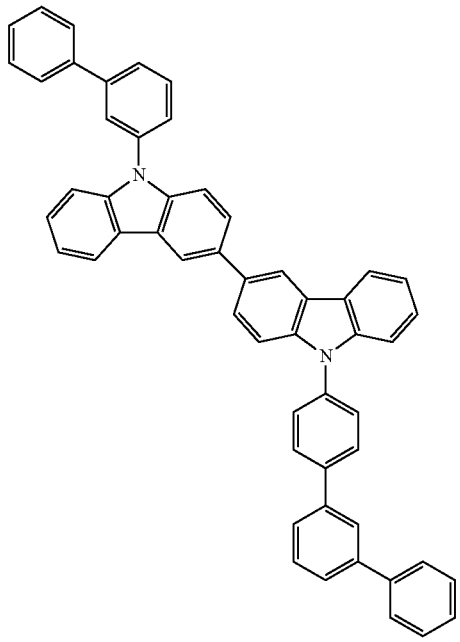 [SMILES: c1ccc(-c2cccc(-c3ccc(-n4c5ccccc5c5cc(-c6ccc7c(c6)c6ccccc6n7-c6cccc(-c7ccccc7)c6)ccc54)cc3)c2)cc1]
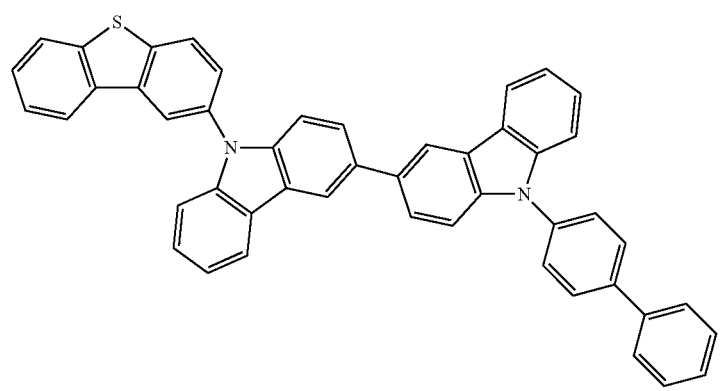 [SMILES: c1ccc(-c2ccc(-n3c4ccccc4c4cc(-c5ccc6c(c5)c5ccccc5n6-c5ccc6sc7ccccc7c6c5)ccc43)cc2)cc1]
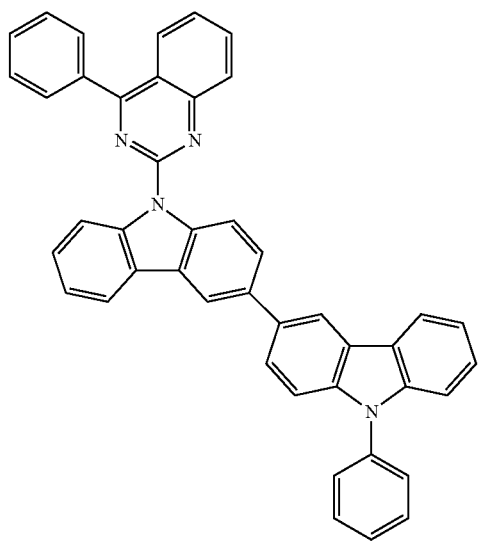 [SMILES: c1ccc(-c2nc(-n3c4ccccc4c4cc(-c5ccc6c(c5)c5ccccc5n6-c5ccccc5)ccc43)nc3ccccc23)cc1]

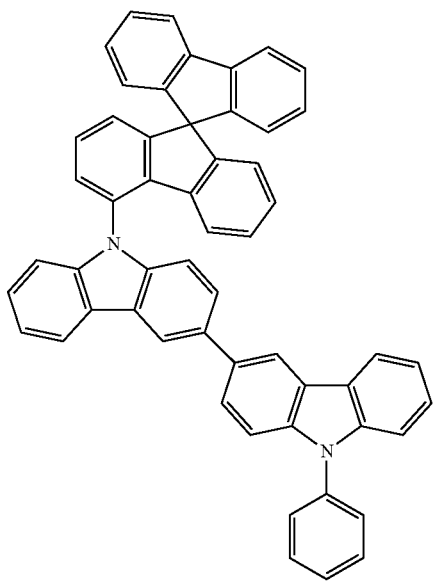 [SMILES: c1ccc(-n2c3ccccc3c3cc(-c4ccc5c(c4)c4ccccc4n5-c4cccc5c4-c4ccccc4C54c5ccccc5-c5ccccc54)ccc32)cc1]
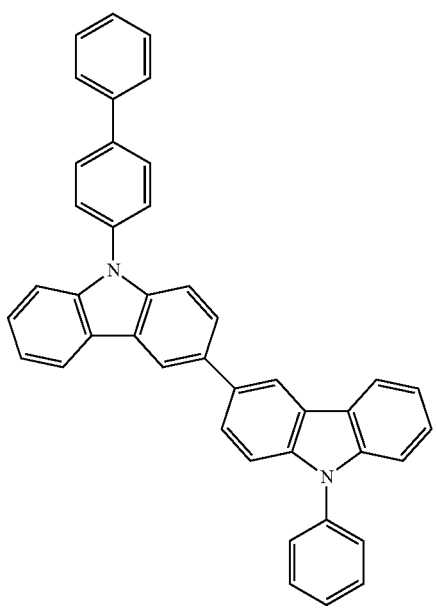 [SMILES: c1ccc(-c2ccc(-n3c4ccccc4c4cc(-c5ccc6c(c5)c5ccccc5n6-c5ccccc5)ccc43)cc2)cc1]

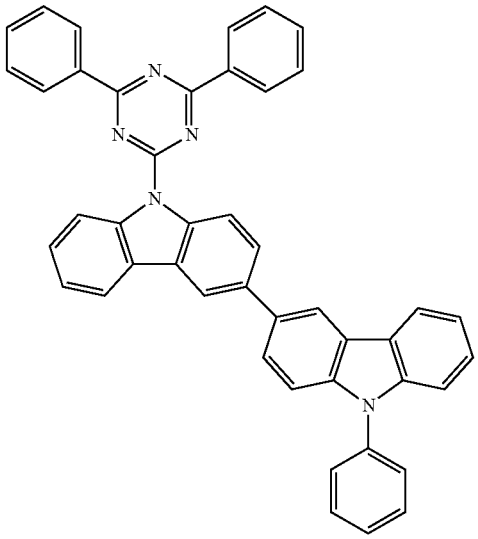 [SMILES: c1ccc(-c2nc(-c3ccccc3)nc(-n3c4ccccc4c4cc(-c5ccc6c(c5)c5ccccc5n6-c5ccccc5)ccc43)n2)cc1]

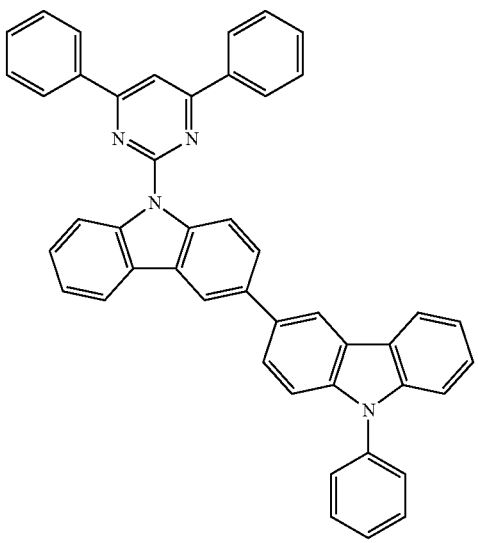 [SMILES: c1ccc(-c2cc(-c3ccccc3)nc(-n3c4ccccc4c4cc(-c5ccc6c(c5)c5ccccc5n6-c5ccccc5)ccc43)n2)cc1]

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439 and WO 2018/011186. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are adduced below.

-continued
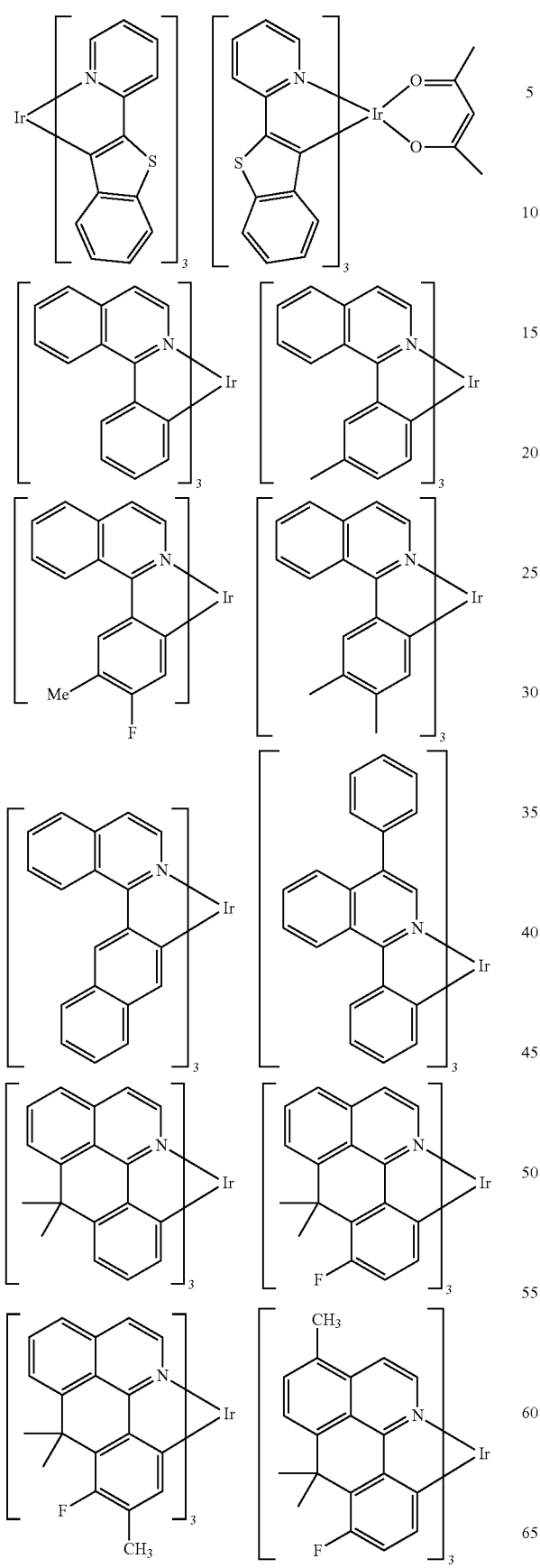
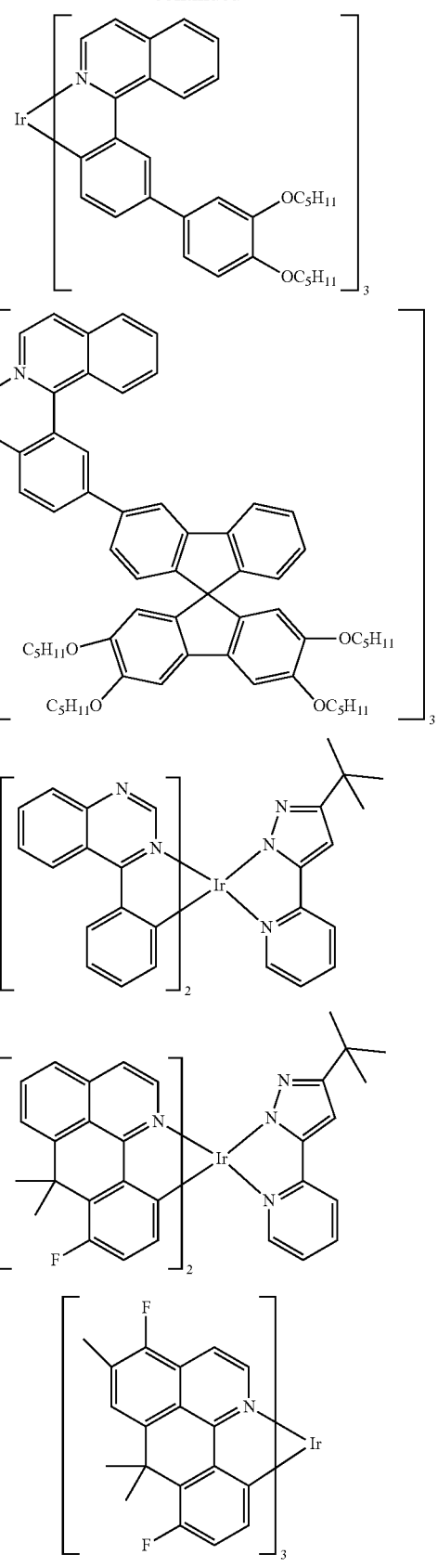

-continued
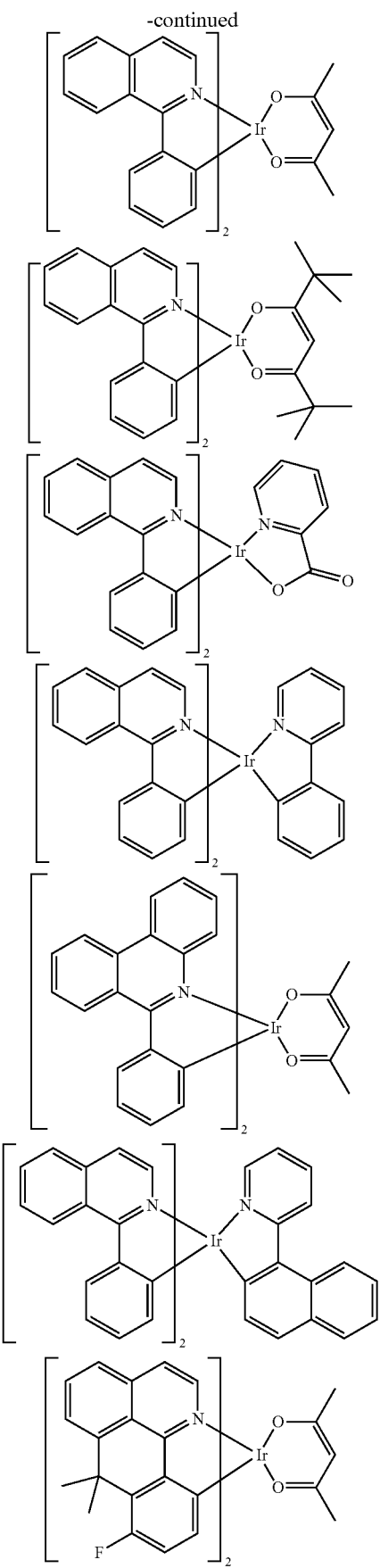
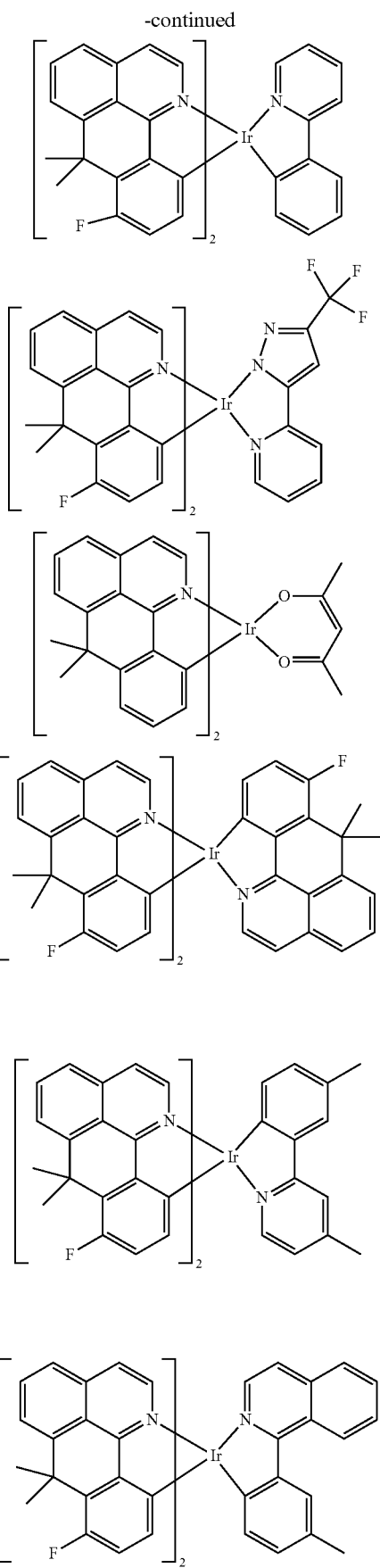

145
-continued
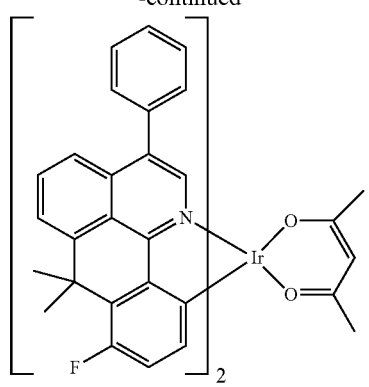
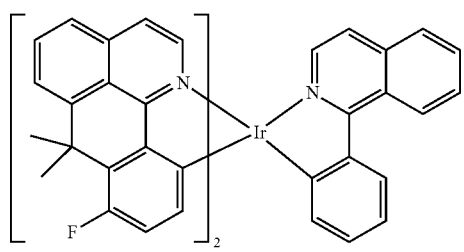
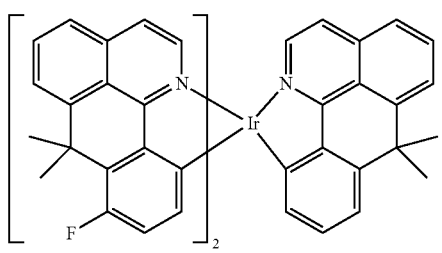
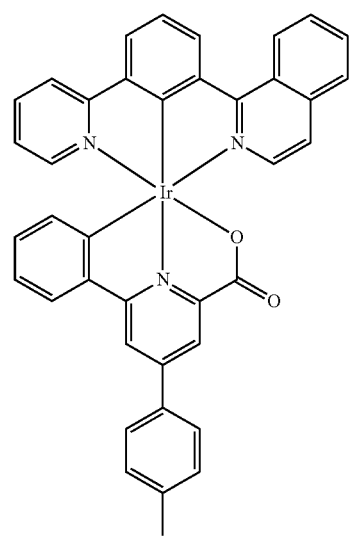
146
-continued
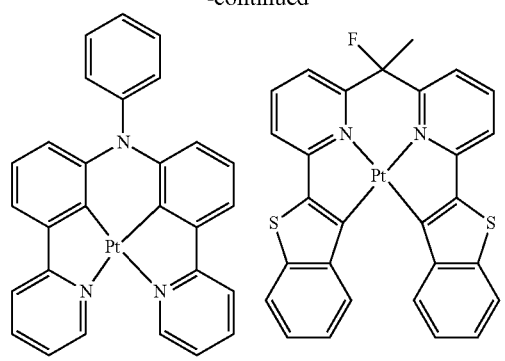
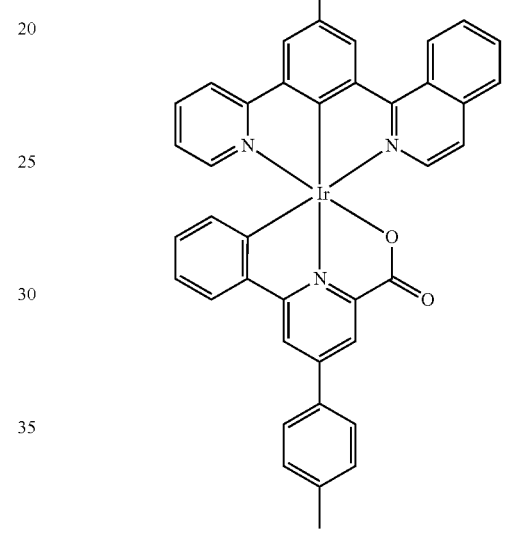
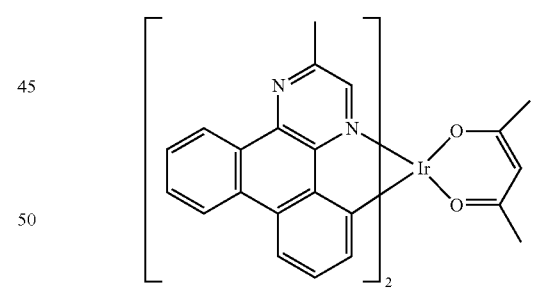
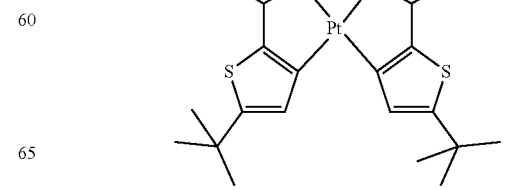

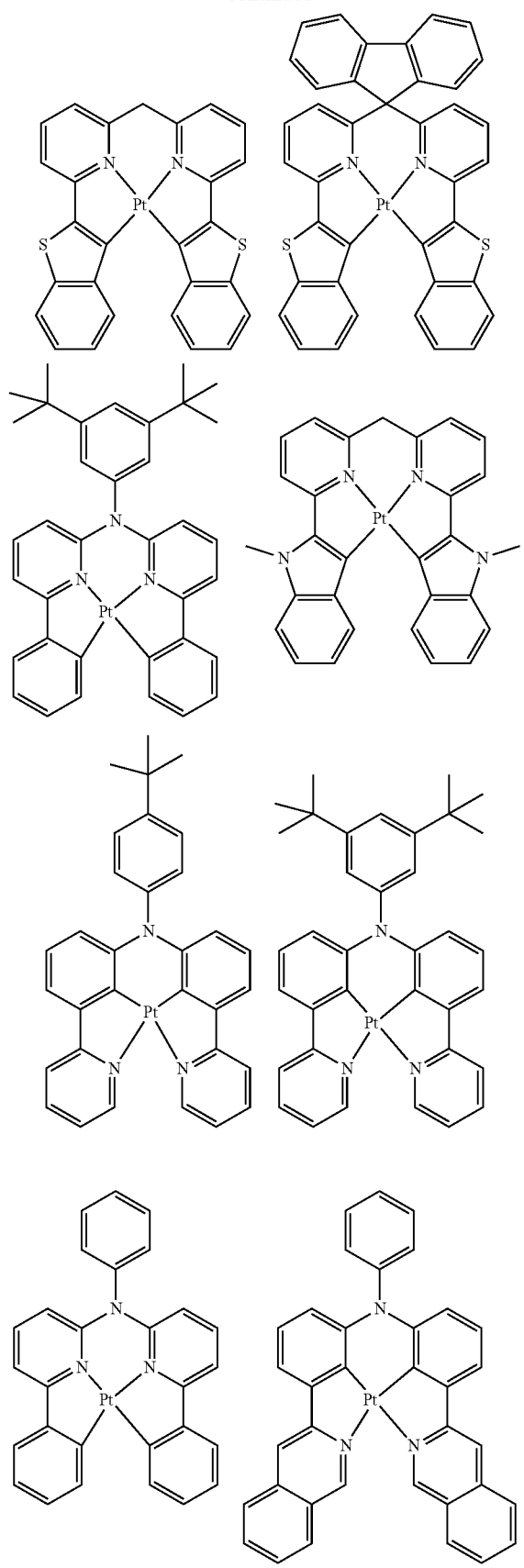
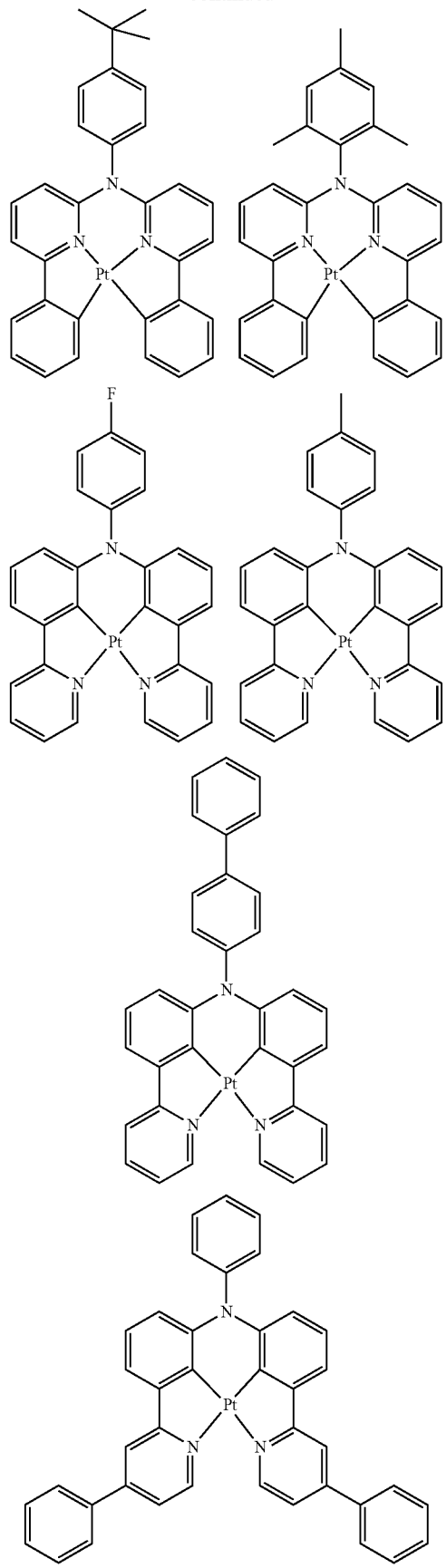

149
-continued
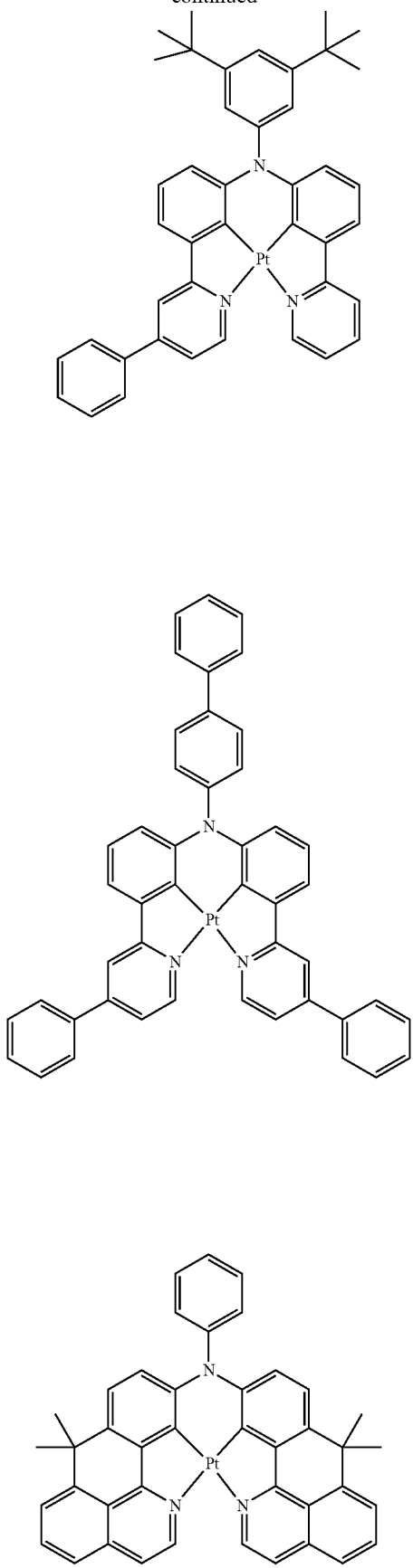
150
-continued
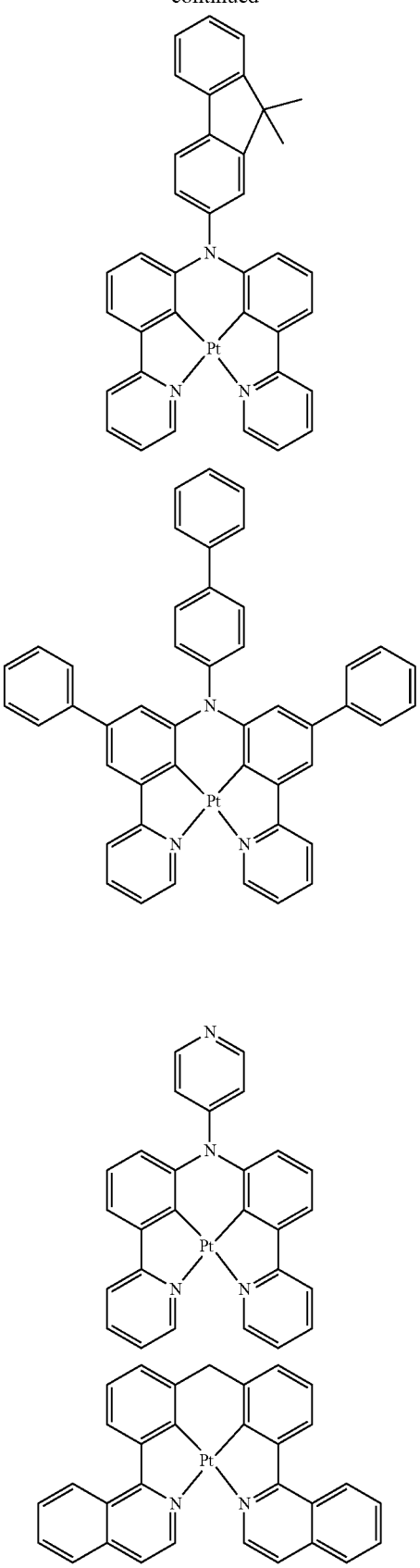

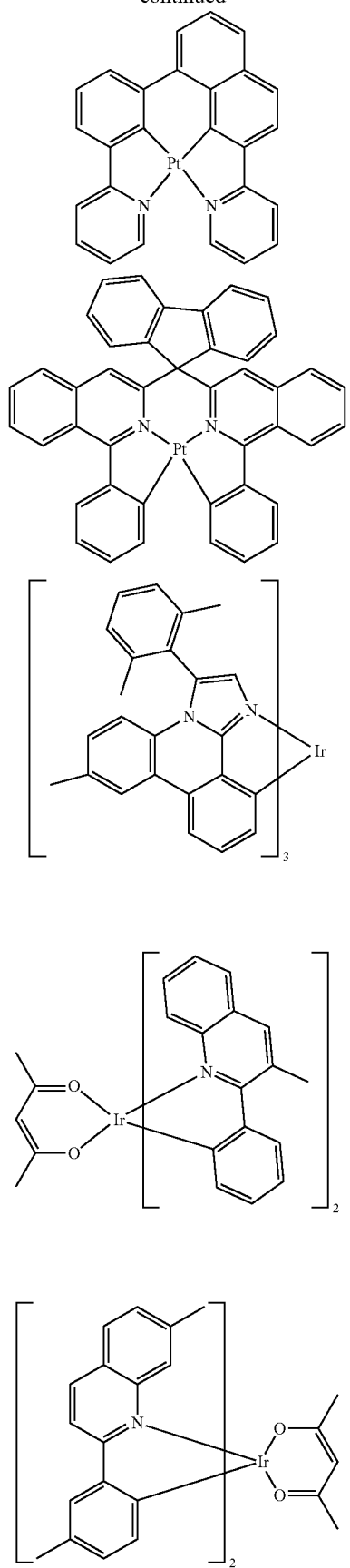
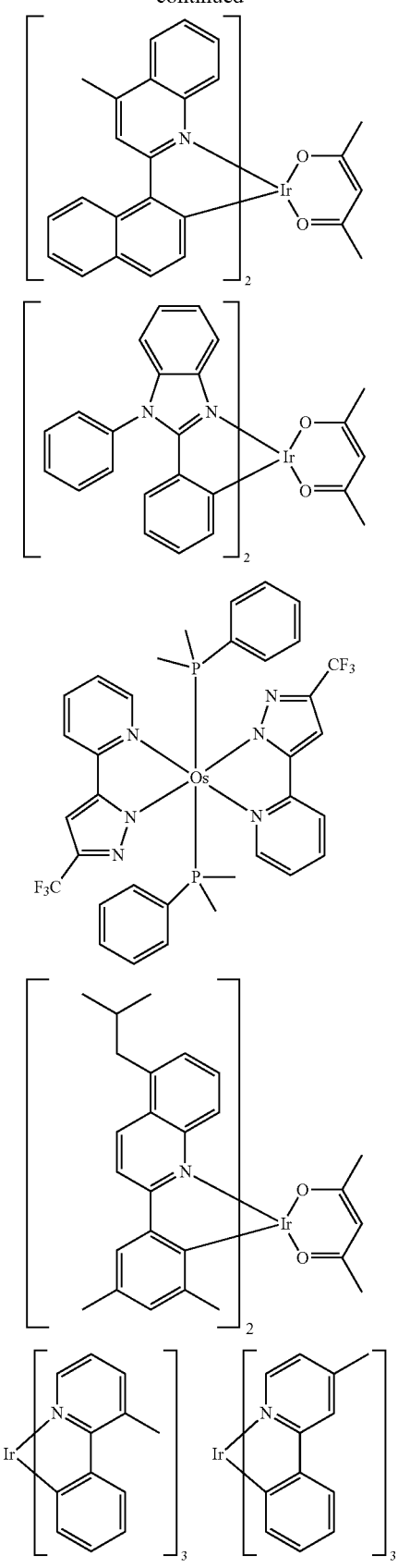

153
-continued
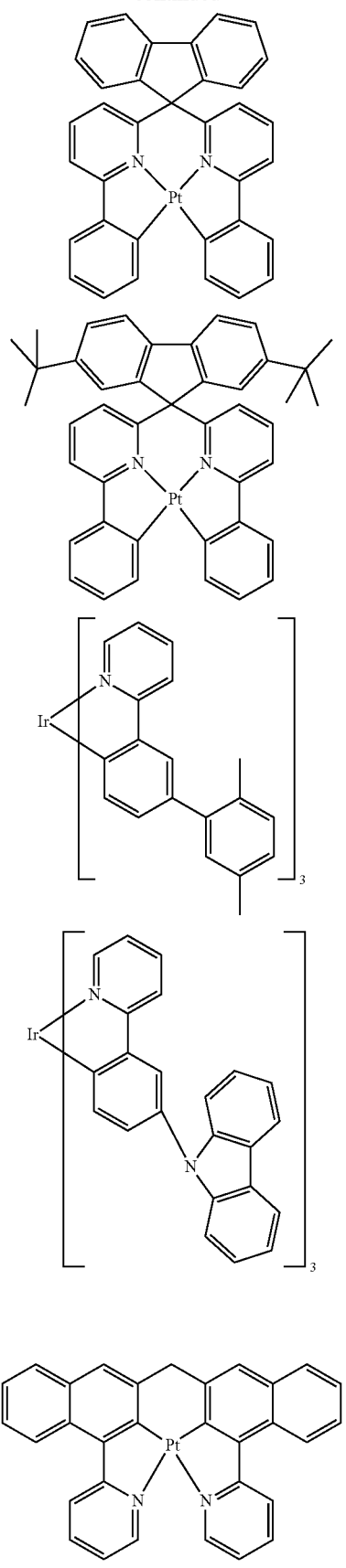
154
-continued
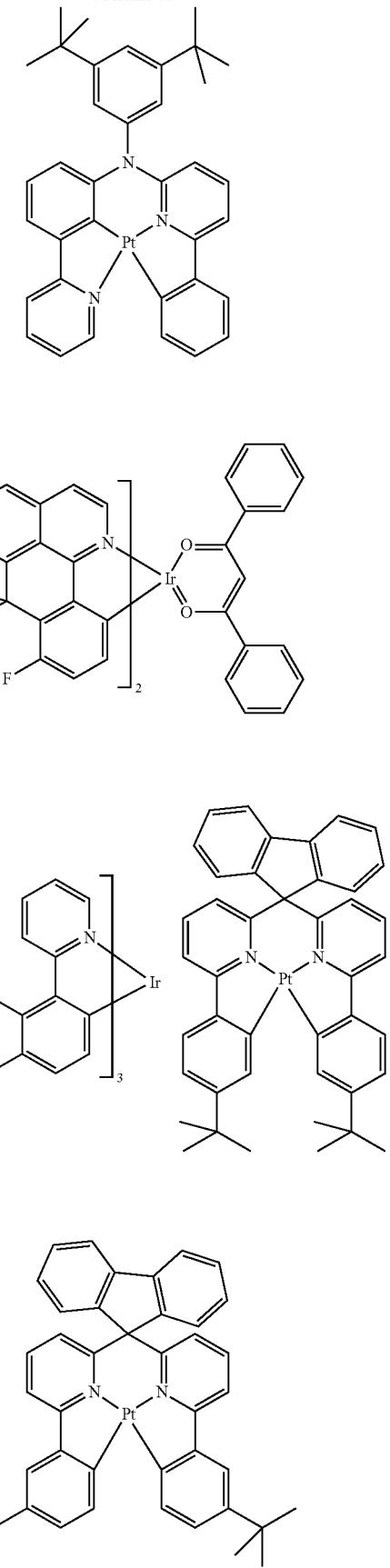

155
-continued
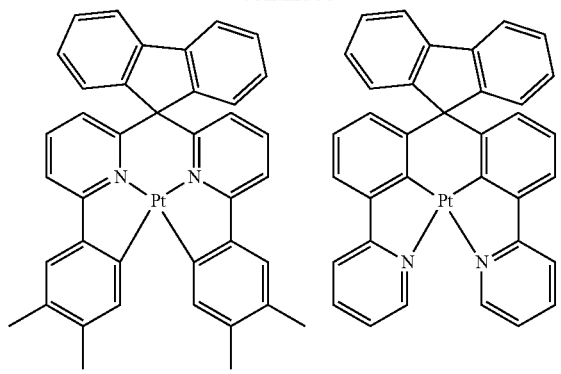
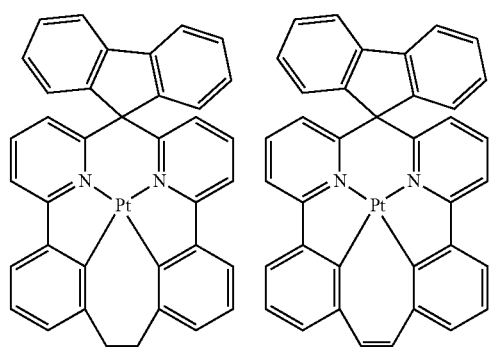
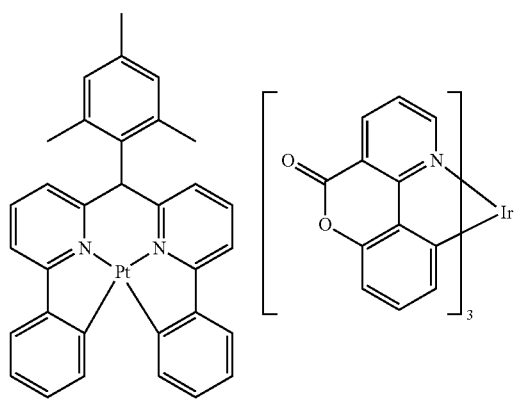
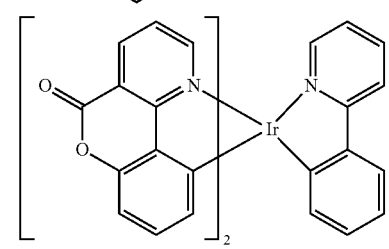
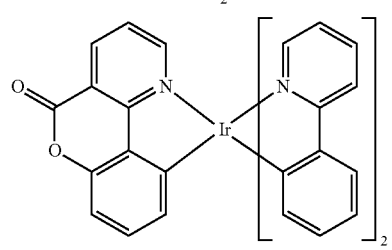
156
-continued
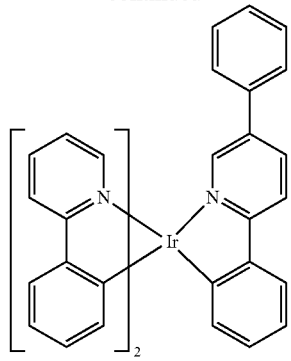
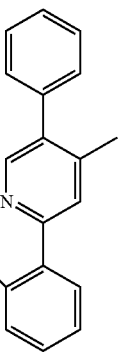
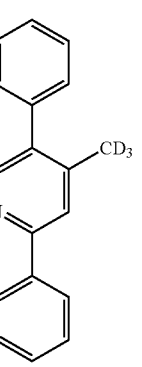
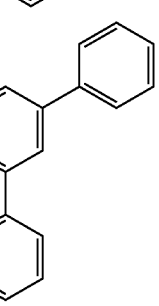
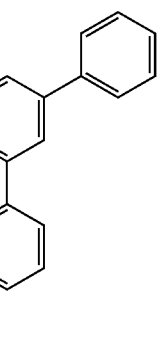

157
-continued
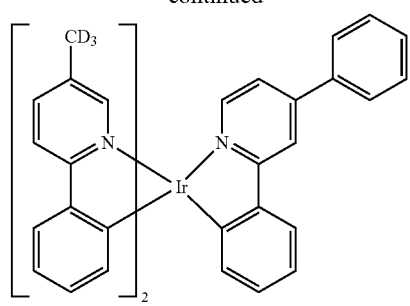
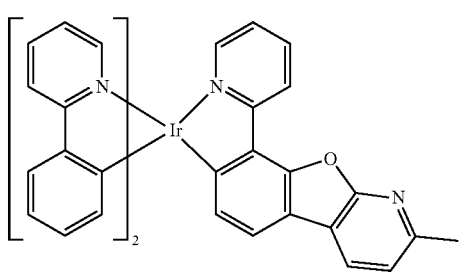
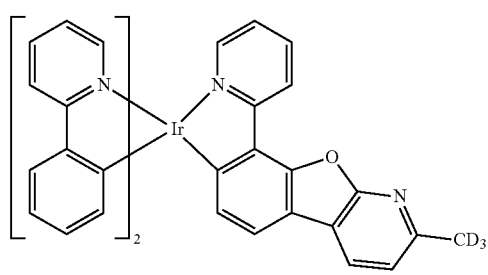
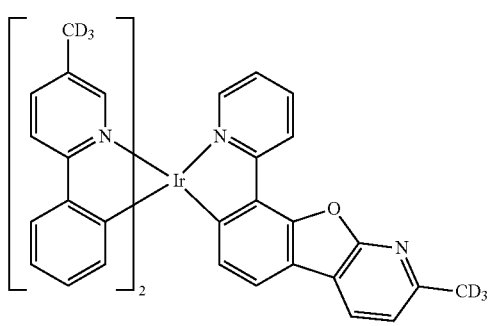
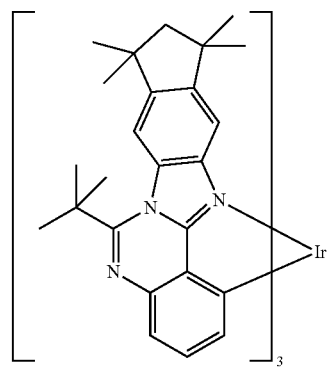
158
-continued
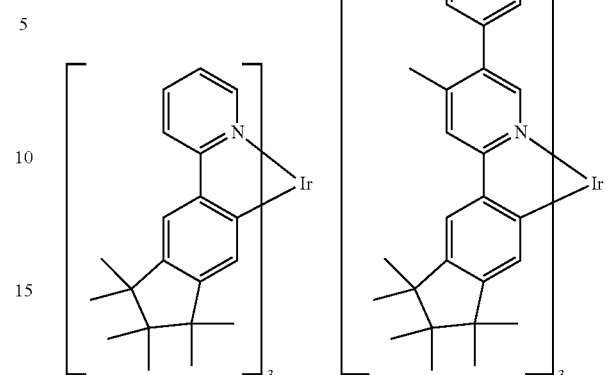
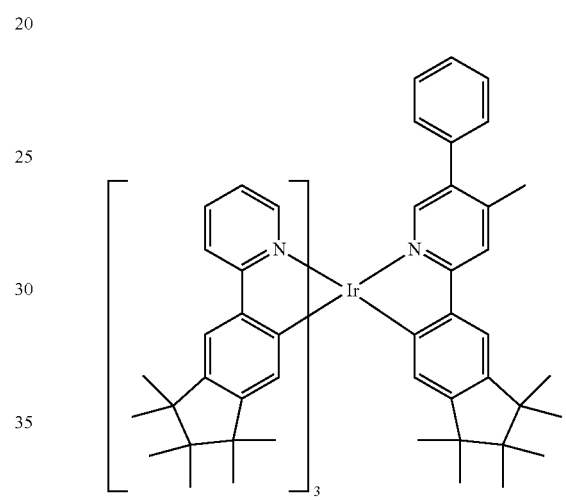
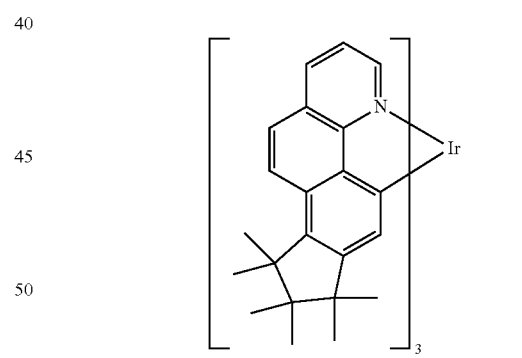
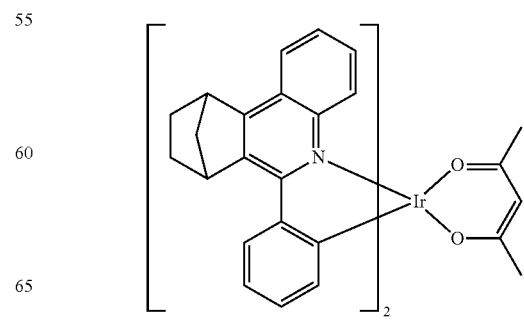

159
-continued
160
-continued
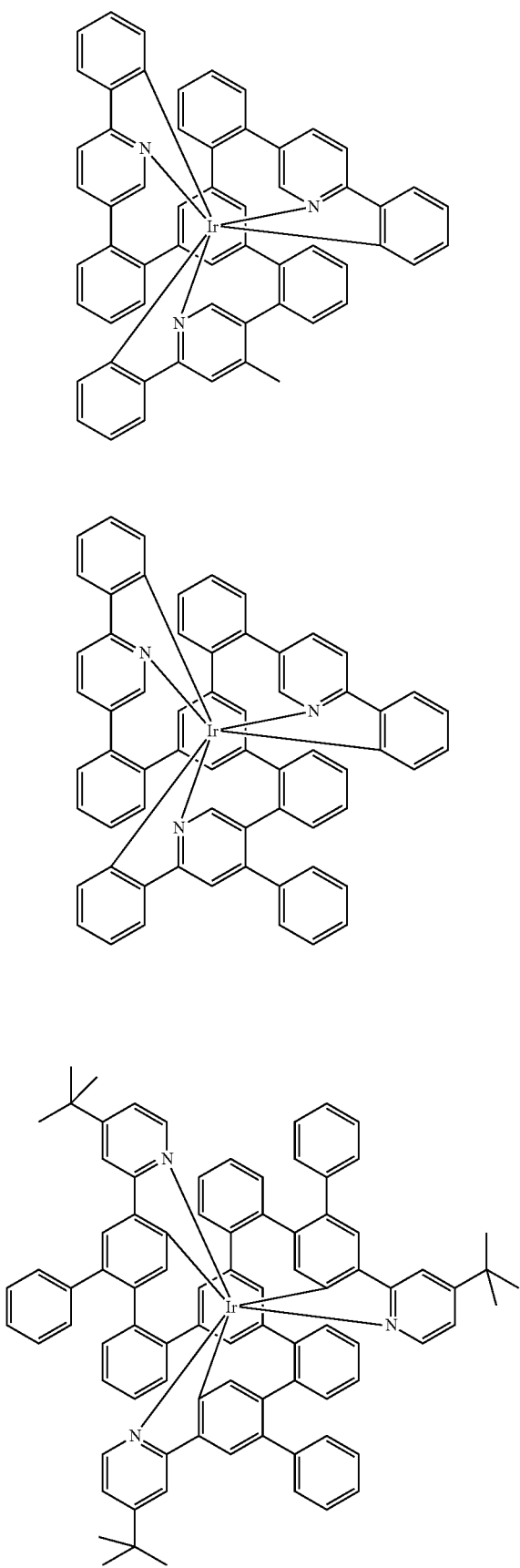
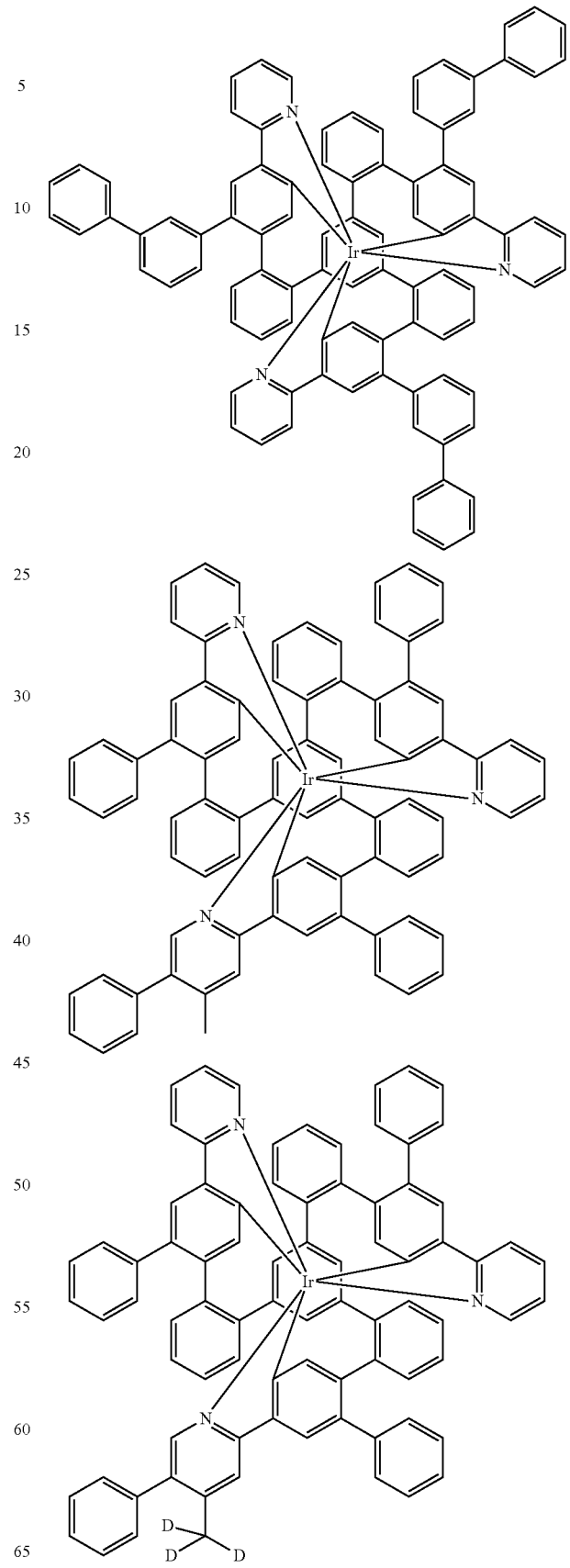

The compounds of the invention are especially also suitable as matrix materials for phosphorescent emitters in organic electroluminescent devices, as described, for example, in WO 98/24271, US 2011/0248247 and US 2012/0223633. In these multicolor display components, an additional blue emission layer is applied by vapor deposition over the full area to all pixels, including those having a color other than blue. It has been found that, surprisingly, the compounds of the invention, when they are used as matrix materials for the red and/or green pixels, still lead to very good emission together with the blue emission layer applied by vapor deposition.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. However, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured.

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapor deposition.

These methods are known in general terms to those skilled in the art and can be applied by those skilled in the art without exercising inventive skill to organic electroluminescent devices comprising the compounds of the invention.

The compounds of the invention and the organic electroluminescent devices of the invention are notable for one or more of the following surprising advantages over the prior art:

1. The compounds of the invention, used as matrix material for phosphorescent emitters, lead to long lifetimes.
2. The compounds of the invention lead to high efficiencies. This is especially true when the compounds are used as matrix material for a phosphorescent emitter.
3. The compounds of the invention lead to low operating voltages. This is especially true when the compounds are used as matrix material for a phosphorescent emitter.

These abovementioned advantages are not accompanied by a deterioration in the further electronic properties.

The invention is illustrated in more detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

Synthesis Examples

The syntheses which follow, unless stated otherwise, are conducted in dried solvents under a protective gas atmosphere. The solvents and reagents can be purchased from ALDRICH or ABCR. The numbers given for the reactants that are not commercially available are the corresponding CAS numbers.

a) 1-(4,6-Diphenyl-[1,3,5]triazin-2-yl)-1H-indole

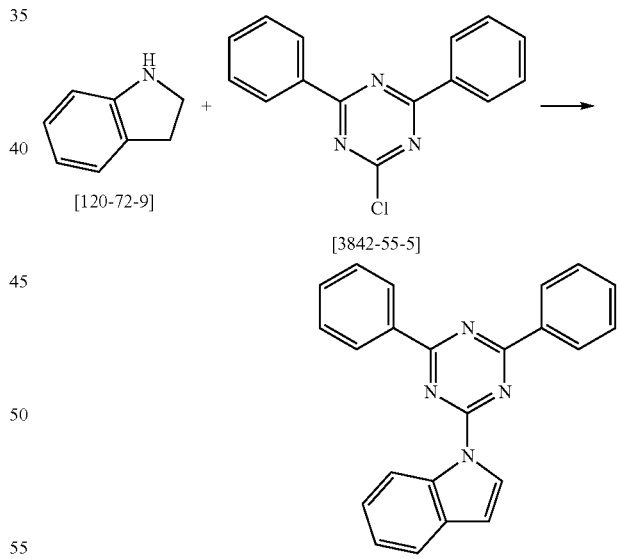

6.4 g (56 mmol) of indole is dissolved in 400 ml of dimethylformamide under a protective gas atmosphere, and 3 g (75 mmol) of NaH, 60% in mineral oil, is added. After 1 h at room temperature, a solution of 2-chloro-4,6-diphenyl-[1,3,5]triazine (17 g, 63.4 mmol, in 150 ml of dimethylformamide) is added dropwise. The reaction mixture is stirred at room temperature for 12 h, then poured onto ice and extracted three times with dichloromethane. The combined organic phases are dried over $Na_2SO_4$ and concentrated. The residue is subjected to hot extraction with toluene. Yield: 15 g (43 mmol), 80% of theory.

The following compounds are prepared in an analogous manner:
| | Reactant 1 | Reactant 2 | Product | Yield |
|---|---|---|---|---|
| 1a | 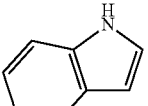 [120-79-9] | 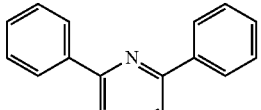 [133785-60-1] | 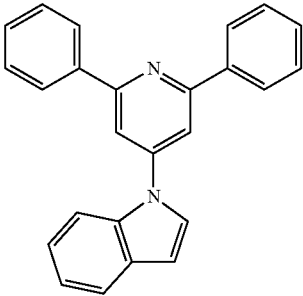 [SMILES: c1ccc(-c2cc(-n3ccc4ccccc43)cc(-c3ccccc3)n2)cc1] | 72% |
| 2a | 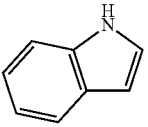 [120-79-9] | 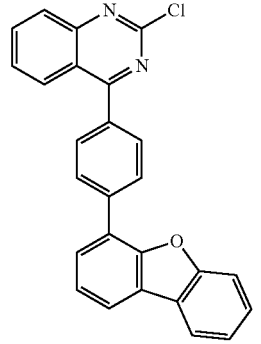 [1403252-58-3] | 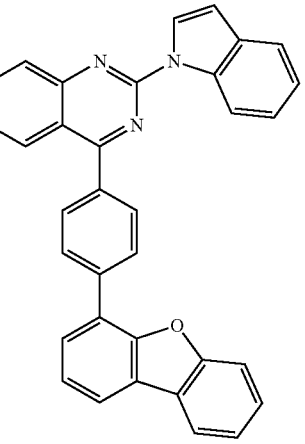 | 75% |
| 3a | 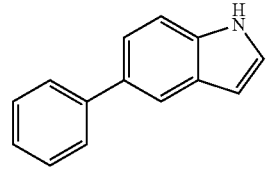 [66616-72-6] | 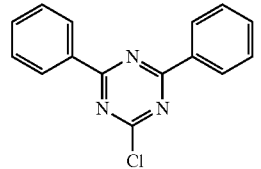 [3842-55-5] | 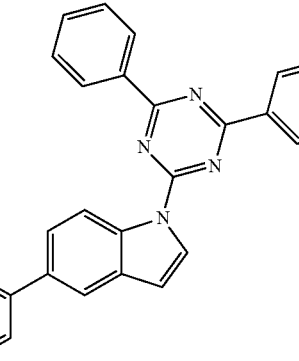 | 68% |
| 4a | 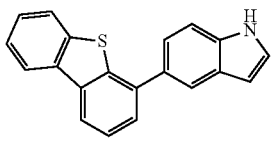 [2093333-09-4] | 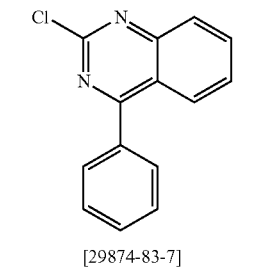 [29874-83-7] | 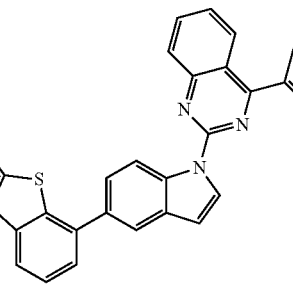 | 69% |

-continued
| | Reactant 1 | Reactant 2 | Product | Yield |
|---|---|---|---|---|
| 5a | 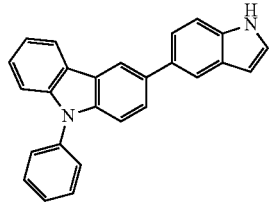<br>[1808216-12-7] | 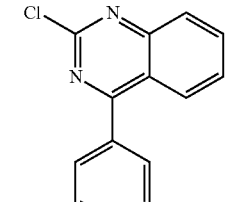<br>[29874-83-7] | 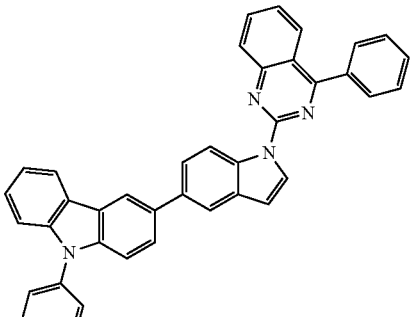 | 62% |
| 6a | 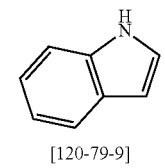<br>[120-79-9] | 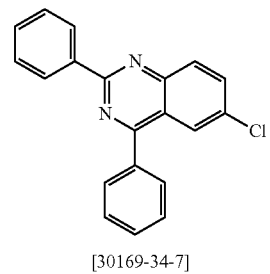 [SMILES: Clc1ccc2nc(-c3ccccc3)nc(-c3ccccc3)c2c1]<br>[30169-34-7] | 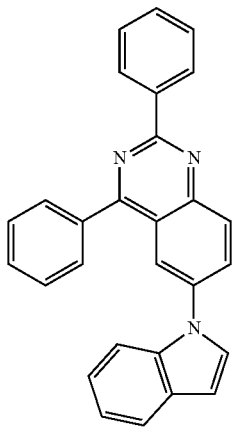 [SMILES: c1ccc(-c2nc(-c3ccccc3)c3cc(-n4ccc5ccccc54)ccc3n2)cc1] | 67% |
| 7a | 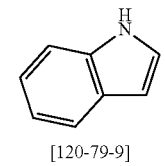<br>[120-79-9] | 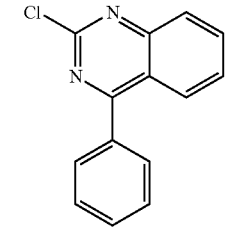<br>[29874-83-7] | 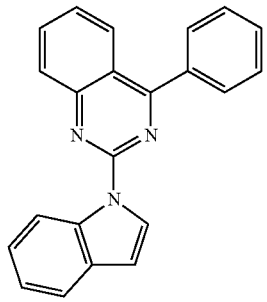 [SMILES: c1ccc(-c2nc(-n3ccc4ccccc43)nc3ccccc23)cc1] | 71% |
| 8a | 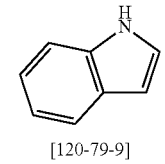<br>[120-79-9] | 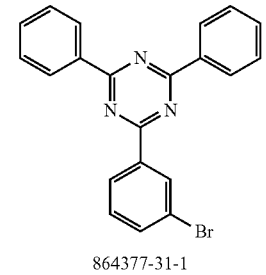 [SMILES: Brc1cccc(-c2nc(-c3ccccc3)nc(-c3ccccc3)n2)c1]<br>864377-31-1 | 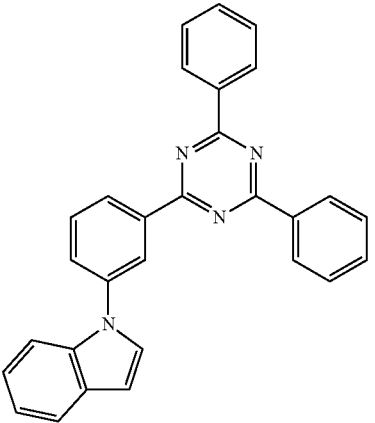 [SMILES: c1ccc(-c2nc(-c3ccccc3)nc(-c3cccc(-n4ccc5ccccc54)c3)n2)cc1] | 70% |

-continued
| Reactant 1 | Reactant 2 | Product | Yield |
|---|---|---|---|
| 9a [1808216-12-7] | | | 76% |
| 10a [120-79-9] | [274258-60-5] | | 65% |
b) 2,3-Dichloro-1-(4,6-diphenyl-[1,3,5]triazin-2-yl)-1H-indole
-continued
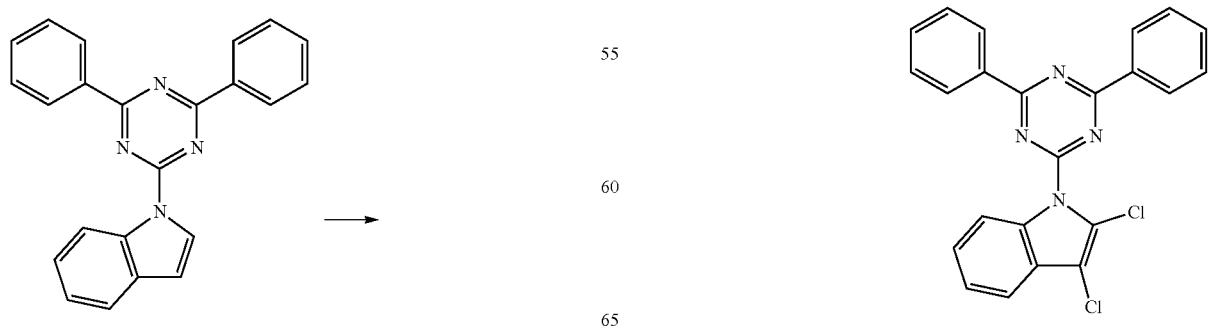

59 g (170.7 mmol) of 1-(4,6-diphenyl-[1,3,5]triazin-2-yl)-1H-indole is dissolved in 500 ml of diethyl ether and cooled to 0° C., 24 g (341 mmol) of thionyl chloride is added dropwise to the synthesis and the mixture is stirred at room temperature overnight. Subsequently, 1 l of sodium hydrogencarbonate solution is added gradually to the mixture, which is transferred to a separating funnel, and the organic phases are separated. The organic phase is washed with brine, dried over sodium sulfate, filtered and concentrated. The product is purified via column chromatography on silica gel with toluene/heptane (2:2). Yield: 40 g (93 mmol), 73% of theory.

The following compounds are prepared in an analogous manner:

| | Reactant | Product | Yield |
|---|---|---|---|
| 1b | | | 52% |
| 2b | | | 45% |
| 3b | | | 47% |

| Reactant | Product | Yield |
|---|---|---|
| 4b | | 39% |
| 5b | | 41% |
| 6b | | 37% |
| 7b | | 51% |

-continued
| | Reactant | Product | Yield |
|---|---|---|---|
| 8b | 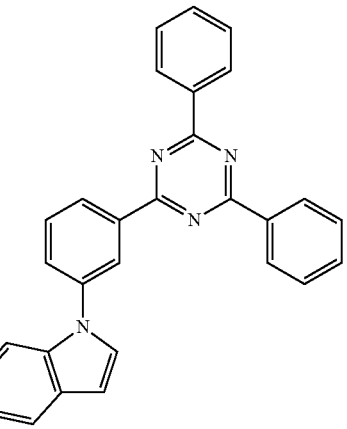 | 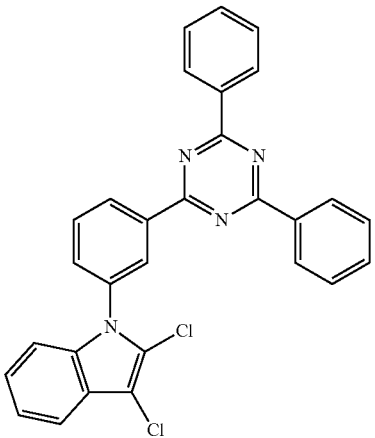 [SMILES: Clc1c(Cl)n(-c2cccc(-c3nc(-c4ccccc4)nc(-c4ccccc4)n3)c2)c2ccccc12] | 70% |
| 9b | 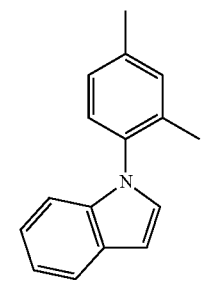
2095543-87-4 | 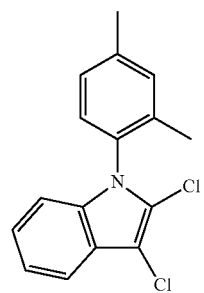 [SMILES: Cc1ccc(-n2c(Cl)c(Cl)c3ccccc32)c(C)c1] | 44% |
| 10b | 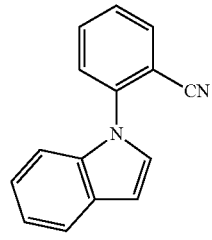
[25699-90-5] | 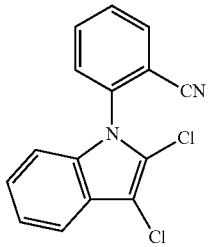 [SMILES: N#Cc1ccccc1-n1c(Cl)c(Cl)c2ccccc21] | 54% |
| 11b | 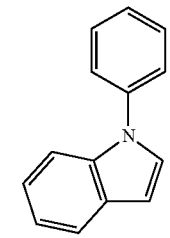
[16096-33-6] | 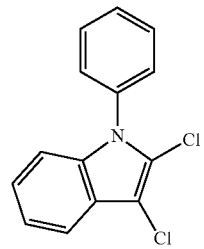 [SMILES: Clc1c(Cl)n(-c2ccccc2)c2ccccc12] | 61% |

-continued

| Reactant | Product | Yield |
|---|---|---|
| 12b 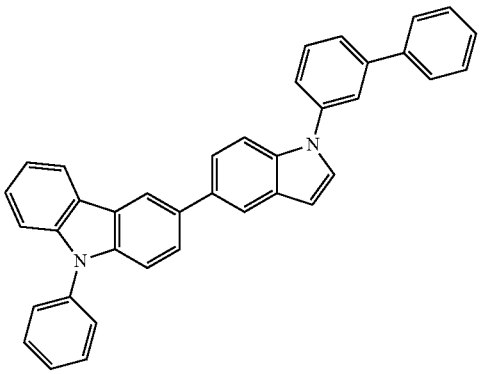 [SMILES: c1ccc(-c2cccc(-n3ccc4cc(-c5ccc6c(c5)c5ccccc5n6-c5ccccc5)ccc43)c2)cc1] | 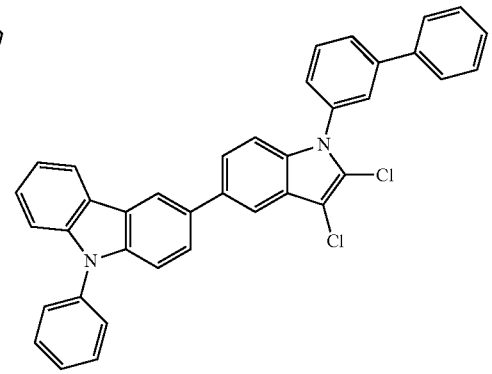 | 58% |
| 13b 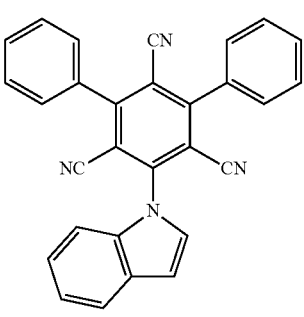 [SMILES: N#Cc1c(-c2ccccc2)c(C#N)c(-n2ccc3ccccc32)c(C#N)c1-c1ccccc1] | 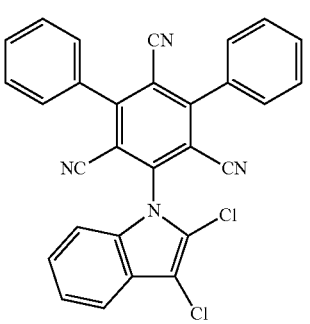 [SMILES: N#Cc1c(-c2ccccc2)c(C#N)c(-n2c(Cl)c(Cl)c3ccccc32)c(C#N)c1-c1ccccc1] | 54% | c) Cyclization

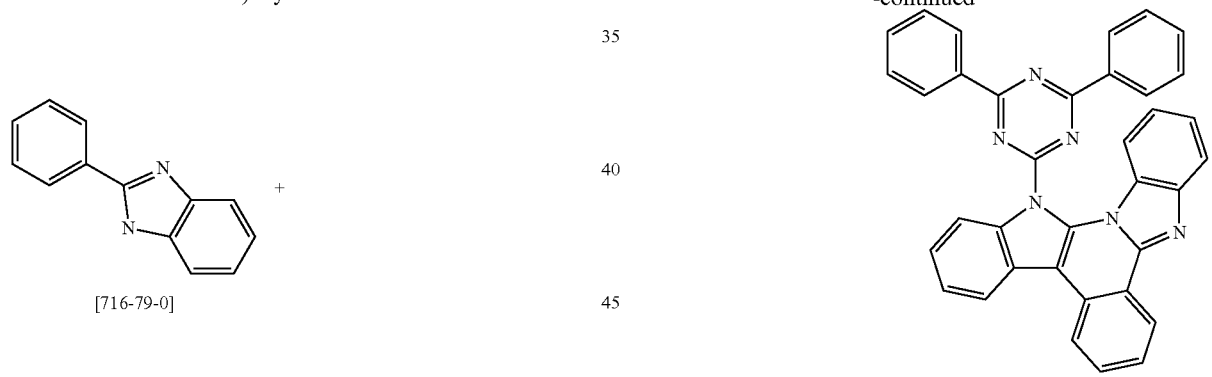

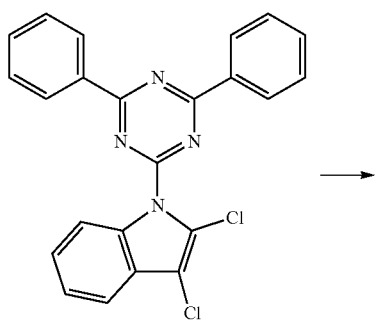

A baked-out Schlenk flask under protective gas is charged with 2.8 g (2.5 mmol, 10 mol %) of Pd(PPh$_3$)$_4$, 1.46 g (2.5 mmol, 10 mol %) of Xantphos, 24.3 g (75 mmol) of 052003 and 5.82 g (30 mmol, 1.2 equiv.) of 2-phenyl-1H-benzimidazole. Subsequently, 10.8 g (25 mmol) of 2,3-dichloro-1-(4,6-diphenyl-[1,3,5]triazin-2-yl)-1H-indole in 200 ml of DMF is added. The mixture is stirred at room temperature for 10 min and then heated under reflux at 140° C. for 24 h. After cooling, 10 ml of dichloromethane is added and the mixture is filtered through Celite. This is followed by concentration to dryness. The product is purified via column chromatography on silica gel with toluene/heptane (2:2). The residue is subjected to hot extraction with toluene, recrystallized from toluene/n-heptane, and finally sublimed under high vacuum. The purity is 99.9%. Yield: 9 g (15.2 mmol), 70% of theory.

The following compounds are prepared in an analogous manner:

| | Reactant 1 | Reactant 2 | Product | Yield |
|---|---|---|---|---|
| 1c | [716-79-0] | 1802980-63-7 | | 64% |
| 2c | [948-65-2] | | | 63% |
| 3c | [716-79-0] | | | 64% |
| 4c | [716-79-0] | | | 62% |

-continued
| | Reactant 1 | Reactant 2 | Product | Yield |
|---|---|---|---|---|
| 5c | 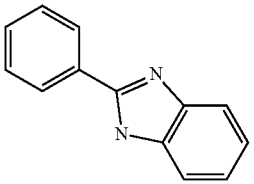 [716-79-0] | 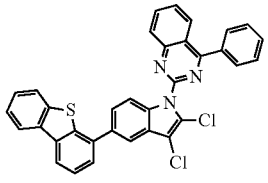 [SMILES: Clc1c(Cl)n(-c2nc(-c3ccccc3)c3ccccc3n2)c2ccc(-c3cccc4c3sc3ccccc34)cc12] | 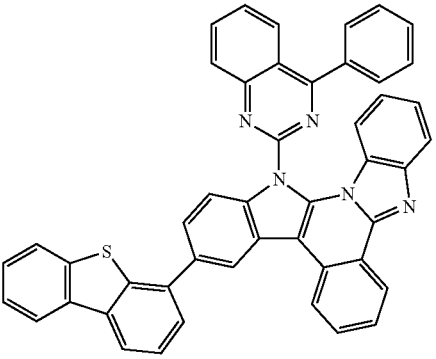 [SMILES: c1ccc(-c2nc(-n3c4ccc(-c5cccc6c5sc5ccccc56)cc4c4c5ccccc5c5nc6ccccc6n5c43)nc3ccccc23)cc1] | 64% |
| 6c | 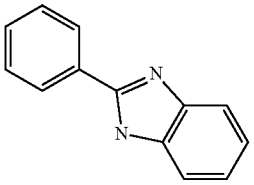 [716-79-0] | 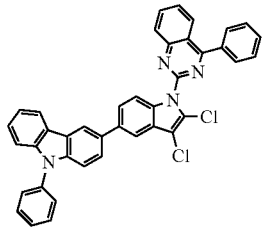 [SMILES: Clc1c(Cl)n(-c2nc(-c3ccccc3)c3ccccc3n2)c2ccc(-c3ccc4c(c3)c3ccccc3n4-c3ccccc3)cc12] | 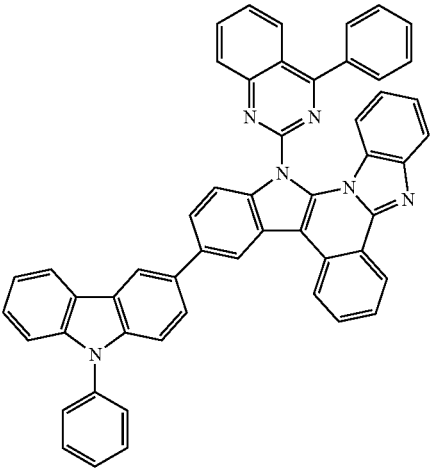 | 69% |
| 7c | 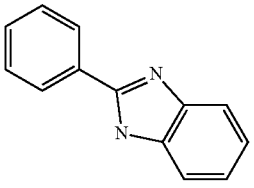 [716-79-0] | 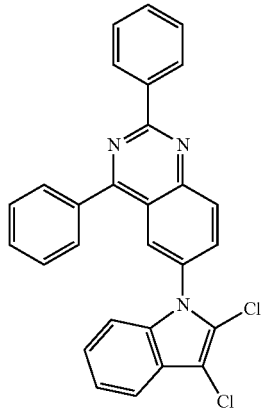 [SMILES: Clc1c(Cl)n(-c2ccc3nc(-c4ccccc4)nc(-c4ccccc4)c3c2)c2ccccc12] | 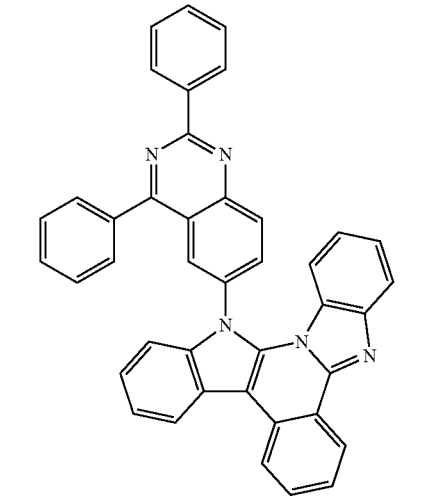 [SMILES: c1ccc(-c2nc(-c3ccccc3)c3cc(-n4c5ccccc5c5c6ccccc6c6nc7ccccc7n6c54)ccc3n2)cc1] | 66% |

| | Reactant 1 | Reactant 2 | Product | Yield |
|---|---|---|---|---|
| 8c | [716-79-0] | | | 60% |
| 9c | [716-79-0] | | | 71% |
| 10c | [716-79-0] | | | 70% |
| 11c | [716-79-0] | | | 71% |

-continued
| | Reactant 1 | Reactant 2 | Product | Yield |
|---|---|---|---|---|
| 12c | 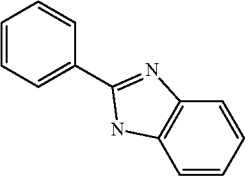 [716-79-0] | 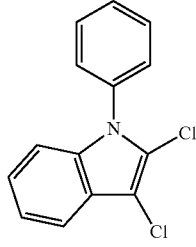 [SMILES: Clc1c(Cl)n(-c2ccccc2)c2ccccc12] | 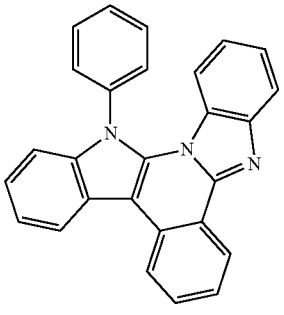 [SMILES: c1ccc(-n2c3ccccc3c3c4ccccc4c4nc5ccccc5n4c32)cc1] | 79% |
| 13c | 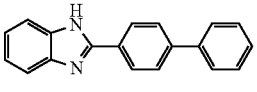 [2562-77-8] | 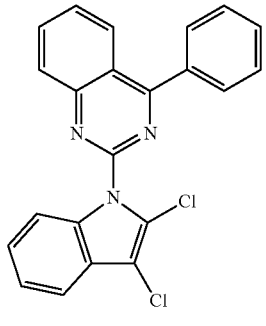 [SMILES: Clc1c(Cl)n(-c2nc(-c3ccccc3)c3ccccc3n2)c2ccccc12] | 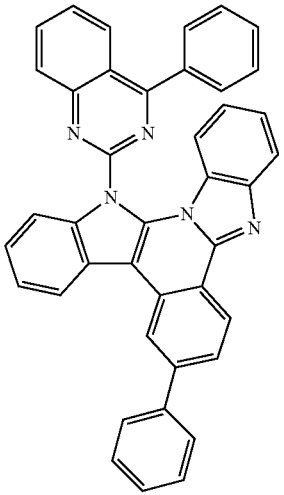 [SMILES: c1ccc(-c2ccc3c(c2)c2c4ccccc4n(-c4nc(-c5ccccc5)c5ccccc5n4)c2n2c4ccccc4nc32)cc1] | 73% |
| 14c | 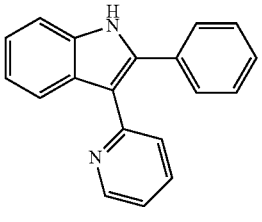 [91025-04-6] | 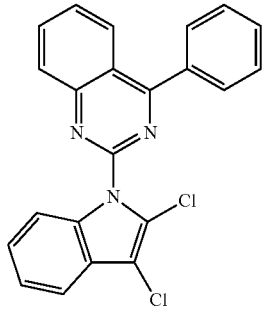 [SMILES: Clc1c(Cl)n(-c2nc(-c3ccccc3)c3ccccc3n2)c2ccccc12] | 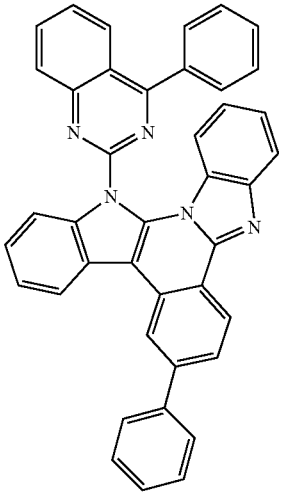 [SMILES: c1ccc(-c2ccc3c(c2)c2c4ccccc4n(-c4nc(-c5ccccc5)c5ccccc5n4)c2n2c4ccccc4nc32)cc1] | 77% |

-continued
| | Reactant 1 | Reactant 2 | Product | Yield |
|---|---|---|---|---|
| 15c | 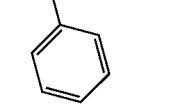 [3469-20-3] | 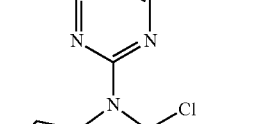 | 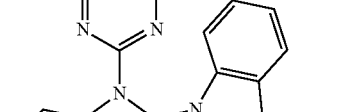 | 79% |
| 16c | 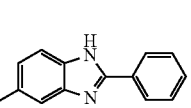 [6528-80-9] | 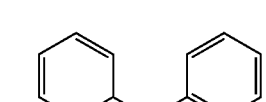 | 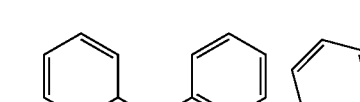 | 73% |
| 17c |  [581783-20-2] | 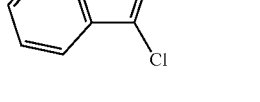 | 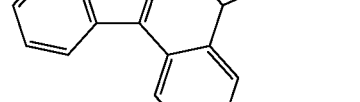 | 68% |
| 18c | 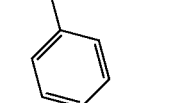 [1346627-55-1] | 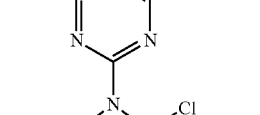 | 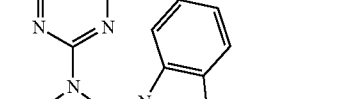 | 71% |

-continued

| Reactant 1 | Reactant 2 | Product | Yield |
|---|---|---|---|
| 19c [948-65-2] | | | 70% |
| 20c [1803168-60-6] | | | 57% |
| 21c [948-65-2] | | | 57% |

-continued
| | Reactant 1 | Reactant 2 | Product | Yield |
|---|---|---|---|---|
| 22c | 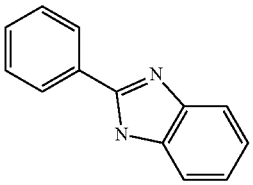 [716-79-0] | 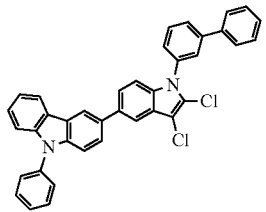 [SMILES: Clc1c(Cl)n(-c2cccc(-c3ccccc3)c2)c2ccc(-c3ccc4c(c3)c3ccccc3n4-c3ccccc3)cc12] | 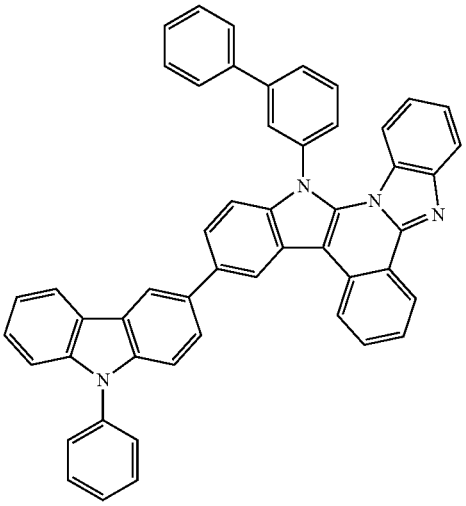 [SMILES: c1ccc(-c2cccc(-n3c4ccc(-c5ccc6c(c5)c5ccccc5n6-c5ccccc5)cc4c4c5ccccc5c5nc6ccccc6n5c43)c2)cc1] | 53% |
| 23c | 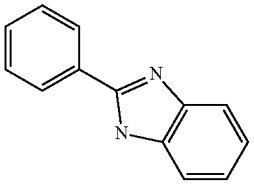 [716-79-0] | 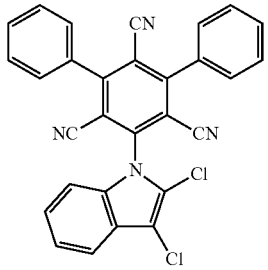 [SMILES: N#Cc1c(-c2ccccc2)c(C#N)c(-n2c(Cl)c(Cl)c3ccccc32)c(C#N)c1-c1ccccc1] | 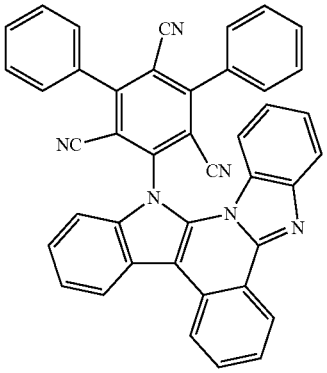 [SMILES: N#Cc1c(-c2ccccc2)c(C#N)c(-n2c3ccccc3c3c4ccccc4c4nc5ccccc5n4c32)c(C#N)c1-c1ccccc1] | 55% |
| 24c | 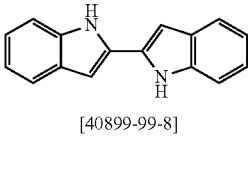 [SMILES: c1ccc2[nH]c(-c3cc4ccccc4[nH]3)cc2c1] [40899-99-8] | 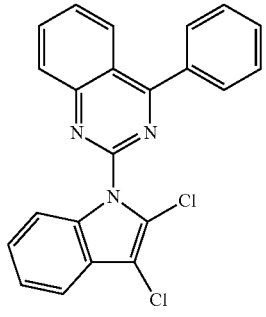 [SMILES: Clc1c(Cl)n(-c2nc(-c3ccccc3)c3ccccc3n2)c2ccccc12] | 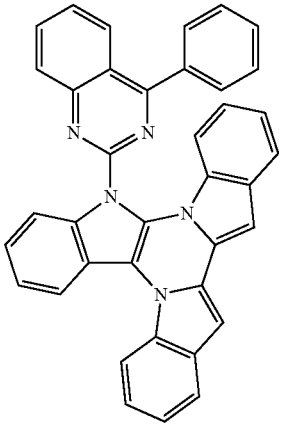 [SMILES: c1ccc(-c2nc(-n3c4ccccc4c4c3n3c5ccccc5cc3c3cc5ccccc5n34)nc3ccccc23)cc1] | 52% |

-continued
| | Reactant 1 | Reactant 2 | Product | Yield |
|---|---|---|---|---|
| 25c | 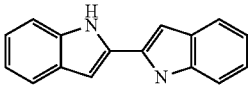<br>[40899-99-8] | 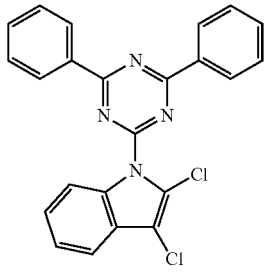 [SMILES: Clc1c(Cl)n(-c2nc(-c3ccccc3)nc(-c3ccccc3)n2)c2ccccc12] | 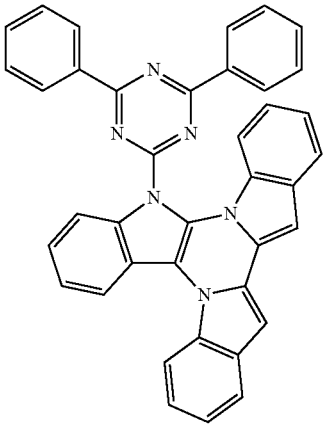 [SMILES: c1ccc(-c2nc(-c3ccccc3)nc(-n3c4ccccc4c4c3n3c5ccccc5cc3c3cc5ccccc5n34)n2)cc1] | 55% |
| 26c | 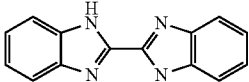<br>[6965-02-2] | 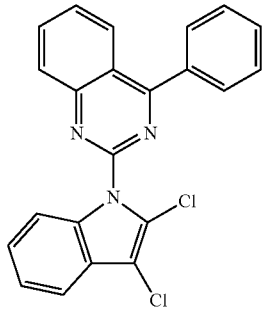 [SMILES: Clc1c(Cl)n(-c2nc(-c3ccccc3)c3ccccc3n2)c2ccccc12] | 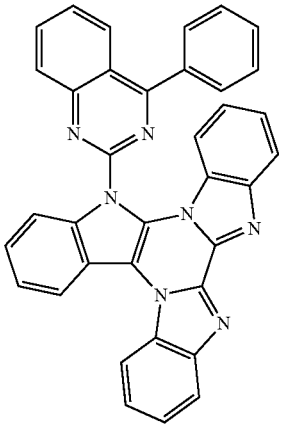 [SMILES: c1ccc(-c2nc(-n3c4ccccc4c4c3n3c5ccccc5nc3c3nc5ccccc5n34)nc3ccccc23)cc1] | 61% |

-continued

| Reactant 1 | Reactant 2 | Product | Yield |
|---|---|---|---|
| 27c [6965-02-2] | | | 56% |
| 28c [6965-02-2] | | | 59% | d) 11-(2,6-Diphenylpyrimidin-4-yl)-6H,11H-indolo[3,2-c]isoquinolin-5-one

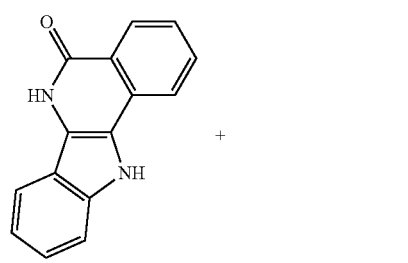

[153141-59-3]

+

[40734-24-5]

→

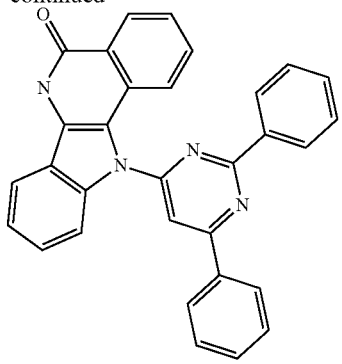

Under protective gas, 20.5 g (88 mmol) of 6H-11H-indolo[3,2-c]isoquinolin-5-one, 27.3 g (88 mmol) of 4-bromo-2,6-diphenylpyrimidine, 0.8 g (0.88 mmol) of tris(dibenzylideneacetone)dipalladium and 1.79 g (7.9 mmol) of palladium acetate are suspended in 500 ml of toluene. The reaction mixture is heated under reflux for 8 h. After cooling, the organic phase is removed, washed three times with 200 ml of water and then concentrated to dryness. The product is purified via column chromatography on silica gel with toluene/heptane (2:2). The purity is 97.0%. Yield: 30 g (64 mmol), 70% of theory.

The following compound is prepared in an analogous manner:

| Reactant 1 | Reactant 2 | Product | Yield |
|---|---|---|---|
| 1d [153141-58-3] | [29874-83-7] | | 54% | e) 5-Chloro-11-(2,6-diphenylpyrimidin-4-yl)-11H-indolo[3,2-c]-isoquinoline

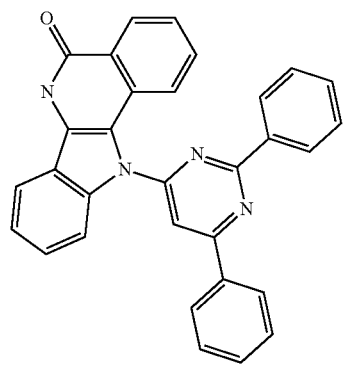

8.8 g (19 mmol) of 11-(2,6-diphenylpyrimidin-4-yl)-6H,11H-indolo[3,2-c]-isoquinolin-5-one is additionally charged in 6 g (29 mmol) of $POCl_3$ and 50 ml of $PCl_5$. The mixture is boiled under reflux for 4 h, cooled down, and 100 ml of toluene is added. Saturated NaCl is added to the mixture, and the organic phase is removed. The solvent and the $PCl_5$ are removed under reduced pressure, and the product is recrystallized from toluene under protective gas. Yield: 8.2 g (16 mmol), 90% of theory.

-continued

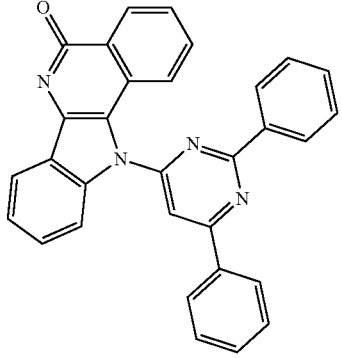

The following compound is prepared in an analogous manner:

| Reactant | Product | Yield |
|---|---|---|
| 1e | | 44% |

197 f) (2-Bromophenyl)-[11-(2,6-diphenylpyrimidin-4-yl)-11H-indolo-[3,2-c]isoquinolin-5-yl]amine

198 g) Cyclization

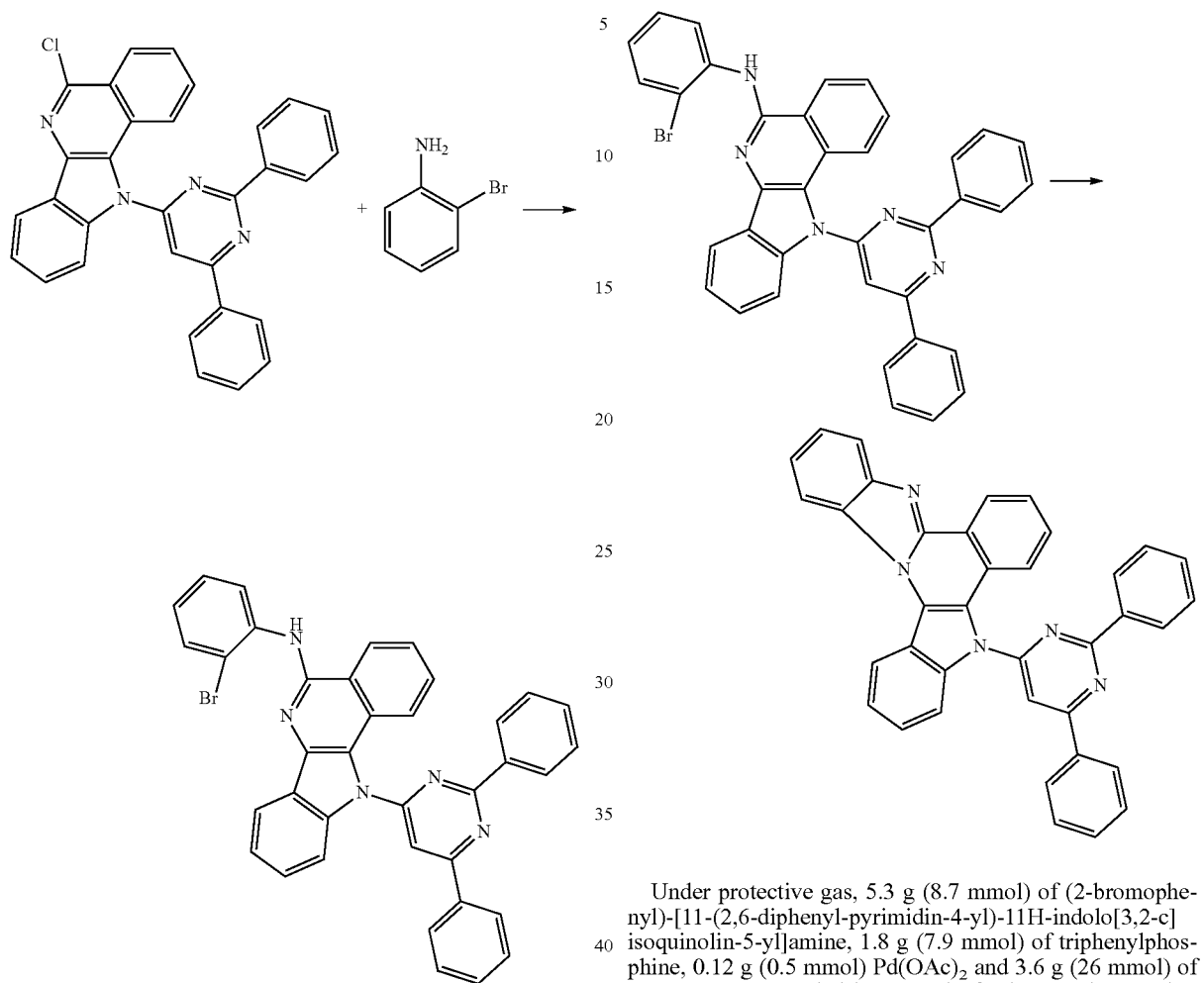

38.8 g (7.9 mmol) of 5-chloro-11-(2,6-diphenylpyrimidin-4-yl)-11H-indolo-[3,2-c]isoquinoline and 7.3 g (15.8 mmol) of 2-bromophenylamine are heated under reflux in 100 ml of diglyme at 160° C. for 3 h. After cooling, the residue is filtered. Yield: 8.2 g (16 mmol), 90% of theory.

The following compound is prepared in an analogous manner:

Under protective gas, 5.3 g (8.7 mmol) of (2-bromophenyl)-[11-(2,6-diphenyl-pyrimidin-4-yl)-11H-indolo[3,2-c]isoquinolin-5-yl]amine, 1.8 g (7.9 mmol) of triphenylphosphine, 0.12 g (0.5 mmol) Pd(OAc)$_2$ and 3.6 g (26 mmol) of NaCO$_3$ are suspended in 100 ml of toluene. The reaction mixture is heated under reflux for 8 h. After cooling, the organic phase is removed, washed three times with 200 ml of water and then concentrated to dryness. The product is purified via column chromatography on silica gel with toluene/heptane (2:2) and then sublimed under high vacuum. The purity is 99.9%. Yield: 3.7 g (6.9 mmol), 80% of theory.

The following compound is prepared in an analogous manner:

| | Reactant 1 | Reactant 2 | Product | Yield |
|---|---|---|---|---|
| 1f | | | | 68% |

| Reactant | Product | Yield |
|---|---|---|
| 1g | | 67% |

Production of the OLEDs

Examples I1 to I6 which follow (see Table 1) present the use of the materials of the invention in OLEDs.

Pretreatment for Examples I1-I6:

Glass plaques coated with structured ITO (indium tin oxide) of thickness 50 nm are treated prior to coating with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/ optional hole blocker layer (HBL)/electron transport layer (ETL)/optional electron injection layer (EIL) and finally a cathode. The cathode is formed by an aluminum layer of thickness 100 nm. The exact structure of the OLEDs can be found in Table 1. The materials required for production of the OLEDs are shown in Table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:EG1:TER (50%:45%:5%) mean here that the material IC1 is present in the layer in a proportion by volume of 50%, EG1 in a proportion by volume of 45% and TER in a proportion by volume of 5%. Analogously, the electron transport layer may also consist of a mixture of two materials.

The OLEDs are characterized in a standard manner. The electroluminescence spectra are determined at a luminance of 1000 cd/m$^2$, and the CIE 1931 x and y color coordinates are calculated therefrom.

Use of Mixtures of the Invention in OLEDs

The materials of the invention can be used in the emission layer in phosphorescent red OLEDs. The inventive compounds EG1 to EG5 may be used in Examples 11 to 16 as matrix material in the emission layer. The color coordinates of the electroluminescence spectra of these OLEDs are CIEx=0.67 and CIEy=0.33. The materials are thus suitable for use in the emission layer of red OLEDs. In addition, the materials of the invention can be used successfully in the hole blocker layer (HBL). This is shown in experiment 16. Here too, the color coordinates of the spectrum of the OLED are CIEx=0.67 and CIEy=0.33.

TABLE 1

Structure of the OLEDs

| Ex. | HIL thickness | HTL thickness | EBL thickness | EML thickness | HBL thickness | ETL thickness | EIL thickness |
|---|---|---|---|---|---|---|---|
| I1 | HATCN 5 nm | SpMA1 125 nm | SpMA3 10 nm | IC1:EG1:TER (50%:45%:5%) 40 nm | — | ST2:LiQ (50%:50%) 35 nm | — |
| I2 | HATCN 5 nm | SpMA1 125 nm | SpMA3 10 nm | IC2:EG2:TER (50%:45%:5%) 40nm | — | ST2:LiQ (50%:50%) 35 nm | — |
| I3 | HATCN 5 nm | SpMA1 125 nm | SpMA3 10 nm | IC2:EG3:TER (50%:45%:5%) 40nm | — | ST2:LiQ (50%:50%) 35 nm | — |
| I4 | HATCN 5 nm | SpMA1 125 nm | SpMA3 10 nm | IC2:EG4:TER (50%:45%:5%) 40nm | — | ST2:LiQ (50%:50%) 35 nm | — |
| I5 | HATCN 5 nm | SpMA1 125 nm | SpMA3 10 nm | EG5:TER (95%:5%) 40 nm | — | ST2:LiQ (50%:50%) 35 nm | — |
| I6 | HATCN 5 nm | SpMA1 125 nm | SpMA3 10 nm | EG5:TER (95%:5%) 40 nm | EG2 5 nm | ST2:LiQ (50%:50%) 30 nm | — |

TABLE 2
Structural formulae of the materials for the OLEDs
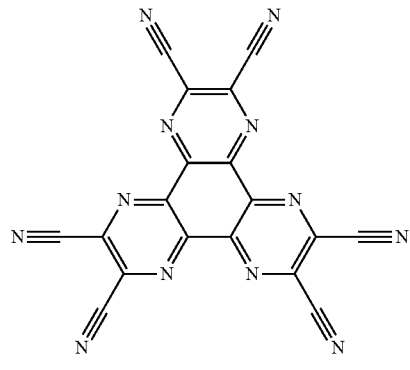
HATCN
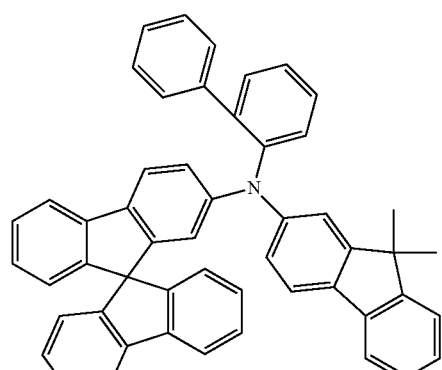
SpMA1
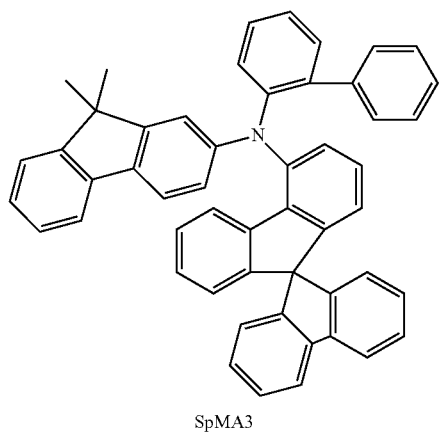 [SMILES: CC1(C)c2ccccc2-c2ccc(N(c3ccccc3-c3ccccc3)c3cccc4c3-c3ccccc3C43c4ccccc4-c4ccccc43)cc21]
SpMA3
TABLE 2-continued
Structural formulae of the materials for the OLEDs
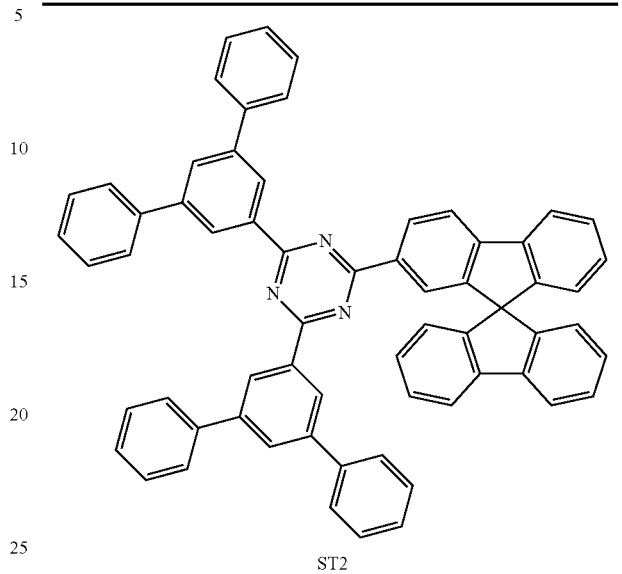
ST2
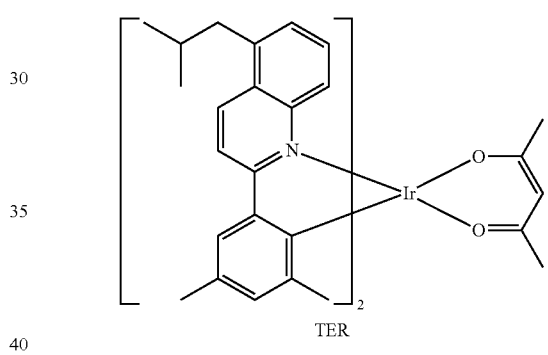
TER
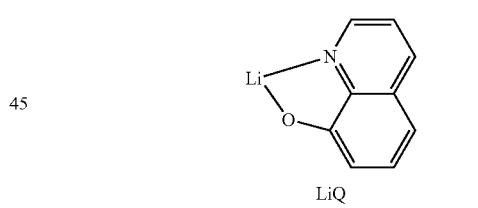
LiQ
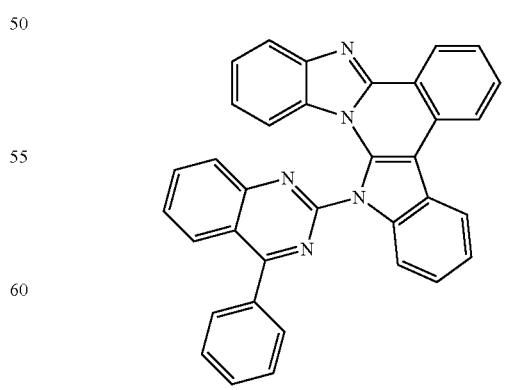
EG1

TABLE 2-continued
Structural formulae of the materials for the OLEDs
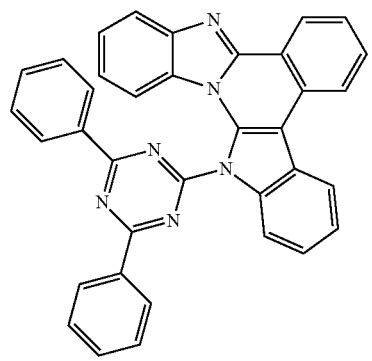
EG2
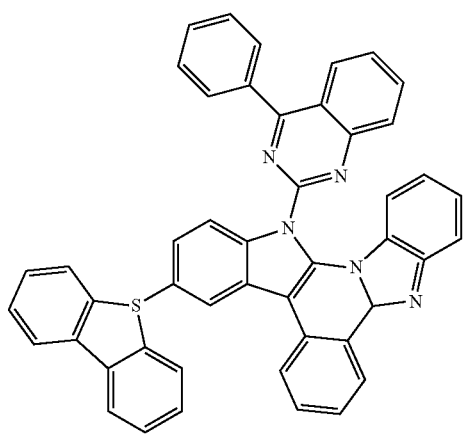
EG3
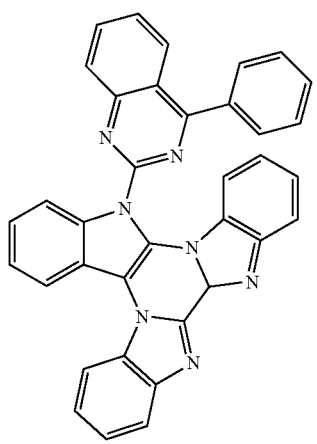
EG4
TABLE 2-continued
Structural formulae of the materials for the OLEDs
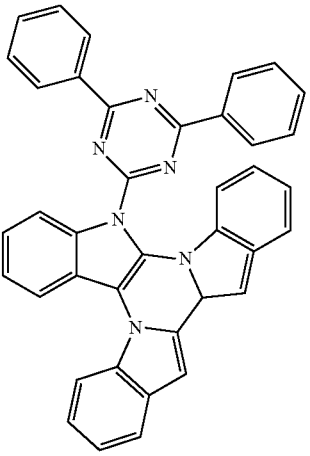
EG5
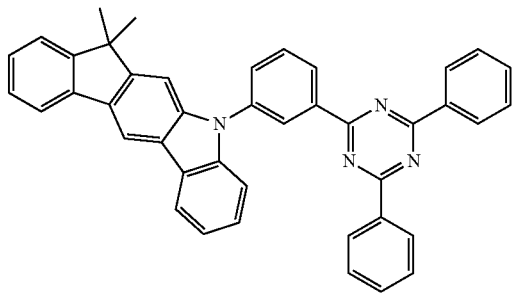
IC1
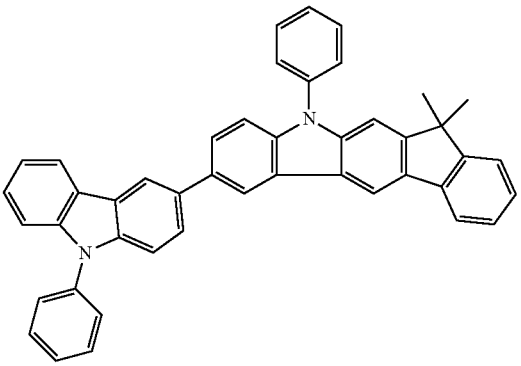
IC2
The invention claimed is:
1. A compound of formula (1)
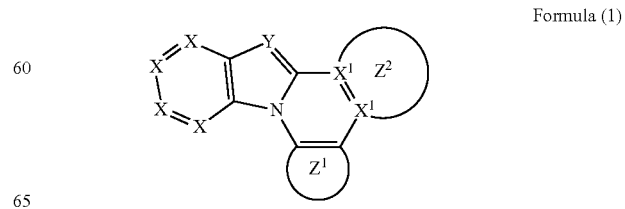
Formula (1)

where the symbols used are as follows:

$Z^1$ is a group of the formula (2)

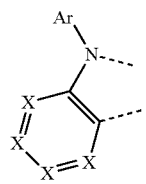

Formula (2)

where the dotted bonds indicate the linkage of this group to the two carbon atoms explicitly shown in formula (1);

$Z^2$ is a group of the formula (4) or (5)

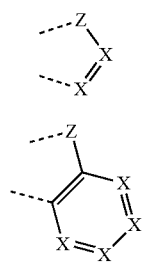

Formula (4)

Formula (5)

where the dotted bonds indicate the linkage of this group to $X^1$ in formula (1);

$X^1$ group is C and the other $X^1$ group is N;
X is the same or different at each instance and is CR or N;
Y is CR or N;
Z is CR or N;
Ar is the same or different at each instance and is an aromatic or heteroaromatic ring system which has 5 to 40 aromatic ring atoms and may be substituted by one or more R radicals;
R is the same or different at each instance and is H, D, F, Cl, Br, I, $N(Ar')_2$, $N(R^1)_2$, $OAr'$, $SAr'$, CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms, and may be substituted in each case by one or more $R^1$ radicals; at the same time, two R radicals together may also form a ring system;
Ar' is the same or different at each instance and is an aromatic or heteroaromatic ring system which has 5 to 40 aromatic ring atoms and may be substituted by one or more $R^1$ radicals;
$R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2 R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^2$ radicals, where one or more nonadjacent $CH_2$ groups may replaced by $Si(R^2)_2$, C=O, $NR^2$, O, S or $CONR^2$ and one or more hydrogen atoms in the alkyl, alkenyl or alkynyl group may be replaced by D, F, Cl, Br, I or CN, or an aromatic or heteroaromatic ring system which has 5 to 40 aromatic ring atoms and may be substituted in each case by one or more $R^2$ radicals; at the same time, two or more $R^1$ radicals together may form a ring system;
$R^2$ is the same or different at each instance and is H, D, F, CN or an aliphatic, aromatic or heteroaromatic organic radical, which has 1 to 20 carbon atoms and in which one or more hydrogen atoms may also be replaced by F.

2. The compound as claimed in claim 1, wherein the group of the formula (2) is a group of the formula (2a)

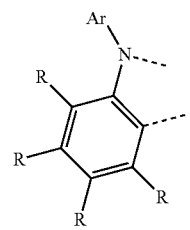

Formula (2a)

where the symbols used have the definitions given in claim 1.

3. The compound as claimed in claim 1, of the formula (6a) or (7a)

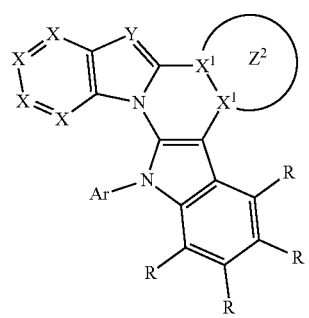

Formula (6a)

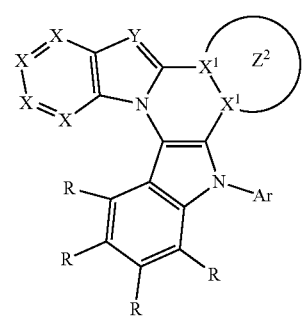

Formula (7a)

where the symbols used have the definitions given in claim 1 and not more than one X in the compound including the structure $Z^2$ is N.

4. The compound as claimed in claim 1, wherein Y=N and that Z=N.

5. The compound as claimed in claim 1, wherein Ar is the same or different at each instance and is selected from phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more R radicals.

6. The compound as claimed in claim 1, wherein R is the same or different at each instance and is selected from the group consisting of H, D, F, N(Ar')$_2$, CN, OR$^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more R$^1$ radicals and where one or more nonadjacent CH$_2$ groups may be replaced by O, or an aromatic or heteroaromatic ring system which has 6 to 30 aromatic ring atoms and may be substituted in each case by one or more R$^1$ radicals; at the same time, two R radicals together may also form a ring system.

7. A formulation comprising at least one compound as claimed in claim 1 and at least one further compound, wherein the further compound is one or more solvents and/or at least one further organic or inorganic compound.

8. An electronic device comprising the formulation as claimed in claim 7.

9. An electronic device comprising the compound as claimed in claim 1.

10. An electronic device comprising at least one compound as claimed in claim 1, wherein the electronic device is selected from the group consisting of organic electroluminescent devices, organic integrated circuits, organic field-effect transistors, organic thin-film transistors, organic light-emitting transistors, organic solar cells, dye-sensitized organic solar cells, organic optical detectors, organic photoreceptors, organic field-quench devices, light-emitting electrochemical cells, organic laser diodes and organic plasmon-emitting devices.

11. An organic electroluminescent device comprising the compound as claimed in claim 1 is used as matrix material in an emitting layer and/or in an electron transport layer and/or in a hole blocker layer and/or in a hole transport layer and/or in an exciton blocker layer.

12. The compound as claimed in claim 1, wherein R$^2$ is the same or different at each instance and is H, D, F, CN or a hydrocarbyl radical, which has 1 to 20 carbon atoms and in which one or more hydrogen atoms may also be replaced by F.

13. The compound as claimed in claim 1, selected from the compounds of the formulae (9) to (14)

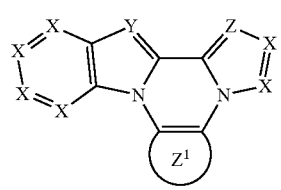

Formula (9)

-continued

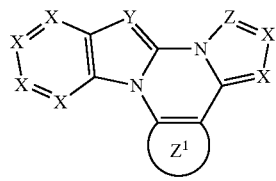

Formula (10)

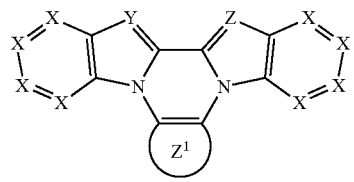

Formula (11)

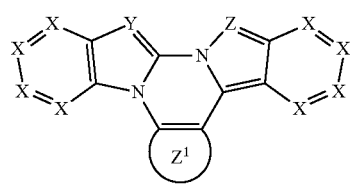

Formula (12)

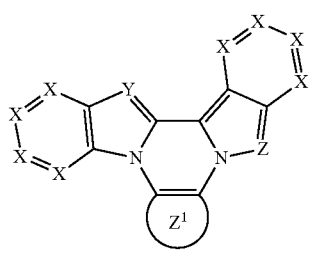

Formula (13)

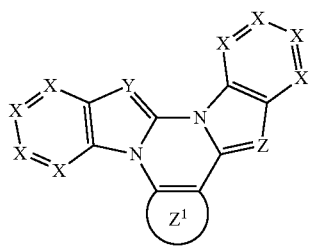

Formula (14)

where the symbols have the same definitions as detailed in claim 1, and Z in the formulae (9) to (12) is CR or N.

14. The compound as claimed in claim 1, of the formulae (9a) to (14b)

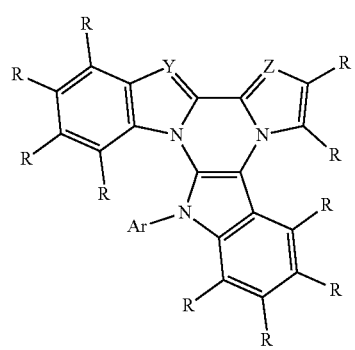

Formula (9a)

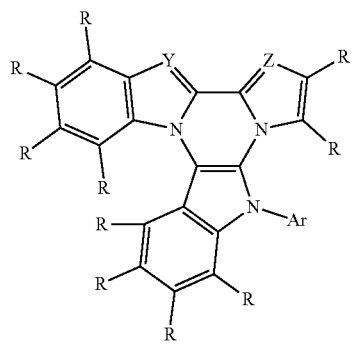
Formula (9b)
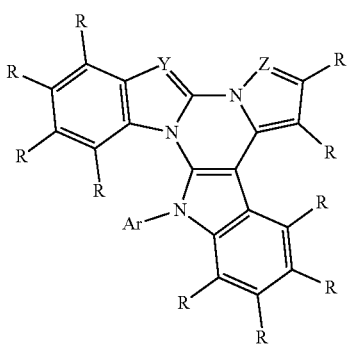
Formula (10a)
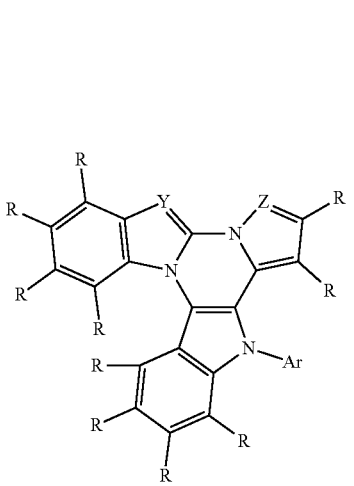
Formula (10b)
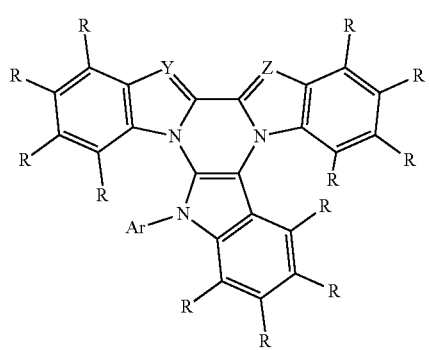
Formula (11a)
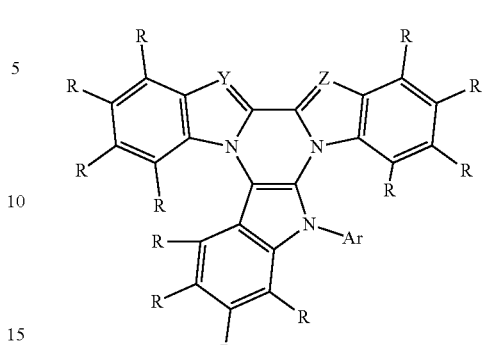
Formula (11b)
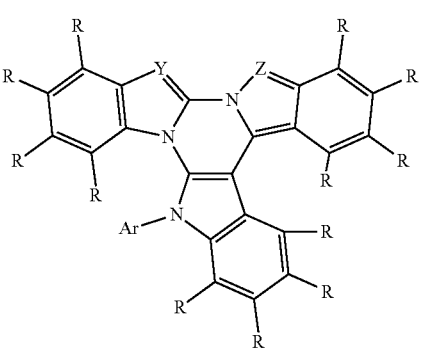
Formula (12a)
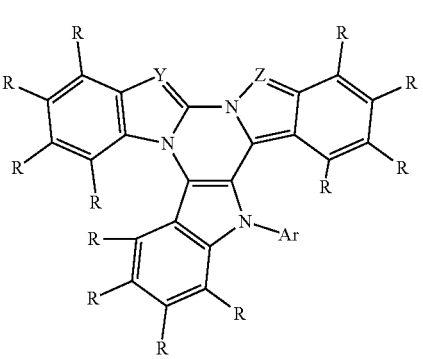
Formula (12b)
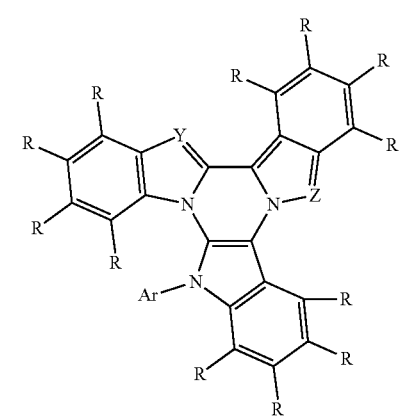
Formula (13a)

Formula (13b)
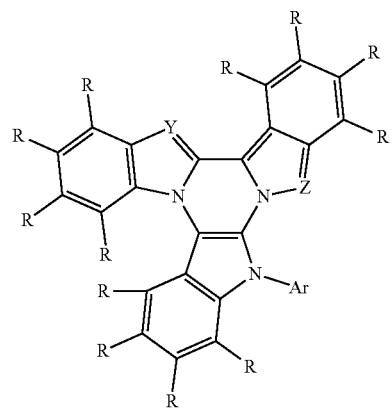
Formula (14a)
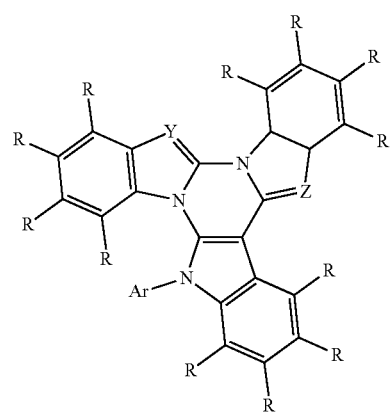
Formula (14b)
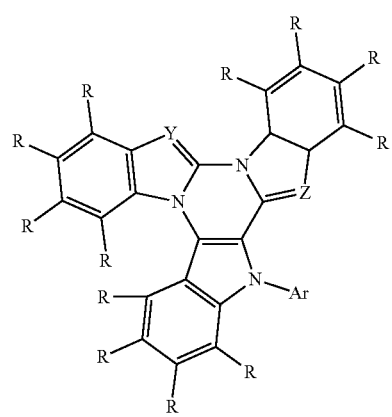
where the symbols used have the definitions given in claim 1 and Z in the formulae (9a) to (14b) is CR or N.
15. The compound as claimed in claim 1, selected from the compounds of the formulae (9a-2) to (14b-2)
Formula (9a-2)
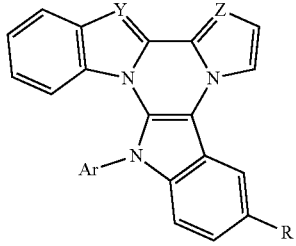
Formula (9b-2)
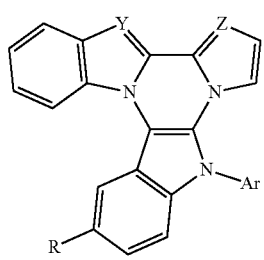
Formula (10a-2)
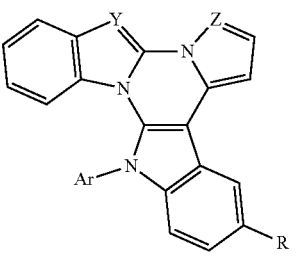
Formula (10b-2)
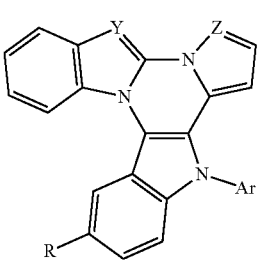
Formula (11a-2)
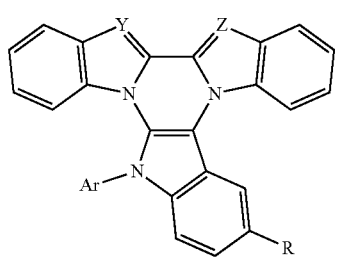
Formula (11b-2)
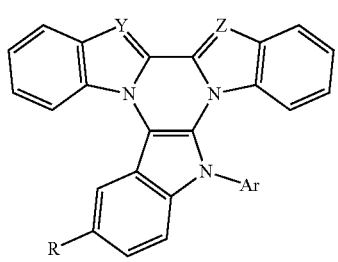

-continued
Formula (12a-2)
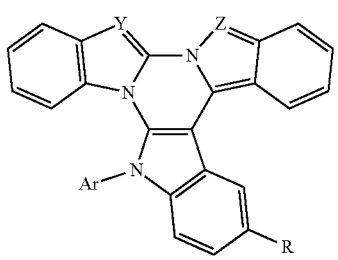
Formula (12b-2)
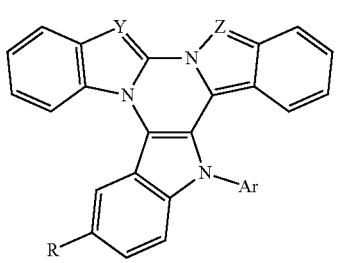
Formula (13a-2)
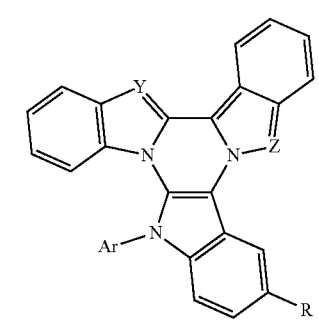
-continued
Formula (13b-2)
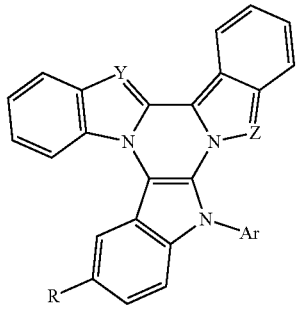
Formula (14a-2)
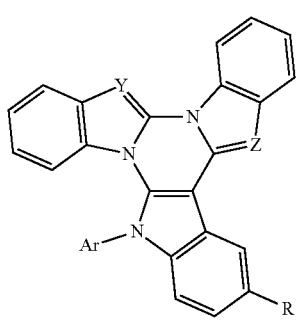
Formula (14b-2)
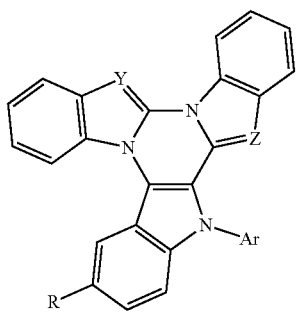
where the symbols used have the definitions given in claim 1.
* * * * *